United States Patent [19]
Barton et al.

[11] Patent Number: 5,869,247
[45] Date of Patent: Feb. 9, 1999

[54] NATURAL RESISTANCE ASSOCIATED MACROPHAGE PROTEIN AND USES THEREOF

[75] Inventors: Charles Howard Barton, Southhampton, United Kingdom; Jacqueline Katie White, Cambridge, Mass.; Jenefer Mary Blackwell, London, United Kingdom

[73] Assignee: The Wellcome Trust Limited as Trustee to the Wellcome Trust, London, United Kingdom

[21] Appl. No.: 676,279

[22] PCT Filed: Jan. 19, 1995

[86] PCT No.: PCT/GB95/00095

§ 371 Date: Oct. 8, 1996

§ 102(e) Date: Oct. 8, 1996

[87] PCT Pub. No.: WO95/20044

PCT Pub. Date: Jul. 27, 1995

[30] Foreign Application Priority Data

Jan. 19, 1994 [GB] United Kingdom .................. 9400929
Oct. 31, 1994 [GB] United Kingdom .................. 9422021

[51] Int. Cl.[6] .............................. C12Q 1/68; C12P 19/34; A61K 38/16; C07H 21/04
[52] U.S. Cl. .............................. 435/6; 435/912; 530/300; 530/387.1; 536/24.1; 536/24.31; 536/24.33
[58] Field of Search .................................. 435/4, 6, 9, 12, 435/320.1; 530/300, 350, 387.1; 536/23.1–24.33, 24.1; 935/6, 8, 77, 78

[56] References Cited

PUBLICATIONS

Vidal et. al. Cell 73:469–485 (May 1993).
Sambrook et. al. Molecular Cloning : A Laboratory Manual. Cold Spring Harbor Press (1989) pp. 17.2 & 17.10–.44.
Baker et. al. J. Cell. Biochem 18p (suppl): 204 (Jan. 4, 1994).
Morgenstern et. al. Nod. Ac. Res. 18:3587–3596 (Jun 25, 1990).
Van Duijn et al in Protein Biotechnology ed. Franks (1993) The Humana Press Inc pp. 365–393.
Augubel et. al ed.s Snovt Protocols in Molecular Biology (1989) John Wiley & Sons. New York pp. 75–78,136–137, 141–142, 158–159, 177–178, 190–194, 201–231.

*Primary Examiner*—W. Gary Jones
*Assistant Examiner*—Debra Shoemaker
*Attorney, Agent, or Firm*—Burns, Doane, Swecker & Mathis, L.L.P.

[57] ABSTRACT

A natural resistance-associated macrophage protein and corresponding promoter and antibodies specific thereto are provided. The promoter region exhibits polymorphisms and is useful as a diagnostic agent.

10 Claims, 22 Drawing Sheets

```
  1  GAATTCGGCACGAGGGAGCTAGTTGCCAGGCCTGGTGACCACACAGAG            10
                                   M  I  S  D  K  S  P  P  R  L

51  TATCCTGCCGCCTGCGTCCTGCTCCTCATGATTAGTGACAAGAGCCCCGAGGCT       26
      S  R  P  S  Y  G  S  I  S  L  P  G  P  A  P

101  GAGCAGGCCCCAGTTATGGCTCCATTTCCAGCCTGCCTGGCCCAGCACCTC          43
      Q  P  A  P  V  C  R  E  T  Y  L  S  E  K  I  P

151  AGCCAGCGCCTTGCCGGGAGACCTACCTGAGTGAGAAGATCCCCATTCCC           60
      S  A  D  Q  G  T  F  S  L  R  K  L  W  A  F  T

201  AGCGCAGACCAGGGTACAATTCAGCCTGAGGAAGCTGTGGGCGTTCACCGG          76
      P  G  F  L  M  S  I  A  F  L  D  P  G  N  I  E

251  GCCTGGTTTCCTCATGAGCATCGCTTTCCTTGACCCGGGAAACATTGAGT           93
      S  D  L  Q  A  G  A  V  G  L  L  C  Q  R  L  A  R  L

301  CCGACCTTCAAGCTGGCCGGCTGTGGCTGGGGTTCAAACTCCTCTGGGTGCTG        110
      L  W  A  T  V  L  G  L  L  C  Q  R  L  A  R  L

351  CTCTGGGCCACTGTGCTGTGCTAGGTTTGCTGTGCCAGCGGGCTGCCCGGCT         126
      G  V  V  T  G  K  D  L  G  E  V  C  H  L  Y  Y

401  GGGCGTGGTGACAGGCAAGGACTTGGGTGAAGTCTGCCATCTCTACTACC           143
      P  K  V  P  R  I  L  L  W  L  T  I  E  L  A  I  V

451  CCAAGGTGCCCCGCATCCTCCTGGCTGACCATTGAGCTGGCCATTGTG             160
      G  S  D  M  Q  E  V  P  G  T  A  I  S  F  N  L  L
```

FIG. 2A

```
501  GGCTCAGATATGCAGGAAGTCATCGGGACGGCTATCTCCTTCAATCTGCT   176
      S  A  R  I  A  G  R  K  V  I  G  T  A  I  S  F  N  L  L
                      P  L                          T  I    V

551  CTCCGCTGGACGCATCCCGCTGTGGGGCGGTGTACTGATCACCATTGTGG   193
      L  R  W  T  H  P  L  W  G  G  V  L  I  T  I  V
      D     F  F  L  F        D  N  Y  G  L  R  K  L  E

601  ACACCTTCTTCTTCCTCTCTCTTGGATAAACTATGGTTTGCGCAAGCTGGAA   210
      T  F  F  F  L  S  L  D  K  L  W  F  A  Q  A  G
      A  F                  I  T  I  M  A  L  T  F  G  Y  E

651  GCTTTCTTCGGTCTCCTCATTACCATAATGGCTTTGACCTTCGGCTATGA   226
      A  F  F  G  L  L  I  T  I  M  A  L  T  F  G  Y
      Y  V  V        H  P  S  Q  G  A  L  L  K  G  L    V

701  GTATGTGGTAGCACACCCCTTCCCAGGAGCGCTCCTTAAGGGCCTGGTGC   243
      V  V  A  H  P  F  P  G  A  L  L  K  G  L  V
      L  P  T  C  P  G  C  Q  G  P  E  L  L  Q  A  V  G

751  TGCCCACCTGTCCCGGCCAGGGCCTGTGGGGCAGCCCGAGCTGCTGCAGGCAGTGGGC   260
      P  T  C  P  G  C  Q  G  P  E  L  L  Q  A  V  G
      I        M  P  H  N    Y  L  H  S  A  L

801  ATCGTCGGTGCCATCATGCCCCATAACATCTACCTGCACTCAGCCTT   276
      I  M  P  H  N  I  Y  L  H  S  A  L
      V  K  S  R  E  V  D  R  T  R  R  V  D  V  R  E

851  GGTCAAGTCTAGAGAAGTAGACAGAACCCGCCGGGTGGATGTTCGAGAAG   293
      V  K  S  R  E  V  D  R  T  R  R  V  D  V  R  E
      A  N  M  Y  F  L  I  E  A  T  I  A  L  S  V  F

901  CCAACATGTACTTCCTGATTGAGGCCACCATCGCCCTATCGGTGTCCTTC   310
      A  N  M  Y  F  L  I  E  A  T  I  A  L  S  V  F
      T     N        F  V  M  A  V  F  G  Q  A  F  Y  Q

951  ATCATCAACCTCTTTGTCATGGCTGTTTTTGGTCAGGCCTTCTACCAGCA   326
      T  N  E  E  A  F  N  I  C  A  N  S  S  L  Q  N
```

FIG. 2B

```
1001  AACCAATGAGGAAGCGTTCAACATCTGTGCCAACAGCAGCCTCCAGAACT  343
       Y   A   K   I   F   P   R   D   N   T   V   S   D   I   Y
1051  ATGCTAAGATCTTCCCCAGGGACAATAACACTGTGTCAGTGGATATTTAT  360
       Q   G   G   V   I   L   G   C   L   F   G   P   A   L   Y   I
1101  CAAGGAGGTGTGATCCTAGGCTGTCTCTTTGGCCCCTGCGGCCCTCTACAT  376
       W   A   V   G   L   L   A   G   Q   F   L   K   S   T   M   T   G
1151  CTGGGCAGTAGGTCTCCTGGCAGCGGGGCAGAGTTCTACTATGACCGGCA  393
       T   Y   A   G   Q   F   V   M   E   G   F   L   R   W   S
1201  CCTATGCAGGACAGTTCGTGATGGAGGGTTTCCTTAAGCTGCGGTGGTCC  410
       R   F   A   R   V   L   T   R   S   C   A   I   L   P   T   V
1251  CGCTTCGCTCGGGTCCTTCACGCGCCTTCTGCGCCATCCCTGCCCACTGT  426
       L   V   A   V   F   R   D   L   K   D   L   S   G   L   N   D
1301  GTTGGTGGCTGTCTCTTCCGAGACCTGAAGGACCTGTCCGGCCTCAACGATC  443
       L   L   N   V   L   Q   S   L   L   P   F   A   V   L   P   I
1351  TACTCAATGTTCTGCAGAGTCTGCTGCCCTTCGCTGTACTGCCCATT  460
       L   T   F   T   S   M   P   A   V   M   Q   E   F   A   N   G   R
1401  TTGACTTTCACCAGCATGCCAGCTGTCATGCAGGAGTTTGCCAACGGCCG  476
       M   S   K   A   I   T   S   C   I   M   A   L   V   C   A   I
1451  GATGAGCAAAGCCATCACTTCGTGCATCATGGCCTAGTCTGCGCCATCA  493
       N   L   Y   F   V   I   S   Y   L   P   S   L   P   H   P   A   Y
```

```
                                                                    2
                  M   I
   1  CCTGCGTCCTCATGATTAgtaatagcctccaggacctaatgggattcca
  51  gtggggtgacttgagggggcaaggaagatttaggtctctgtgggggct
 101  cagctcgccagagcgacttcagtcaggcacttctgtggattaaacctgg
 151  tggagagacagagcatgggggtcaagcagctgagcgagggcctcctgt
 201  ctcacaaatctcctgactcaggggattcttggaacctgagttctgttcct
 251  cactgggaggaagtgattcttggaggtcgagtcgttggcacataggtggac
 301  ctgccagttgcggggaggagtcgaggtcgtgggaggaggcaggtggct
 351  tgaatcccaggctcttgaaagaagcacacccacctagcatcctggggt S   D   K   S   P   P   R   L   S   R   P   S   Y   G    16
 401  ccctgacagGTGACAAGAGCCCCCCGAGGCTGAGCAGGCCCAGTTATGGC S   I   S   S   L   P   G   P   A   P   Q   P   A   P   C   R   E    33
 451  TCCATTTCCAGCCTGCCTGGCCCAGCACCTCAGCCAGCGCCTTGCCGGGA

```
 501 GACCTACCTGAGTGAAGATCCCCATTCCCAGCGCAGACCAGgtaggga
 551 tggtaggaatgtcctcagtgcttcccagtcctaccgatccgagctcgg
 601 accaag---300bp---
 901 tcaagcttgagtgcatgtgtagctgtgtccattatagagcatgcgcgtgg
 951 aggtcagaggacaacttgagagtcagctcacttctactgcgtgggttc
1001 caactctggtggccttagcctctgagcctctgagccccttctcggtcccattgccac
1051 actctaagcagattcctaggctgtcgggccaaacctgaaatagagttga
1101 gtgactgagacctcagtggtccccagagagaagagcctgaagtatgagaa
1151 gggtctggggagggaagagagctgtagcaggagctgagaagcctgagaagaggcaggtttaattacaacaaggt
1201 cccctcttggactctgagaggctgctgctgaacaggaccaacccagaaagcagag
1251 tggccagctgactgagaggctgctgctgaacaggaccaacccagaaagcagag
1301 ccatagtgactcagcaaatggccctggtccctcgggggacgggcagcggt
1351 ggcattgggtgggtgatggaggacagggctggccagcctgactgaagaag
1401 atacctgctgagttttagctgaggggatggtcaaggccagctgcatcca
```

```
            1 2 3 4 5 6 7 8 9         CONSENSUS (4/9)
      3  *  S   + S                   X
         *  D D   D                   X
         *  K   K +                   X
            S + + +      S            (S,A)
            P   P P      P            P
            P P   P P    P     P      P
            R   + + R    R            (R,K)
            L                  L      X
            S S S S      S     S      S
            R R R R R                 R
            P   P P P P P      P      P
            S   S               S     X
         *  Y   Y                     X
            G          G        G     X
            S   S S + S                S
            I      +    I     +       (I,V)
            S +        S              X
            S   S S    S              S
            L      +                  X
            P P P    P P P P P        P
            G  G G G +   G G          G
            P P P    P P P P P        P
            A A      A A              A
            P    P   P   P            P
            Q        Q Q Q            Q
            P P P P P P P P           P
            A                         X
            P P P    P P P P          P
            C                         X
            R   R     R   R           R
            E E              E        X
            T            T +          X
         *  Y            Y            X
            L L                       X
     37  *  S                         X
         *  E E +                     X
         *  K  +                      X
            I  +                      X
```

1. NRAMP CLONE 8.1 DERIVED SEQUENCE
2. NIF - SPECIFIC REGULATORY PROTEIN          12/35   IDENTITIES (34%)
3. GRANULINS PRECURSOR (AGROGRANIN)           13/38   IDENTITIES (34%)
4. FAK PROTEIN TYROSINE KINASE                13/26   IDENTITIES (50%)
5. TEGUMENT PROTEIN UL49                      12/23   IDENTITIES (52%)
6. BETA - 1- ADRENERGIC RECEPTOR              12/21   IDENTITIES (57%)
7. EXTENSIN (PRO RICH GLYCOPROTEIN)           14/30   IDENTITIES (46%)
8. EBNA - 1                                    9/13   IDENTITIES (69%)
9. DYNAMIN (SHIBIRE PROTEIN)                  11/20   IDENTITIES (55%)

FIG. 6

SEQUENCE ALIGNMENT OF EXON 2 FROM HUMAN (TOP) AND MOUSE NRAMP

```
      D   K   G   P   Q   R   L   S   G   S   Y   G   S
ag GT GAC AAG GGT CCC CAA AGG CTA AGC GGG TCC AGC TAT GGT TCC
   -- --- --- A-C --- -CG --- --G --- A-- C-- --T --- --C ---
   S   D   A   S   P   R   L   S   R   P   S   Y   G   S

I   S   S   P   S   P   T   S   G   P   P   Q   A
   ATC TCC AGC CCG ACC AGC CCG ACC AGC GGG CCA CCA CAG CAA GCA
   --T TG- --- --- *   *   *   C-T G-- -CA --- --T --C --C --G
   I   C   S   P   *   *   *   P   G   A   P   P   Q   A

P   P   R   E   Y   T   L   S   E   K   I   I   P   D
   CCT CCC AGA GAG TAC ACC CTG AGT GAG AAG ATC ATC CCC CCA GAC
   -- TG- C-G --- --- --- --C --- --- --- --- --T --C --C AG-
   P   C   R   E   Y   T   L   S   E   K   I   I   P   D   S

T   K   P
   ACA AAA CCG gt
   G-- G-C -A-
   A   D   Q
```

— INDICATES SEQUENCE IDENTITY
\* INDICATES A GAP INTRODUCE TO MAXIMISE ALIGNMENT

SEQUENCE IDENTITIES:  NUCLEOTIDE 115/147 = 77%
AMINO ACID 30/44 = 68% (82% WITH CONSERVED SUBSTITUTIONS)

FIG. 7

ALIGNMENT OF HUMAN NRAMP EXON 2 WITH GENBANK AMINO ACID DATABASE SHOWING SEQUENCE IDENTITIES AND CONSERVED SUBSTITUTIONS (+).

| | 0 | 1 | 2 | 3 | 4 | 5 | 6 | 7 | 8 | 9 | 10 | 11 |
|---|---|---|---|---|---|---|---|---|---|---|---|---|
| | D | D | | | | | | | | | | |
| | K | K | | | | | | | | | | |
| | S | G | | | | | | | | | | |
| | P | P | P | | | | | | | | | |
| | P | Q | | | | | | | | | | |
| | R | R | | | | | | | | | | |
| | L | L | | L | | | | | + | | | |
| | S | S | | | | | | | S | S | | |
| | R | G | | G | | | | | | | | |
| | P | S | | | | | | | S | S | | |
| | S | S | S | | | | | | S | S | | + |
| | Y | Y | | | | | | | | | | Y |
| | G | G | G | G | | | | | | | G | |
| | S | S | + | | | | | | | | S | |
| | I | I | + | + | | | | | | | | |
| | S | S | S | S | S | S | | S | | | | |
| | S | S | | | | + | | + | S | S | + | |
| | | P | | | P | P | | P | P | P | P | P |
| | | T | | + | + | | | | | | + | |
| | | S | | S | | S | | S | S | S | + | |
| | L | P | P | P | | P | P | P | P | P | | |
| | P | T | T | + | | T | + | T | + | + | T | |
| | G | S | S | S | + | | | S | + | + | S | |
| | P | P | | P | P | P | P | P | | | | P |
| | A | G | G | | | | | | | | | G |
| | P | P | P | P | P | P | | P | | | P | P |
| | Q | Q | | | | | + | + | + | | | |
| | P | Q | | | | + | | + | | | | |
| | A | A | + | | A | | | A | + | + | | |
| | P | P | | | | P | | P | P | | | |
| | C | P | P | | P | P | P | | | | P | |
| | R | R | | | R | + | | + | | | | R |
| | E | E | | | | | | E | | | | |
| | T | T | + | | | | | T | | + | T | |
| | Y | Y | | | | | | Y | | | | |
| | L | L | | L | | | | | | | | |
| | S | S | + | | | | | | | + | | |
| | E | E | | | | | | | + | E | | |
| | K | K | | | | | | | | K | | |
| | I | I | I | | | | | | | | | |
| | P | P | | | | | | | | | P | |
| | I | I | | | | | | | | | + | |

FIG. 8A

|    |                                      | IDENTITY TO HUMAN NRAMP |         |
|----|--------------------------------------|-------------------------|---------|
| 0. | MOUSE NRAMP                          | 72%                     | (28/39) |
| 1. | HUMAN - NRAMP                        |                         |         |
| 2. | MICROTUBULE - ASSOCIATED PROTEIN 4   | 32%                     | (14/43) |
| 3. | CYTOKINE RECEPTOR COMMON BETA CHAIN  | 45%                     | (9/20)  |
| 4. | PHOSPHOLIPASE C - BETA 3             | 47%                     | (8/17)  |
| 5. | ZYXIN REGION I (162 - 178)           | 41%                     | (7/17)  |
| 6. | ZYXIN REGION II (265 - 283)          | 36%                     | (7/19)  |
| 7. | ADENYLYL CYCLASE - ASSOCIATED PROTEIN| 39%                     | (9/23)  |
| 8. | ANKRYIN B REGION I (1812 - 1844)     | 30%                     | (10/33) |
| 9. | ANKRYIN B REGION II (1837 - 1871)    | 28%                     | (10/35) |
| 10.| PROTEIN PHOSPHATASE SAL6             | 57%                     | (8/14)  |
| 11.| PTDINS - 3 - KINASE P85 ALPHA        | 37%                     | (7/22)  |

FIG. 8B

```
                                                                        PKC
       EXON1|EXON2
HUMAN  MTG- - - - - - - - - -DKGPQRLSGSSYG- - - - -SISSPTSPTSPGPQQAPPRETYLSEK    42
MOUSE  MIS- - - - - - - - - -DKSPPPRLSRPSYG- - - - -SISSLPGPA- - -PQPAPCRETYLSEK  39
SMF1   MVNVGPSHAAVAVDASEARKRNISEEVFELRDKKDSTVVIEGEAPVRTFTSSSNHERED              60
SMF2   MI- -SQEYEPIQWSDESQTNNDSVNDAY- - - - - -ADVNTTHESRRRTTLQPNST- - - - -     46

PKC                          EXON3|EXON4
       EXON2|EXON3                                                                        1
HUMAN  IPIPDTKPGTFSLRKLWAFTGPGFLMSIAFLDPGNIESDLQLGPVAGFKLLWVLLWATVL            102
MOUSE  IPIPSADQGTFSLRKLWAFTGPGFLMSIAFLDPGNIESDLQAGAVAGFKLLWVLLWATVL             99
SMF1   TYVSKRQVMRDIFAKYLKFTGPGLMVSVAYIDPGNYSTAVDAGASNQFSLLCIILLSNFI            120
SMF2   - - - -SQSMIGTLRKYARFTGPGLMVSVSYMDPGNYSTAVAAGSAHRYKLLFSVLVSNFM           101

EXON4|EXON5
HUMAN  GLLCQRLAARLGVVTGKDLGEVCHLYYPKVPRTVLWLTIELAIVGSDMQEVIGTAIAFNL            162
MOUSE  GLLCQRLAARLGVVTGKDLGEVCHLYYPKVPRILLWLTIELAIVGSDMQEVIGTAISFNL            159
SMF1   AIFLQCLCIKLGSVTGLDLSRACREYLPRWLNWTLYFFAECAVIATDIAEVIGTAIALNI            180
SMF2   AAFWQYLCARLGAVTGLDLAQNCKKHLPFGLNITLYILAEMAIIATDLAEVVGTAISLNI            161
                       2                                                            3
       EXON5|EXON6                              EXON6|EXON7           EXON7|
HUMAN  LSAGRIPLWGGVLITIVDTFFFLFLDNY- - - - - - -GLRKLEAFFGLLITIMALTFGYE-       213
MOUSE  LSAGRIPLWGGVLITIVDTFFFLFLDNY- - - - - - -GLRKLEAFFGLLITIMALTFGYE-       210
SMF1   LI- -KVPLPAGVAITVVDVFLIMF- -TYKPGASSIRFIRIFECFVAVLVVGVCICFAIEL          236
SMF2   LF- -HIPLALGVILTVVDVLIVLL- -AYKPNGS-MKGIRIFEAFVSLLVVLTVVCFTVEL          216
```

FIG. 9A

```
                   EXON8                                                              EXON6|EXON7
HUMAN  -YVVARPEQGALLRGLFLPSCPGCGHPELLQAVGIVGAIIMPHNIYLHSALVKSR------         267
MOUSE  -YVVAHPSQGALLKGLVLPTCPGCGQPELLQAVGIVGAIIMPHNIYLHSALVKSR------         264
SMF1   AYIPKSTSVKQVFRG-FVPSAQMFDHNGIYTAISILGATVMPHSLFLGSALVQPRLLDYD         295
SMF2   -FYAKLGPAKEIFSG-FLPSKAVFEGDGLYLSLAILGATVMPHSLYLGSGVVQPRLREYD         274
                                    4                                  5

HUMAN  -------EIDRARRVDIREANM------YFLIEATIALSVSFIINLFVMAAFGQAFY             311
MOUSE  -------EVDRTRRVDVREANM------YFLIEATIALSVSFIINLFVMAVFGQAFY             308
SMF1   VKHGNYTVSDEQDKVKKSKSTEEIMEEKYFNYRPTNAAIKYCMKYSMVELSITLFTLALF          355
SMF2   IKNGHY-LPDAND----------------MDNNHDNYRPSYEAISETLHFTITELLISLFTVALF     322
                    *             = = =                            6

EXON9|EXON10                                   EXON10|EXON11
HUMAN  QKTKQAAFNICANSSLHDYAKIFPMNNATVAVDIYQGGVILGCLFGPAALYIWAIGLLAA          371
MOUSE  QQTNEEAFNICANSSLQNYAKIFPRDNNTVSVDIYQGGVILGCLFGPAALYIWAVGLLAA          368
SMF1   VN------CAILVVAG-STLYNSPE-ADGADLFTIHELLSRNLAPAAGTIFMLALLLS            405
SMF2   VN------CAILIVSG-ATLYGSTQNAEEADLFSIYNLLCSTLSKGAGTVFVLALLFS            373
                                                         7

EXON11|EXON12
HUMAN  GQSSTMTGTYAGQFVMEGFLRLRWSSFARVLLTRSCAILPTVLVAVFRDLRDLSGLNDLL          431
MOUSE  GQSSTMTGTYAGQFVMEGFLKLRWSRFARVLLTRSCAILPTVLVAVFRDLKDLSGLNDLL          428
SMF1   GQSAGVVCTMAGQIVSEGHINWKLQPWQRRLATRCISIIPCLVISICIGREALSKALNAS          465
SMF2   GQSAGIVCTLSGQMVSEGFLNWTVSPALRRSATRAVAITPCLILVLVAGRSGLSGALNAS          433
```

FIG. 9B

```
                EXON12|EXON13                                                           EXON13|EXON14
HUMAN  NVLQSLLLPVAVLPILTFTSMPTLMQ-------------------------EFANGLLNKVVTSSI         472
MOUSE  NVLQSLLLPFAVLPILTFTSMPAVMQ-------------------------EFANGRMSKAITSCI         469
SMF1   QVVLSIVLPFLVAPLIFFTCKKSIMKTEITVDHTEEDSHNHQNNNDRSAGSVIEQDGSSG              525
SMF2   QVVLSLLLPFVSAPLLYFTSSKKIMRVQLNRTKELSRTTDKKPVADRTEDD--ETIELEE              491
                    8                          9
                                                 EXON14|EXON15
HUMAN  MVLVCTINLYFVVSYLPSLPHPAYFGLAALLAAYLGLSTYLVWTCCLAHGATFLAHSSH               532
MOUSE  MALVCAINLYFVISYLPSLPHPAYFGLTAYLAWTCCIAHGATFLTHSSH                         529
SMF1   MEIENGKDVKIV------Y--MANNWITVIAI----IVW----------LFLSLL                   559
SMF2   MGIGSSSQERSLVS-------PAPEYKDMSNGMIVTVLAI----IVW----------LIISGL           533
                    10

HUMAN  HHFLYGLLEEDHKG-ETSG       550
MOUSE  KHFLYGLPNEEQGGVQGSG       548
SMF1   N--VYAIVQLG-MSHEVIG       575
SMF2   N--FYMLLGFT-TGKGDHL       549
```

FIG. 9C

| GENE NAME | CONSERVED AMINO ACID SEQUENCE | % IDENTITY TO HUMAN NRAMP |
|---|---|---|
| | * * PKC | |
| HUMAN NRAMP | DKGPQRLSGSSYGSISSPTSPTSPGPQQAPPRETYLSEKIPI | |
| MOUSE NRAMP | DKSPPRLSRPSYGSISS    LPGPAPQPAPCRETYLSEKIPI | 72% (28/39) |
| MICROTUBULE - ASSOCIATED PROTEIN 4 | P   S G++S     PTS GP  + PR + L +  I | 32% (14/43) |
| CYTOKINE RECEPTOR COMMON β CHAIN | L G  G +S  + P+SP P | 45% (9/20) |
| PHOSPHOLIPASE C - β3 | S P+S  +P P  A PR | 47% (8/17) |
| ZYXIN REGION I (162-178) | S+P   PT P P + P+ | 41% (7/17) |
| ZYXIN REGION II (265-283) | SP+ P  +  PP  TY  + | 36% (7/19) |
| ADENYLYL CYCLASE - ASSOCIATED PROTEIN | S+P   TSP  P++A  +E | 39% (9/23) |
| ANKYRIN B REGION I (1812-1844) | +S SS      SP SP++     + +P    +   + K | 30% (10/33) |
| ANKYRIN B REGION II (1837-1871) | S SS      SP SP++     + +P    T   P+ | 28% (10/35) |
| PROTEIN PHOSPHATASE SAL 6 | GS  +P+SPTS   P | 57% (8/14) |
| PTDINS - 3 - KINASE P85α | +Y     P +     PGP    PR | 35% (8/14) |
| | | |
| CONSENSUS | XXXPXXLSXSSYGSXSSPXSPTSPGPXXAPPRETYLXEKIPX | |
| | *                              * | |

FIG. 10A

|               |                                                                              |
|---------------|------------------------------------------------------------------------------|
| HUMAN NRAMP   | AFGQAFYQKTKQAAFNICANSSLHDYAKIFPMNNATVAVDIYQGGVILGCLFGPAALYIW                  |
| MOUSE NRAMP   | VFGQAFYQQTNEEAFNICANSSLQNYAKIFPRDNNTVSVDIYQGGVILGCLFGPAALYIW                  |
| SMF 1         | LFTLALFVN--------CAILVVAG-STLYNSPE-ADGADLFTIHELLSRNLAPAAGTIF                  |
| SMF 2         | LFTVALFVN--------CAILIVSG-ATLYGSTQNAEEADLFSIYNLLCSTLSKGAGTVF                  |
| O. SATIVA     | VSGT------------VCNATNLSPEDAV-----KCSDLTLDSSSFLLRNVLGKSSATVY                  |
| A. THALIANA   | VSGA------------VCNAPNLSPEDRA-----NCEDLDLNKASFLLRNVVGKWSSKLF                  |
|               |                              *                                               |

|               |                                                                              |
|---------------|------------------------------------------------------------------------------|
| HUMAN NRAMP   | AIGLLAAGQSSTMTGTYAGQFVMEGFLRLRWSSFARVLLTRSCAILPTVLVAVFRDLRDL                  |
| MOUSE NRAMP   | AVGLLAAGQSSTMTGTYAGQFVMEGFLKLRWSRFARVLLTRSCAILPTVLVAVFRDLKDL                  |
| SMF 1         | MLALLLSGQSAGVVCTMAGQIVSEGHINWKLQPWQRRLATRCISIIPCLVISICIGREAL                  |
| SMF 2         | VLALLFSGQSAGIVCTLSGQMVSEGFLNWTVSPALRRSATRAVAITPCLILVLVAGRSGL                  |
| O. SATIVA     | GVALLASGQSSTITGTYAGQYVMQGFLDIKMKQWLRNLMTRSIAIVPSLIVSII------                  |
| A. THALIANA   | AIALLASGQSSTITGTYAGQYVMLGFLDLRLEPW--------------------------                  |

FIG. 10B ctgcagtgccttcctctgtggccctcaaagggaaactgaagcctttgaggacatgaagac tcgcattaggccaacgaggggtcttggaactccagatcaaagagaataagaaagacctga

PUTATIVE Z-DNA FORMING REPEAT ctctgtgtgtgtgtacgtgtgtgtgtgtgtgtggcagagggggtg tggtcatgggtattgacatgaatacgcaagggcaggaagcatctgaaatcagagctaa cttgggaggcacagaacacggggtgcctggaacagatgtgttgtggggcacaggg caggctgggaggaacaaaggtccactccatgggtaaccagacccttccgccagggctgg

FIG. 11A ccacttctgcctttggaaaatgtttcacaacgccccatgttgtgtgtgtgtgaatcgg

TRANSCRIPTION START SITE atgtaagaggcagggcactcggctgcggatgggtaaac ccgatgtgaaccgaatgttg agggcgtgggctggcacacttacttgcaccagtgcccagagagaggggtgcaggctgagga

M   T gctgcccagagcaccgctcacactcccagagtacctgaagtcggcatttcaATGACAGgt

▭ = INTERFERON-7 RESPONSE ELEMENT

▭ = NFXB SITE

▭ = AP1 SITE

▨ = W-ELEMENT ggaa/ttcc = PU.1 CORE MOTIF

······· = AP1-LIKE

▬ = PEA3 SITE

NATURAL RESISTANCE ASSOCIATED MACROPHAGE PROTEIN AND USES THEREOF

FIELD OF THE INVENTION

The present invention relates to a nucleotide sequence encoding a natural resistance-associated macrophage protein, the protein product thereof, nucleotide probes and primers thereto, polypeptide fragments of the protein and related antibodies.

BACKGROUND TO THE INVENTION

Macrophages are the main phagocytic cells of animals and play a key role in the immune system. Macrophages bind and injest particles recognised as foreign by the immune system. Such particles include microorganisms.

The three microorganisms *Salmonella typhimurium*, *Leishmania donovani* and *Mycobacterium bovis* (BCG) are all intracellular pathogens of macrophages. Three separate groups of scientists had previously identified genes capable of controlling resistance and susceptibility to each of these microorganisms. The genes were designated respectively Ity, Lsh and Bcg. Subsequent work has led the scientists to conclude that Ity/Lsh/Bcg is a single gene and is expressed at the macrophage level (Ref 1).

Recently, Vidal et al (Ref 2) cloned a murine gene as the most likely candidate to be Lsh/Ity/Bcg. This gene has been termed the natural resistance-associated macrophage protein (Nramp) gene. A cDNA for Nramp was isolated from a pre B-cell cDNA library and sequenced. The amino acid sequence for the protein product was deduced from the nucleotide sequence and predicts a 53 kDa protein. On the basis of the deduced amino acid sequence, Vidal et al proposed as a function of the Nramp protein the transport of nitrate across the membrane of the intracellular vacuole of the macrophage containing the microorganisms. In the acid environment of this vacuole, the nitrate could be converted via nitrite to toxic nitric oxide thereby to enhance killing of the microorganisms.

The present applicants have isolated and sequenced a macrophage expressed Nramp cDNA. Contrary to the teaching of Vidal et al the present applicants have found a different nucleotide sequence including a region encoding an additional amino acid sequence at the N-terminus. Surprisingly, the additional amino acid sequence includes structural features which may be responsible for protein-protein interactions essential in signal transduction pathways thereby suggesting that Nramp controls early amplification of transmembrane signalling in disease resistant macrophages by binding the SH3 domain of tyrosine kinases or other molecules.

SUMMARY OF THE INVENTION

The present invention provides in one aspect a natural resistance-associated macrophage protein having an N-terminal region comprising an SH3 binding domain. When present in the macrophage, the protein is capable of controlling resistance to pathogenic microorganisms. SH3 (Src homology 3) domains are believed to mediate specific protein-protein interactions required in signal transduction (Ref 3) and have been identified as related sequences in a variety of proteins (Refs 4 and 5). In one embodiment of the present invention, the SH3 binding domain comprises the SH3 binding motif PGPAPQPXPXR (SEQ ID NO: 1), more particularly PGPAPQPAPCR (SEQ ID NO: 2). This motif is found in the protein obtainable from mice. In another embodiment of the present invention, the SH3 binding domain comprises the SH3 binding motif PXSPTSPXPXX-APPRXT (SEQ ID NO: 3), more particularly PTSPTSPG-PQQAPPRET (SEQ ID NO: 4). This motif is found in the protein obtainable from humans. Typically, SH3 binding domains are rich in proline and sometimes serine. Preferably, the SH3 binding domain obtainable from mice further comprises the polypeptide segment (S,A)PP(R,K)XSRPXXXS(I,V)XSX (SEQ ID NO: 5) at the N-terminal end of the SH3 binding motif. More particularly, the polypeptide segment is SPPRLSRPSYGSISSL (SEQ ID NO: 6). The SH3 binding domain obtainable from humans preferably further comprises the polypeptide segment GPQRLSGSSYGSISS (SEQ ID NO: 7).

A further preferred feature of the N-terminal region is the presence of one or more consensus sequences for protein kinase C (PKC) phosphorylation. Preferably, the N-terminal region has two protein kinase C sites which flank the SH3 binding domain. Tyrosine residues may also flank the SH3 binding domain.

Typically, the N-terminal region comprises 64 amino acids.

The full amino acid sequences of the murine and human proteins are set out in FIG. 9. Mutations or deletions may be present in each sequence provided that they do not substantially affect the activity of the protein.

In a second aspect, the present invention provides a nucleotide sequence encoding the natural resistance-associated macrophage protein discussed above. Where the nucleotide sequence is a DNA sequence, this may be a genomic sequence containing introns and exons or a cDNA sequence obtainable from mRNA by reverse transcription. The SH3 binding domain of the protein obtainable from mice is preferably encoded by the DNA sequence comprising CCTGGCCCAGCACCTCAGCCAGCGCCTTGCCGG (SEQ ID NO: 8) and may further comprise the upstream region AGCCCCCCGAGGCTGAGCAGGCCCAGT-TATGGCTCCATTTCCAGCCTG (SEQ ID NO: 9). More particularly, the 5' end of the genomic DNA sequence is set out in FIG. 4 and discussed in further detail below. A cDNA sequence is also provided, as set out in FIG. 2. The SH3 binding domain of the protein obtainable from humans is preferably encoded by the DNA sequence comprising CCG ACC AGC CCG ACC AGC CCA GGG CCA CAG CAA GCA CCT CCC AGA GAG ACC (SEQ ID NO: 10) and may further comprise the upstream region GGT CCC CAA AGG CTA AGC GGG TCC AGC TAT GGT TCC ATC TCC AGC (SEQ ID NO: 11).

It will be readily appreciated by one skilled in the art that various modifications and deletions of the particular nucleotide sequences described may still result in a functional protein product. Owing to the degeneracy of the genetic code it will be readily apparent that numerous silent mutations within the specified sequences will give rise to the same amino acid sequence.

The cDNA sequence has been deposited as part of plasmid pBabeλ8 .1 under accession number NTC 12855 at the National Collection of Type Cultures, Central Public Health Laboratory, London, UK. The deposit consisted of a culture of *E. Coli* DH5α transformed with the plasmid and was given the date of deposition of 14 Jan. 1994.

In a further aspect, the present invention provides a retroviral vector construct incorporating a cDNA sequence encoding the natural resistance-associated macrophage protein.

Generally, the use of retroviral vectors presents a good method for gene transfer into haematopoietic cells and has advantages over other methods including stable transfer of a single copy of a gene into the recipient cell, and high efficiency of gene transfer into target cells. Vector constructs are generated by ligating the gene of interest using standard molecular biology techniques into a non-replication-competent viral genome. The resultant vector construct is transferred into a cell line (the packaging cell line) capable of replicating the viral genome and packaging it into infective pseudovirus particles. Depending on the virus envelope protein encoded by the packaging cell, the resulting pseudovirus particles can be capable of infecting a wide host range (amphotropic) or be restricted to rodent cells (ecotropic).

In the present application the pBabe plasmid was used as a suitable retroviral vector. This plasmid is discussed in further detail in (Ref 6). Plasmid pBabeλ.8.1 may be introduced into a suitable packaging cell, such as the GP+86 ecotropic packaging cell (Ref 7) and recombinant clones selected for the linked marker gene which confers antibiotic resistance. Antibiotic resistant clones can then be tested for their ability to secrete functional pseudovirus particles and to infect recipient cells.

The selected retroviral constructs of the gene carrying Nramp can be used as the basis for gene therapy to create a functional copy of the gene where lack of expression has been observed, or where a non-functional copy exists. The most likely method of gene transfer is via the bone marrow or progenitor cells isolated from the circulation. The gene can be retrovirally introduced into these stem cells removed from the patient. The stem cells would then be reintroduced into the patient with the aim of repopulating the myeloid/lymphoid cell lineages with cells containing a functional copy of the gene.

In a further aspect, the present invention provides nucleotide probes or primers capable of hybridizing to a portion of the nucleotide sequence described, preferably to at least a portion of the sequence above which encodes the N-terminal region of the protein comprising or upstream of the SH3 binding domain. Probes can be single or double stranded and can be made by recombinant DNA technology from copies of the gene, or portions thereof, or by synthetic routes such as which lead to oligonucleotide probes. Primers, such as those for polymerase chain reaction work, are single stranded and preferably are at least 18 nucleotides long. Both probes and primers based on the sequence can be used at both DNA and RNA levels for diagnosis and such probes and primers can be readily made using the sequence information provided herein. The cDNAs as described above are themselves useful probes for the gene. The present applicants have found that the cDNA sequence of the murine gene described above can be successfully used as a probe for the corresponding human gene.

The probes or primers have diagnostic potential, for example to detect gene deletion or absence of expression of the gene in cells of the myeloid or lymphoid lineage. They may also be used to detect polymorphism at the gene locus which may result in an expressed but sub-functional or non-functional protein. Genetic defects to be diagnosed may occur in the coding sequence, or in the promoter or 3' untranslated regulatory regions of the gene and so probes directed to both genomic and cDNA sequences may be useful.

Primer pairs are also provided which are capable of hybridising to specific sequences in the 5' region of the human NRAMP gene, permitting amplification of a portion of the promoter region of the human gene. The promoter region preferably includes a poly gt site, especially in the configuration t(gt)$_5$ac(gt)$_5$ac(gt)$_n$g in which n=o, or an integer. The promoter region may further comprise a transcription site, and, optionally, one or more of: an Interferon-Y response element; a NFKB site; an AP-1 site; a W-element; a PV.1 core motif; and a PEA3 site. Preferably each of the sites, elements or motifs are present in the order specified in FIG. 11. Polymorphisms in the poly gt site, specifically located in the third cluster of gt repeats, where n may equal any number of repeats, typically 4 to 12, may be diagnostic for reduced or defective expression of the human gene and so primers permitting PCR amplification of this region are of particular importance. Probes to the promoter region are also provided, preferably allele-specific probes to the promoter region, for example allele-specific oligonucleotides.

In a preferred embodiment, the human protein is encoded by 15 exons, each of which is flanked by intron boundary regions. The exons are preferably those shown in Table 3. Probes or primers are provided, which are capable of hybridising to at least a portion of an individual exon and/or its flanking intron boundary region. Preferably, primer pairs are provided which are capable of hybridising to the intron boundaries of each exon so as to amplify the respective exon. More preferably, the primer pairs are capable of hybridisation to any one of the intron boundary regions shown in Table 3, especially the underlined regions. Polymorphisms in any of the exons of the human gene may be diagnostic of a defective gene product, and so primers permitting PCR amplification of exons to identify such polymorphisms using electrophoretic techniques are of particular importance. More preferably, the primer pair capable of hybridisation to the intron boundaries 5' and 3' of human exon 2, permitting PCR amplification of this exon, may be critically important in permitting detection of a polymorphism involving a 3 amino acid deletion in the putative SH3 binding domain encoded within this exon. The importance of this region to the function of the NRAMP gene represents a key component of this invention.

Antisense oligonucleotides may also be produced using the nucleotide sequence described above. Antisense oligonucleotides may be used to interrupt the expression of the gene and this could provide a potentially important local therapy for autoimmune disorders or cancers.

As discussed in further detail below, the protein product from the gene is predicted to be a polytopic membrane protein. Whilst antibodies against the protein will be important tools in diagnosing levels of expression of the protein product in various cell populations, only those portions of the protein which are not occluded by membrane are likely to be accessible to antibodies in the intact or native protein conformation. Accordingly, in a further aspect of the present invention there is provided a polypeptide fragment of the protein which comprises at least a portion of the structural domain not hidden by membrane. Preferably, the polypeptide fragment comprises at least a portion of the N-terminal region. Two structural domains of potential importance are: the N-terminal cytoplasmic domain proximal to the first membrane-spanning domain and comprising amino acids 1 to 82; and the C-terminal cytoplasmic domain distal to the last membrane-spanning domain and comprising amino acids 414 to 458.

In practice, fusion proteins including those cytoplasmic domains may be engineered by PCR, for example using a glutathione-S-transferase gene downstream of which the relevant sequences from Nramp are ligated. The pGEX series of prokaryotic expression vectors is a particularly useful type of vector into which the Nramp sequences may be ligated. This is a standard procedure, further information about which may be found in (Ref 8).

In a further aspect, the present invention provides an antibody to the natural resistance-associated macrophage protein or an antibody to a polypeptide fragment therefrom, more particularly to one of the accessible polypeptide domains discussed above. The Nramp fusion proteins may be used as antigens to innoculate rabbits or rats so as to produce antibodies. Using standard techniques both polyclonal and monoclonal antibodies may thus be raised.

In particular, antibodies recognising epitopes within specific amino acid sequences contained within the N-terminal (DKSPPRLSRPSYGSISS (SEQ ID NO: 12); PQPAPCRETYLSEKIPIP (SEQ ID NO: 13); and GTFSLRKLWAFTG-PGFLMSIAFLDPGNIESDLQ (SEQ ID NO: 14) ) and C-terminal (WTCCIAHGATFLTHSSHKHFLYGL (SEQ ID NO: 15) ) regions of the protein will recognise the protein in both mouse and man, and can be applied for both research purposes and as a diagnostic tool in man.

In addition to diagnosis as discussed above, neutralizing monoclonal antibodies could be produced to block the function of the gene in situations where adverse effects are observed, such as autoimmunity or cancer resulting from expression of the gene.

The presence or absence of the gene product could have both beneficial and detrimental effects depending on the disease status. In infectious diseases, particularly involving intracellular pathogens of the myeloid cell lineage, absence of a functional gene product may result in chronic susceptibility to the disease. In the case of autoimmune disorders or cancers of the myeloid or lymphofunctional gene overexpression of the functional gene product and resultant hyper-activation of macrophages may contribute to the disease phenotype. The diagnostic processes and therapeutic agents described herein may be useful for patients presenting with atypical responses to infection, certain autoimmune disorders, or cancers of the myeloid or lymphoid lineages.

Another situation in which a deficit in the NRAMP gene might relate to cancer is where cancers of other cell lineages are destroyed by activated macrophages, through sensitivity to hydrogen peroxide generated by a respiratory burst response, TNFα, or nitric oxide. All of these macrophage functions are regulated by NRAMP. In this case, corrective gene therapy via stem cell gene transfer would be appropriate.

BRIEF DESCRIPTION OF THE DRAWINGS

The present invention will now be described further by way of example only with reference to the attached drawings in which:

FIG. 2 shows the sequence of macrophage-λ8.1 Nramp (SEQ ID NOS: 49 and 50) in accordance with the present invention;

FIG. 4 shows the 5' sequence (SEQ ID NOS: 51 and 52) of the genomic DNA up to nucleotide 1911;

FIG. 6 shows the result of an amino acid database search (29) with the 64 amino acid sequence at the N-terminal end of macrophage-expressed Nramp;

FIG. 7 shows the nucleotide (SEQ ID NO: 53 and 55) and deduced amino acid sequence (SEQ ID NO: 54 and 56) of exon 2of human NRAMP;

FIG. 8 shows the result of an amino acid database search with the N-terminal sequence for human NRAMP;

FIG. 9 shows the result of a Clustal V multiple sequence alignment for the deduced amino acid sequence for human NRAMP (SEQ ID NO: 57), murine Nramp clone λ8.1 (SEQ ID NO: 50) [55], and the yeast mitochondrial proteins SMF1 (SEQ ID NO: 58) and SMF2 (SEQ ID NO: 59) [35];

FIG. 10(A) shows the results of amino acid database searches for human NRAMP exon 2(SEQ ID NO: 54, 56 and 60);

FIG. 10(B) shows the results of a Clustal V multiple sequence alignment for human NRAMP (SEQ ID NO: 57), mouse Nramp (SEQ ID NO: 50), SMF1 (SEQ ID NO: 58) and SMF2 (SEQ ID NO: 59), and the expressed sequence tags [60] of *Oryza sativa* (SEQ ID NO: 61) (rice; accession number d15268) and *Arabidopsis thaliana* (SEQ ID NO: 62) (accession number z30530) genes, reading frames 1 and 2 respectively;

FIG. 11 shows the 440 bp of putative promoter region human NRAMP sequence 5' of the transcription start site (SEQ ID NO: 63)

DESCRIPTION OF THE PREFERRED EMBODIMENTS

Details of Experimentation and Results

Sequence-analysis of Nramp clones from macrothage cDNA library. Macrophage Nramp clones were isolated from an activated (4 h stimulation; 25 U/ml interferon-γ, 10 ng/ml *Salmonella typhimurium* LPS) mouse (B10.L-Lsh$^r$) macrophage cDNA library prepared in lambda UniZap (Stratagene). Clones were isolated by filter plaque hybridisation using a probe generated by RTPCR corresponding to nucleotides 1410–1812 bp of the published (Ref 2) sequence. Following plaque purification 35 clones from $10^6$ recombinants were analysed by PCR using sense and antisense Nramp primers in combination with T3 and T7 vector arm primers. This allowed the mapping of clones with respect to the published sequence. 20/35 were found to be 1.0–1.5 kb and were not analysed further. The remainder were of 2.1–2.3 kb and potentially encoded full length Nramp coding sequence. Clones were initially restriction mapped and four selected for sequencing (Sequenase II) including the longest clone λ8.1.

Genomic sequencing

From the macrophage cDNA sequence, PCR primers were generated to amplify a 2 kb region of DNA from both yeast artificial chromosome (YAC clone C9C28; Princeton library) and mouse genomic DNAs. The products were cloned in the pCR vector (Invitrogen) and sequence (Sequenase II) determined from double stranded plasmid DNA from at least two clones of each, using oligos complementary to the cDNA sequence. Splice junctions were identified by comparison of the genomic and complementary DNA sequences.

Northern blot and primer extension analysis of Nramp expression

Cytoplasmic total RNA isolated in the presence of vanadyl ribonucleoside complexes was utilised for denaturing gel electrophoresis with glyoxal and Northern blotting, or directly for RT reactions for primer extension analysis. Hybridizations were performed using probes isolated from a genomic fragment (bp 1–1482) 5' of exon 3 (see results).

Restriction digestion with BamHI generated two probes covering a λ8.1-specific (=bp 1–587 of the genomic sequence; FIG. 2b) region or the putative 5' untranslated sequence (=bp 588–1482 of the genomic sequence; FIG. 2b) of the published (Ref 2) cDNA. For primer extensions oligonucleotides designed to be specific for λ8.1-like RNAs (TCT GCG CTG GGA ATG GGG (SEQ ID NO: 16); bp 538–521 of the genomic sequene) or for the putative 5' UTR of the published sequence (TGC AAG CAG ATC GGG TCA (SEQ ID NO: 17); bp 1482"1465 of the genomic sequence), were labelled with polynucleotide kinase. Extension reactions were performed with 25 Units of AMV reverse transcriptase at 42° C., terminated by the addition of gel loading buffer, and sized against a sequencing ladder following denaturing polyacrylamide gel electrophoresis.

Figure 1:
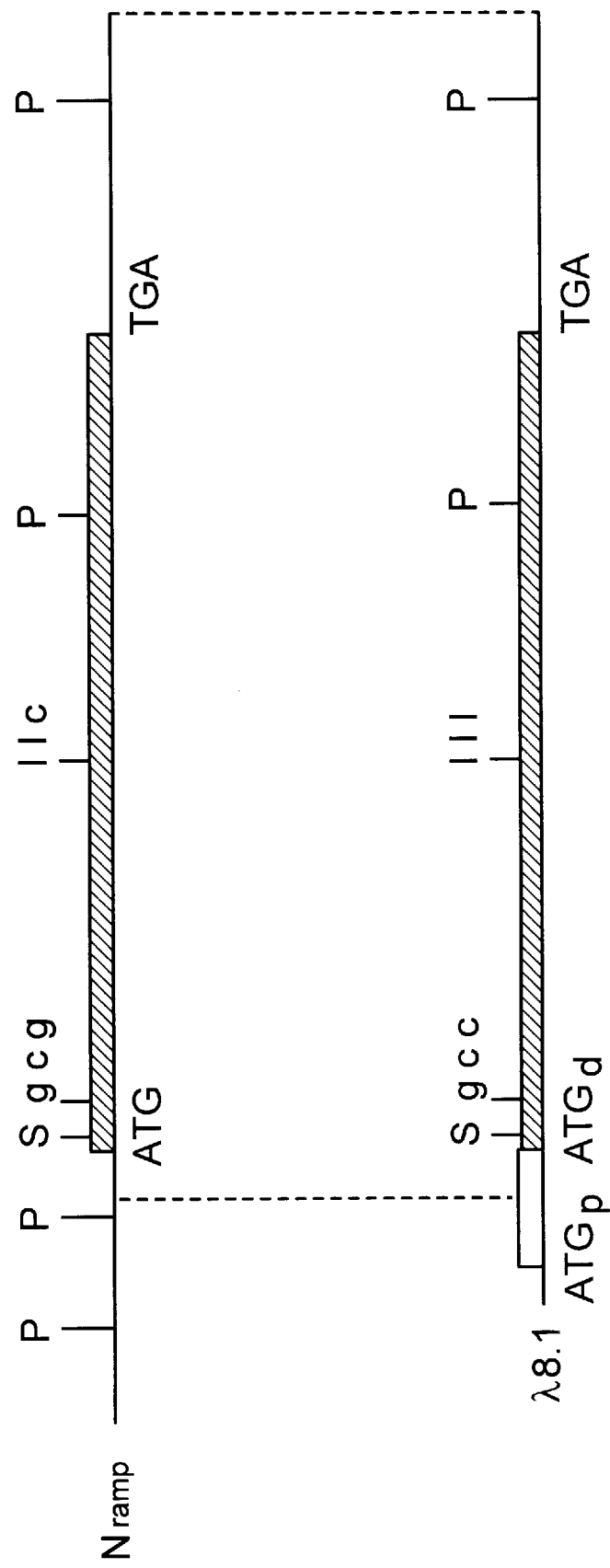
FIG. 1 shows a restriction map of the Nramp λ8.1 cDNA clone of the present invention as compared with that of Vidal et al.

Referring to FIG. 1, cDNA clones isolated from an activated macrophage library carrying the resistant allele of murine Nramp were restriction mapped, sequenced and found to be identical over the coding region of the published (Ref 2) sequence, except for two silent mutations (359 bp, C; 965 bp, T). Regions of sequence identity between the published clone and macrophage clone λ8.1, which includes the ATG (d) codon and the major ORF (solid bars) of the published clone, are shown within the broken lines. The positions of SmaI (S) and PvuII (P) cleavage sites demonstrate divergence between the clones at the 5' end. Novel sequence identified in the 5' region of λ8.1 contained a more proximal ATG (p) codon and an extended ORF (open bar) encoding an additional 64 N-terminal residues compared with the published Nramp.

FIG. 2 shows the sequence of macrophage λ8.1. The nucleotide sequence specific to λ8.1 is underlined. The 64 N-terminal residues encoded by λ8.1 occur 5' of the distal initiation codon (=Met at position 65) identified by Vidal and coworkers (Ref 2). This additional 64 amino acid sequence is identical in resistant and susceptible mice (data not shown) and is rich in Ser 10/64, Pro 10/64, basic 7/64 residues, and contains 3 consensus PKC phosphorylation site s (S/T-X-R/K) on Ser 3, 37, and 52. As described previously (Ref 2), putative N-linked glycosylation sites occur at residues 311 and 325, and hydrophobic potential membrane-spanning domains are underlined. Database searches also revealed a B-2 alu-like repetitive element (boxed) within the 3' UTR, which produces complex signals when the full-length λ8.1 clones is hybridised to mouse genomic DNA.

Figure 3:
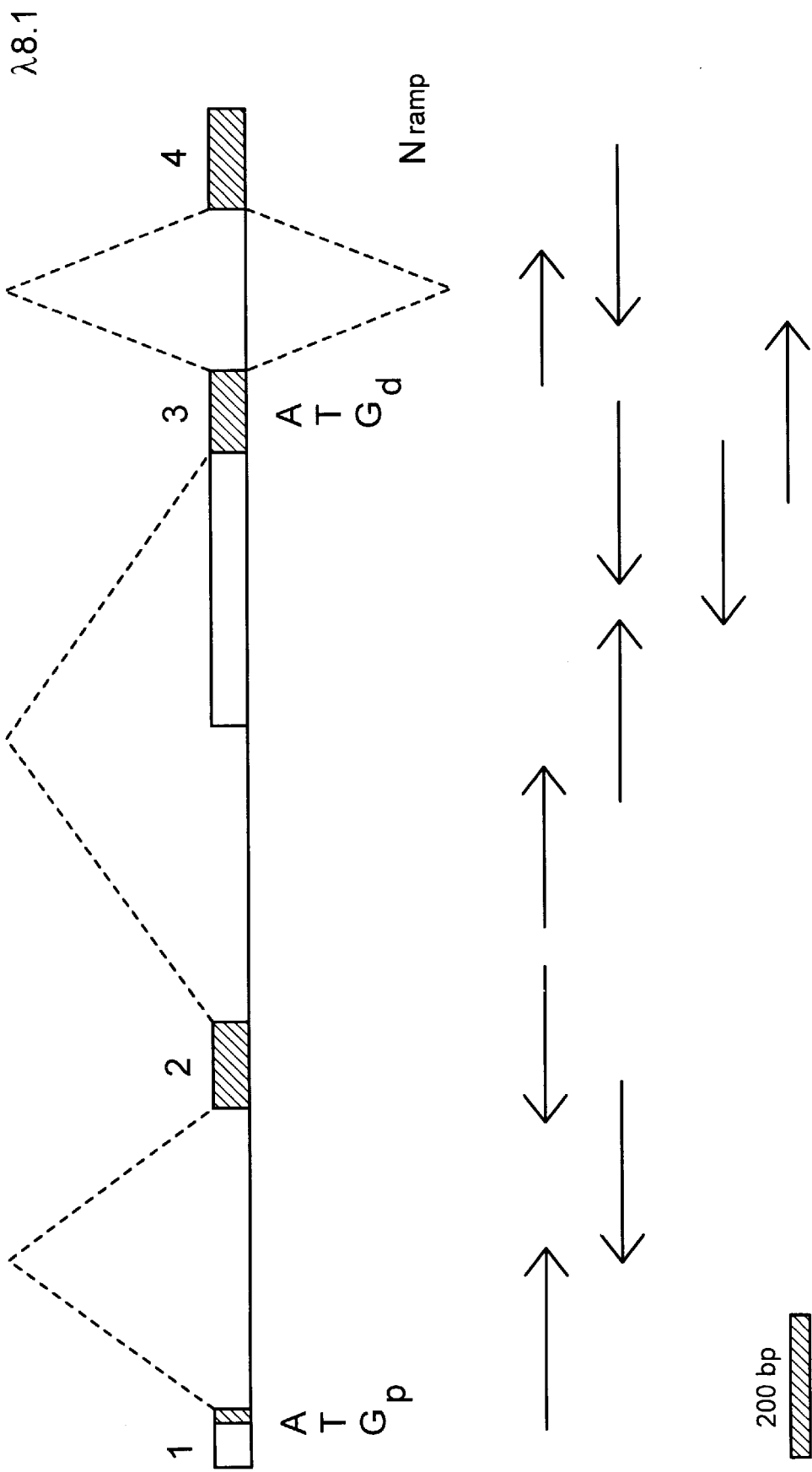
FIG. 3 is a schematic representation of the genomic DNA corresponding to nucleotides 31 to 456 of λ8.1 as compared with the corresponding DNA of Vidal et al.

It will be apparent from FIG. 3 that the N-terminal cytoplasmic domain of macrophage Nramp is encoded by two unique and two common exons. The region of genomic DNA corresponding to nucleotides 31–456 of λ8.1 and spanning the point of divergence with the published (Ref 2) clone was isolated and sequence determined to elucidate the mechanism generating the two clones. The additional sequence of macrophage Nramp is encoded by two unique exons (1 and 2; solid bars) contiguous in the cDNA sequence (FIG. 1) with exons (3 and 4; solid bars) common to both λ8.1 and the published clone. Contiguous with and 5' of the third exon is the putative 5' UTR (open bar) found in the published clone. Predicted splicing patterns (dotted line) are indicated above (λ8.1) and below (published pre-B cell clone) the map. Also shown are the sequencing gel reads (arrows) determined using specific Nramp primers from the cDNA sequence, as well as new primers specific to the genomic sequence.

FIG. 4 shows the sequence of genomic DNA spanning the point of divergence of λ8.1 and the published (Ref 2) sequence. Exonic nucleotide sequence is shown in capitals, with the predicted amino acid sequence indicated above in single letter format. Intron sequence is shown in small letters. The region of 5' UTR from the published clone, contiguous with the third exon, is highlighted by overlining. The codon (ATG=Met) where this terminates indicates the initiation codon of the published sequence. A probe containing sequence unique to the 5' region (bp 1–587) of the mouse genomic sequence also hybridises to genomic Lamda clones isolated from a subcloned human YAC (clone AM11/D3/14; ICRF library) known to hybridise to the homologous region of human 2q35.

Figure 5:
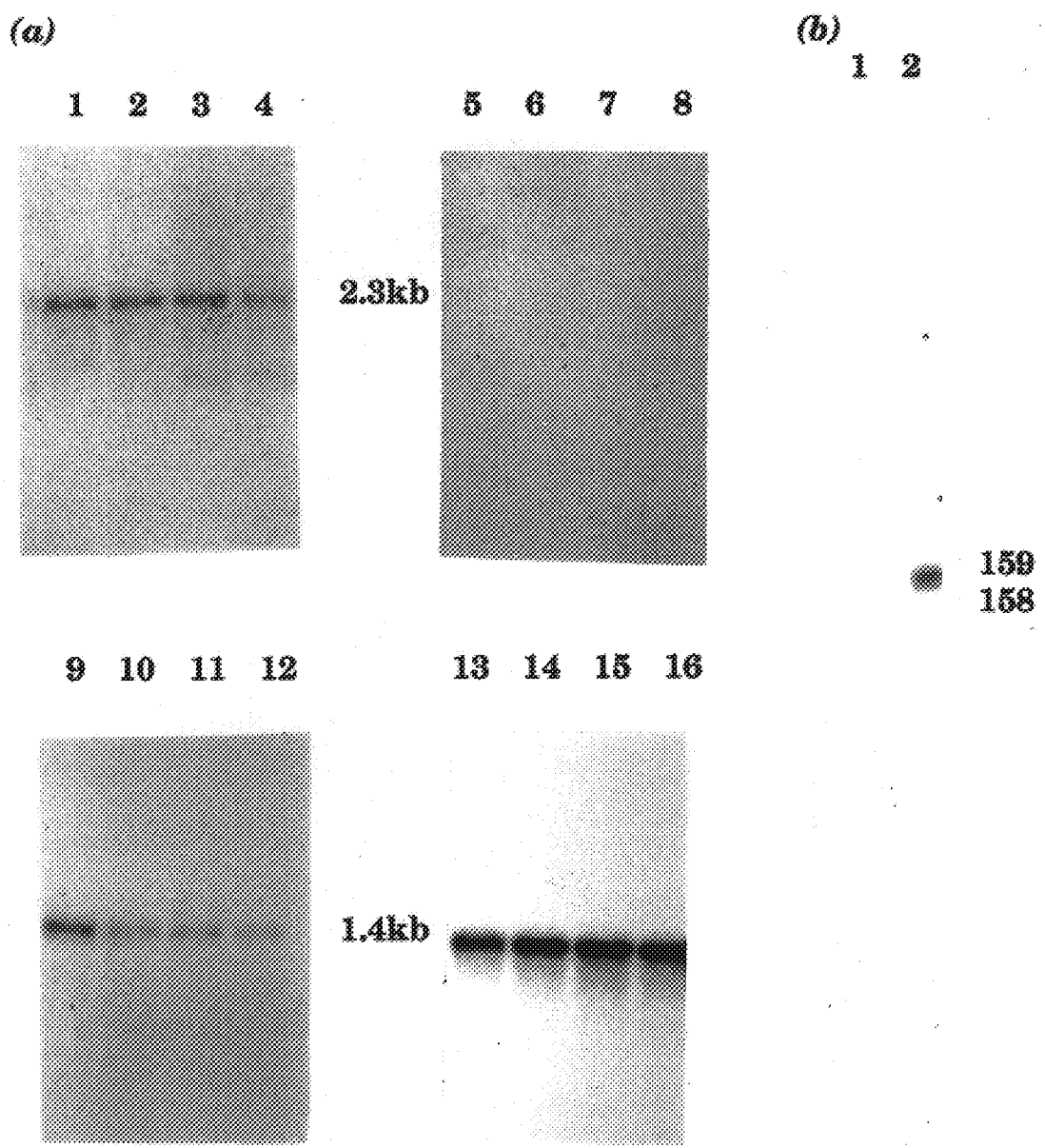
FIG. 5(a) shows the results of northern blot hybridizations.
FIG. 5(b) shows the results of primer extension on total RNA from B10.L-Lsh macrophages.

FIG. 5 shows that Nramp transcripts encoding the additional 64 amino acids are the only form of Nramp expressed in the macrophage.

Referring to FIG. 5(a), to identify the nature of Nramp expressed within the macrophage, Northern blot hybridizations were performed with total RNA isolated from resting macrophages (lanes 1,5,9,13), or macrophages activated with interferon-γ (lanes 2,6,10,14), LPS (lanes 3,7,11,15), or interferon-γ plus LPS (lanes 4,8,12,16). Probes specific for unique λ8.1 5' sequence (lanes 1–4), or for the more distal putative 5' UTR of the published (Ref 2) sequence (lanes 5–8), were used and compared against the same blots reprobed with constitutively expressed GAPDH (lanes 9–16). Hybridizing RNAs could only be detected with the λ8.1-specific sequence, despite loading twice as much RNA on blots hybridised with the more distal probe. Results are shown for RNA extracted from bone marrow-derived macrophages from C57BL/10ScSn mice. Slot blot analysis (not shown) confirmed that the λ8.1-specific probe hybridized to RNA from both susceptible and resistant macrophages. Southern blot analysis (not shown) confirmed that both probes hybridized to EcoRI fragments of 3500 and 500 bp in mouse genomic DNA from both C57BL/10ScSn (Lsh$^s$) and B10.L-Lsh$^r$ mice.

Referring to FIG. 5 (b), to identify the 5' terminus of Nramp transcript expressed in macrophage RNA, primer extensions were performed with 10 μg of total RNA from B10.L-Lsh$^r$ macrophages using oligonucleotides specific to the putative 5' untranslated region of the published (Ref 2) sequence (lane 1), or to 5' sequence unique to λ8.1 (lane 2). The numbers of nucleotides from the 5' end of the primer are shown. Control reactions with tRNA gave no products with either primer. These experiments confirm that RNA transcripts bearing the putative 5' untranslated region of the published cDNA are not present in resting (not shown) or activated macrophages, whereas transcripts corresponding to the λ8.1 sequence were identified with transcriptional initiation sites mapping 21 and 22 bp (doublet) 5' of the proximal ATG codon. Similar results were obtained using RNA from C57BL/10ScSn (Lsh$^s$) macrophages as template.

FIG. 6 shows that macrophage Nramp encodes an N-terminal SH3 binding domain structure.

Amino acid database searches (Ref 29) with the 64 amino acid sequence unique to macrophage-expressed Nramp identified a number of sequence matches particularly with the proline rich sequence. Multiple sequence alignments allowed for the generation of a consensus motif over this region: PGPAPQPXPXR (solid vertical bar). Matches were found for three molecules involved in signal transduction: the focal adhesion kinase (Ref 20) (50% identity over 26 residues); Drosophila dynamin shibire protein (Ref 17) (55% identity over 20 residues); and the adenylate cyclase stimulatory beta-1-adrenergic receptor (Ref 19) (57% identity over 21 residues). A proline, serine rich domain has been identified as a functional SH3 binding domain in dynamin (Refs 17,3). The nine best matches were aligned with each other and residues boxed where four or more exhibited identities. Also shown are the two PKC sites (hatched vertical bars) on S3 and S37 which flank the region exhibiting sequence identity. Tyrosine residues (asterisk) occur on either side of the consensus motif indicating conservation of this part of the sequence.

FIG. 7 shows the nucleotide and deduced amino acid sequence of exon 2 of human NRAMP obtained from genomic sequence analysis.

Exon 2 in murine Nramp encodes the putative SH3 binding domain with amino acid matches to a number of signal transduction molecules. To characterise the structure of the same region of the human NRAMP gene, a yeast artificial chromosome hybridising to 2q35 was subcloned into EMBL3 and the resulting library screened by cross-species hybridisation using a murine \probe to identify clones containing this exon. Genomic sequence across exon 2 was obtained (FIG. 7), with splice donor and acceptor sites conforming to the GT AG boundaries as identified in the murine sequence.

FIG. 8 shows that N-terminal sequence for human NRAMP encodes an SH3 binding domain structure.

Analysis of the deduced amino acid sequence indicated that this exon of the human gene encodes 48 codons compared with 45 in the mouse, with many of the features of the murine deduced amino acid sequence maintained (FIG. 8). These include the distal consensus sequence for phosphorylation by PKC. Both tyrosine (Y) residues are maintained and share identical positions as murine Nramp, and the human exon 2 sequence is rich in serine (S 9/48 compared to 9/45 in mouse); proline (P 10/48 compared to 10/45 in mouse); and basic (5/48 compared to 5/45 in mouse) residues. Of these important residues, 6/9 S, 6/10 P, and 4/5 basic residues show identical positions within murine and human exon 2. The spacing of the prolines are subtly different in the consensus sequence for the SH3 binding domain of the human gene: at positions 1 4 7 9 13 14 compared with 1 3 5 7 9 in mouse. The human consensus motif over this region is: PXSPTSPXPXXAPPRXT (SEQ ID NO: 3). The 3 codon insertion in human exon 2 forms the 5' segment of this proline rich domain. This insertion region has an unusual nucleotide sequence consisting of an almost perfect 3 times 9 nucleotide repeat, representing a region of some instability and source of polymorphism in man (Ref 32) which could influence function. The presence of the extra 3 codon segment within the human gene sequence produced some additional amino acid sequence identities on screening databases. These include several proteins involved in cytoskeletal interactions or signal transduction pathways: microtubule associated protein 4; adenylyl associated protein; phospholipase C β3; phosphatidylinositol 3-kinase regulatory subunit p85μ (PI3-kinase p85α); ankyrin; and zyxin.

Computer-assisted analysis

Hydropathy profiles of the predicted N-terminal amino acid sequence of macrophage-expressed Nramp were obtained by computer-assisted analysis using the algorithm and hydropathy values of Kyte and Doolittle (Ref 14). Amino-acid sequence comparisons were made using the FASTA programme on-line to the CRC Resource Centre.

Results and Discussion

Sequence analysis of macrophage-derived Nramp cDNA clones. Screening an activated macrophage library yielded 15 full length Nramp cDNAs, 14 of which differed from the published (Ref 2) Nramp in the 5' terminal sequence. The longest macrophage-derived cDNA (FIG. 1; λ8.1) was 186 bp shorter than Nramp. It contained the full length coding region for the previously predicted protein, and exhibited 100% identity with no in frame stop codons for the region (bp 209–263) of untranslated sequence immediately 5' of the published initiation codon. However, nucleotides 1–208 of λ8.1 shared no identity with the published sequence. A more proximal ATG codon was identified at 72 bp in λ8.1, preceeded by an in frame stop codon at 36 bp. This proximal translational initiation codon is followed by an ORF of 192 bp (64 amino acids) that leads into the ORF previously reported. Previous studies have shown that proximal initiation codons are utilised in more than 90% of all genes analysed (Ref 15). Nor was there any evidence that the distal initiation codon would be favoured, since both distal and proximal initiation codons and flanking sequences are identical (TCCTCATGA) and display only two identities with the optimal (Ref 16) ($CC^A/_GCCATGG$) consensus. Hence, there is no a priori reason why the distal initiation codon would be used.

Genomic sequence for the 5' region of Nramp. To determine whether mechanisms exist which could generate two RNAs and hence two types of Nramp clones, a region of genomic DNA spanning the point of divergence was characterised corresponding to nucleotides 31–456 of λ8.1 (FIG. 2). This region is encoded by four exons interspersed by three introns of 395, 900 and 241 bp, with all splice donor and acceptor sites conforming to the GT and AG boundaries. The first 47 amino acids of the 64 amino acid N-terminal domain of λ8.1 are encoded by two proximal exons unique to this clone. The remaining 17 amino acids are encoded by exon three, with exons three and four common to both λ8.1 and the published (Ref 2) Nramp cDNA. The 5' UTR sequence from the published clone was found in the 900 bp intron contiguous with and including part of the third exon, indicating that a single gene encodes both forms. The third exon is particularly unusual in that it encodes protein sequence in λ8.1, whereas for the published Nramp sequence it contains both coding and non-coding sequence. Although a complex mechanism involving alternative splicing associated with an internal splice acceptor site and dual promoter control could be formulated to describe the origin of both forms, it seems more likely that the published (Ref 2) cDNA clone contains a fragment of the 900 bp intron at its proximal end. This is consistent with the observation that a number of the macrophage-derived Nramp clones isolated here were found to contain sequence that exhibited identity with the first Nramp intron identified in genomic DNA (not shown).

Only one form of Nramp is expressed in macrophages. To confirm the hypothesis that the RNA encoding the longer polypeptide is the form expressed in macrophages, a number of different experimental approaches were adopted (FIG. 3). Using macrophage RNA as template, primer extension with an oligonucleotide unique to the 5' region of λ8.1 yielded products in both susceptible and resistant mice. In direct contrast, no products were generated using an oligonucleotide within the putative 5' UTR of published (Ref 2) Nramp. A probe covering the 5' region unique to λ8.1 also hybridized well to Northern and slot blots of macrophage RNA from susceptible and resistant mice, whereas a probe covering the putative 5' UTR of the published clone showed no hybridization. Hence, the only form of RNA transcript present in macrophages is that which conforms to the λ8.1 predicted polypeptide sequence, suggesting that this form of the Nramp gene is responsible for host resistance.

Predicted structure and sequence identities across the N-terminus of macrophage-expressed Nramp. In order to determine how macrophage-expressed Nramp might relate to Lsh/Ity/Bcg gene function, hydropathy (Ref 14) plots and amino acid database searches were undertaken over the newly identified 64 amino acid domain. The former (data not shown) demonstrated that the new sequence is hydrophilic, and forms an extension to the N-terminal cytoplasmic domain. The amino acid database search over this proline, serine and basic rich 64 amino acid domain identified three PKC phosphorylation sites (in addition to the two identified in the published Nramp sequence), and a number of matches with several unrelated proteins (FIG. 4). The most intriguing matches were: (i) with the dynamin shibire protein (Ref 17) of Drosophila, related to mammalian dynamin (dephosphin) which acts as a synaptic phosphoprotein in rat brain (Ref 18); (ii) with the proline rich third cytoplasmic domain of the adenylate cyclase stimulatory and G protein coupled beta-1-adrenergic receptor (Ref 19); and (iii) with the focal adhesion kinase (Ref 20) that can be modulated by integrin-dependent phosphorylation (Ref 21). The region of identity with the C-terminal domain of dynamin has been implicated (Ref 22) in binding anionic phospholipids, microtubules and Src homology 3 (SH3) domains. SH3 domains (Refs 3,4), identified as related sequences in different tyrosine kinases (TK) but outside the catalytic domain, are modular and found in a number of proteins such as the non-receptor TKs, phospholipase C-gamma and other structural proteins of the cytoskeleton. Whilst the function of SH3 domains (Ref 4) is not as well characterised as the SH2 counterpart, it is believed they mediate specific protein-protein interactions obligatory for signal transduction (Ref 3). IL-2R beta (Ref 25) and erythropoietin (Ref 26) receptors, for example, exhibit serine and proline rich intracellular domains which associate with TKs mediating phosphorylation essential to receptor function. Members of the Src family of membrane-associated TKs, including Hck and Fgr, are also found in macrophages (Ref 27). Both exhibit differential kinetics in response to priming/activation signals and could be implicated in Nramp-mediated signal transduction pathways. Hck, in particular, has recently been shown to be involved in signal transduction for TNF-α production in murine macrophages (Ref 28), a step which we have demonstrated (Ref 11) is crucial in the pathway to enhanced nitric oxide production and antimicrobial activity in Lsh resistant macrophages.

In recent studies we have also demonstrated that interaction of resistant macrophages with integrins, cell surface molecules which mediate binding to extracellular matrix proteins and signal via TKs, is sufficient to stimulate enhanced TNF-α production in resistant but not susceptible macrophages (Ref 9). Overall, the multiple PKC phosphorylation sites on Nramp, together with the new SH3 binding domain identified here, provide compelling evidence that Nramp mediates resistance by controlling signal transduction for macrophage priming/activation.

N-terminal sequence analysis of human NRAMP supported the findings with murine Nramp in showing sequence identity over the putative SH3 binding domain with a series of proteins involved in cytoskeletal interactions or signal transduction pathways. Of these, PI3-kinase p85α (Ref 10) is of particular interest because it functions by binding to phosphorylated protein tyrosine kinase via SH2 domains (Ref 12), and acts as an adaptor mediating the association of the p110 catalytic unit to the plasma membrane. PI3-kinase p85α also has an SH3 domain. Ankyrin B (Ref 13) is a molecule linking integral membrane proteins to cytoskeletal elements, and zyxin (Ref 23), an adhesion plaque protein and a possible component of a signal transduction pathway mediating adhesion-associated gene expression. Overall, this evidence supports our earlier conclusion based on the putative SH3 binding domain of the murine gene that this domain is important in protein-protein interactions important in signal transduction, and/or protein interactions (e.g. binding of tyrosine kinases mediating phosphorylation on tyrosines) which regulate the transport function of the molecule.

Nramp gene transfer studies

A number of Nramp retroviral vector constructs were made, all based on the pBabe plasmid. These include the cDNAs encoding the predicted protein described above, together with a C-terminal deletion construct encoding the proximal 72 amino acids of the N-terminus. The former construct has been introduced by calcium phosphate-mediated co-precipitation into the gp+86 ecotropic packaging cell and recombinant clones selected for the linked marker gene which confers resistance to puromycin. A number of these resistant clones have been tested for their ability: (i) to secrete functional pseudovirus particles by RNA slot blotting and hybridisation with an Nramp probe; and (ii) to infect recipient cells and confer antibiotic resistance. Infectious particles from the highest titre lines will be used for in vivo gene transfer. This same construct has been introduced into a murine macrophage cell line (RAW 264) which expresses a different allelic ("Lsh susceptible") variant from that of the vector-derived Nramp gene.

Several clones have been identified that co-express both forms of Nramp as monitored by PCR followed by allele-specific oligonucleotide hybridisation. Functional experiments have been performed to demonstrate that Nramp is the disease resistance gene Ity/Lsh/fTcg, by demonstrating that the resistant allele confers macrophage activation phenotypes previously associated with the action of the Ity/Lsh/Bcg gene. More specifically:

Table 1 demonstrates that the Nramp resistant allele confers an enhanced baseline PMA-elicited respiratory burst response compared to the control susceptible transfectant clones. This resting PMA-elicited respiratory burst is completely extinguished in susceptible but not resistant transfectants following treatment of the macrophages with bacterial lipopolysaccharide (LPS). Respiratory burst products mediate antimicrobial and tumouricidal activity.

TABLE 1

| Transfectant | 24 hour resting cells | 24 hour LPS/IFNγ treated |
| --- | --- | --- |
| 10S | 0.155 ± 0.013 | 0.025 ± 0.006 |
| 25S | 0.181 ± 0.026 | 0.002 ± 0.003 |
| 30S | 0.147 ± 0.025 | 0.034 ± 0.008 |
| 7.1R | 0.296 ± 0.056* | 0.219 ± 0.022*** |
| 7.2R | 0.399 ± 0.077*** | 0.292 ± 0.029*** |
| 7.5R | 0.442 ± 0.080** | 0.181 ± 0.097* |
| 7.8R | 0.291 ± 0.019** | 0.364 ± 0.052*** |
| 7.11R | 0.290 ± 0.069** | 0.308 ± 0.036*** |
| 17.1R | 0.389 ± 0.082* | 0.272 ± 0.059** |
| 17.5R | 0.329 ± 0.056** | 0.230 ± 0.018*** |

Resistant allele RAW264.7 transfectants generate enhanced RB responses which are not extinguished following LPS stimulation. PMA-elicited RB was measured using a standard assay in which superoxide reduces nitro blue tetrazolium to formazan in (a) resting resistant and susceptible transfectants, and (b) after 24 or 30 hours incubation with LPS (25 ng/ml). To normalise for cell numbers, results are expressed as a ratio of formazan:crystal violet readings from 6-wells/treatment. Asterisks indicate significance levels (p < 0.05 = *; p < 0.01 = ; p < 0.001 = *) for results of student's t-tests used to compare each resistant transfectant against the susceptible transfectant 30S. Similar levels of significance were observed for comparisons with 10S and 25S. Results representative of 5 independent experiments performed.

Table 2 demonstrates that the Nramp resistant allele confers enhanced nitrite release following priming/ activation with LPS and interferon-γ (IFNγ). Nitrites are the stable end-product of nitric oxide generated by upregulated expression of the inducible nitric oxide synthase gene in resistant macrophages. Nitric oxide also mediates antimicrobial and tumouricidal activity, and is specifically known to be the final effector mechanism for antileishmanial and antimycobacterial activity in murine resistant macrophages.

TABLE 2

| Transfectant | LPS alone | LPS + IFNγ |
|---|---|---|
| 10S | 0.043 ± 0.008 | 0.296 ± 0.026 |
| 30S | 0.009 ± 0.008 | 0.274 ± 0.027 |
| 7.2R | 0.215 ± 0.005*** | 0.603 ± 0.059** |
| 7.5R | 0.256 ± 0.062*** | 0.857 ± 0.059*** |

Resistant allele RAW264.7 transfectants exhibit enhanced NO generation in response to LPS and/or IFN-γ stimulation. Nitrite release was measured as the stable endproduct of NO production using the Griess reagent. Cells were incubated for 24 or 30 hours in the presence of LPS (25 ng/ml) or LPS plus IFNy (25 ng/ml and 25 U/ml). Determinations were normalised to cell number from the crystal violet staining intensity of a parallel plate and results are presented as the ratio of nitrite to crystal violet. Asterisks indicate significance levels ($p < 0.05$ = *; $p < 0.01$ = ; $p < 0.001$ = *) for results of student's t-tests used to compare each resistant transfectant against the susceptible transfectants 10S and 30S. Clones 17.3R and 17.6R developed from an independent transfection also showed significantly ($p < 0.05$) higher NO levels in this experiment. Results representative of 5 independent experiments performed.

Table 3 demonstrates that the Nramp resistant allele confers enhanced L-arginine uptake following priming/activation with LPS and IFN-γ. L-arginine provides the substrate for generation of nitric oxide involved in signal transduction for upregulated expression of KC in resistant macrophages (Ref 24), and for the final effector mechanism for cidal activity of the macrophage.

TABLE 3

| Transfectant | Percent Enhancement |
|---|---|
| 2S | 108 ± 5 |
| 10S | 119 ± 10 |
| 30S | 122 ± 10 |
| 7.5R | 194 ± 24*** |
| 7.8R | 204 ± 40** |
| 17.1R | 168 ± 11* |
| 17.3R | 186 ± 5** |

L-arginine uptake is enhanced in resistant transfectants compared to susceptible following activation with LPS and IFNγ. L-arginine was measured over the 6 hours following stimulation with 25 U/ml IFNγ and 25 ng/ml LPS. The culture medium employed contained 0.4 mM L-arginine excluding any contribution from serum. Pilot experiments demonstrated that the uptake of [$^3$H] L-arginine (0.25 μCi, specific activity 58 Ci/mmol) from $10^5$ cells was linear over a one hour time period at 37° C. In all subsequent experiments cells were pulsed for 30–45 mins. The incubation was terminated by removing the media and washing the adherent cells 3 times in PBS containing 10 mM unlabelled L-arginine. Cells were lysed in 50 μl of 1% SDS and counted in 5 ml of aquasol II (DUPONT-NEN). Results are expressed as the percentage stimulation + standard deviation observed in 6 hour LPS ± IFNγ treated macrophages compared to untreated controls. Asterisks indicate significance levels ($p < 0.05$ = *; $p < 0.01$ = ; $p < 0.001$ = *) for results of student's t-tests used to compare each resistant transfectant against the susceptible transfectants 2S, 10S and 30S. Results representative of 5 independent experiments performed.

This demonstration that Nramp influences three independent pleiotropic effects of the gene previously associated with Ity/Lsh/Bcg function provides definitive evidence that Nramp is Ity/Lsh/Bcg.

In view of the similarities observed between murine/human Nramp/NRAMP and the yeast mitochondrial proteins SMF1 and SMF2, additional experiments have been performed to determine whether these Nramp regulated pleiotropic effects rely on intracellular signalling mediated by the generation of mitochondrially-derived reactive oxygen intermediates (ROI).

Table 4 demonstrates that respiratory burst and L-arginine uptake are inhibited in the presence of the mitochondrial electron transport inhibitors rotenone (0–40 μM; inhibits complex I→ubiquinone) or thenoyltrifluoroacetone (TTFA; 0–400 μM; inhibits complex II→ubiquinone). Concentrations of inhibitors were based on previous studies (Ref. 61) examining the role of mitochondrially-derived ROI on apoptosis and the gene-inductive effects of TNFa in fibroblasts, and were not observed to have toxic effects on the RAW264.7-derived transfectant lines.

TABLE 4

| Rotenone Concentration (μM) | L-arginine uptake | RB |
|---|---|---|
| 0 | 100 | 100 |
| 5 | 66 ± 16 | 52 ± 3.7 |
| 10 | 79 ± 17 | 33 ± 4.4 |
| 20 | 73 ± 7 | 16 ± 5.4 |
| 40 | 74 ± 11 | 11 ± 3.7 |

L-arginine uptake experiments were performed in the presence of the radical scavengers nordihydroguaiaretic acid (0–40 μM) and butylated hydroxyanisole (0–400 μM). Respiratory burst and L-arginine uptake experiments were also carried out in the presence of the mitochondrial electron transport inhibitors rotenone (0–40 μM; inhibits complex I → ubiquinone) or thenoyl-trifluoroacetone (TTFA; 0–400 μM; inhibits complex II → ubiquinone) . Cells were allowed to adhere to microtitre wells for 1 hour prior to a 1 hour pretreatment with drugs before addition of activation agents for appropriate time periods. Results are presented for rotenone inhibition (percent of control) of L-arginine and RB for the resistant transfectant clone 7.5R examined after treatment with LPS/IFNγ.

These findings imply a role for Nramp in regulating mitochondrial function and the generation of reactive oxygen intermediates for signalling. Thus there are two ways in which Nramp may influence intracellular signalling for macrophage activation: (i) by influencing the generation of reactive oxygen intermediates from the mitochondrion; and (ii) by enhanced generation of nitric oxide. These studies of Nramp gene function bring together the decade of functional work demonstrating that Nramp regulates macrophage priming/activation for antimicrobial activity, with the many pleiotropic effects of the gene due to its role in regulating cell signalling events. The crucial significance of the putative SH3 binding domain in the function of the Nramp gene is that it regulates its function in response to priming/activation signals.

Nramp protein and antibody production

On the basis of hydropathy plots the applicants have selected two structural domains that are not hidden by membrane and therefore are likely to be accessible within the intact/native protein conformation. Oligonucleotide primers to these two domains (N-terminal amino acids 1–82, C-terminal amino acids 514–548) were generated with restriction sites allowing the amplified products to be cloned in the appropriate reading frame in the pGEX series of prokaryotic expression vectors. The Nramp sequences are ligated downstream of a glutathione-S-transferase gene from Schistosoma japonicum under control of an inducible tac promoter enabling the induction of high level expression of fusion proteins that can be easily purified from bacterial lysates by affinity chromatography using glutathione agarose. Bound proteins can be released from the matrix under mild conditions such that the native conformation is maintained to improve antigenicity. This system has been employed to generate Nramp proteins of approximately 8.2 and 3.4 kd. from the N-terminal and C-terminal regions respectively, which have been used as antigens with the RIBI adjuvant to innoculate rabbits for production of polyclonal antibodies and rats for production of monoclonal antibodies. In order to ensure that antibodies raised will be specific to both murine and human Nramp/NRAMP proteins, these antibodies should be screened or affinity purified against peptides prepared on the basis of sequence information across these N-terminal and C-terminal regions used for production of the fusion protein. Specifically, against peptides DKSPPRLSRPSYGSISS (SEQ ID NO: 12); PQPAPCRETYLSEKIPIP (SEQ ID NO: 13); and GTF-SLRKLWAFTGPGFLMSIAFLDPGNIESDLQ (SEQ ID NO: 14) within the N-terminal region, and WTCCIAHGAT-FLTHSSHKHFLYGL (SEQ ID NO: 15) in the C-terminal region.

Genomic Organization and Sequence of Human NRAMP gene (Ref 62)

Genomic sequencing of NRAMP. A human yeast artificial chromosome (YAC) AM11/D3/14 (Ref 30), obtained from the ICRF library (available through the UK Human Gene Mapping Project HGMP Resource Centre, Huxton Hill, Cambridge CB10 1RQ, UK) by screening with a VIL1 probe (Ref 31) and containing the entire human NRAMP sequence (Ref 32), was subcloned into λEMBL3 (Stratagene Ltd, Cambridge, UK) and screened with the full-length murine Nramp cDNA λ8.1 (Ref 55). Two overlapping clones, λ3 and λB1, containing the full-length NRAMP sequence, were digested with PstI, subcloned into pBluescript II SK (Stratagene Ltd), and re-screened with the full-length murine cDNA probe (Ref 55). Exon positive clones were selected for sequence analysis, with gaps being filled by sequencing fragments prepared by PCR between identified exons. Exons were identified by comparison of human genomic sequence with mouse (Refs 2, 55) or human cDNA sequences. Human cDNA sequence was obtained by reverse transcription (RT) and PCR amplification of RNA prepared from the human monocyte-derived THP1 cell line (Ref 33). Where appropriate, PCR products were cloned into the pCR vector (Invitrogen Corporation, Abingdon, UK) for sequence analysis from at least 2 independent clones. Clones corresponding to the 3' region were not originally isolated by screening with the murine CDNA. A fragment was generated by 3' rapid amplification of cDNA ends (RACE; (Ref 34)) from polydT adaptor primed THP1 cDNA. cDNA was amplified using the adaptor primer in combination with 2 nested primers selected from exon 13 (GTGCTGCCCATCCTCACG (SEQ ID NO: 18); GAGTTTGCCAATGGCCTG (SEQ ID NO: 19)). A suitable genomic clone was prepared by amplification of a fragment from both λ3 and the YAC AM11/D3/14 using exon 13 primers and a primer (GGACGAGAAGGGAACTAG (SEQ ID NO: 20)) designed from the 3' end of the RACE product. The 5' end of the RNA was mapped by 5' RACE involving RNA ligase-dependent ligation of a blocked anchor primer to the 3' end of random hexamer primed reverse transcribed THP1 RNA. Amplification using an anchor primer and two NRAMP-specific nested antisense primers (AAGAAGGTGTCCACAATGGTG (SEQ ID NO: 21), CGGTTTTGTGTCTGGGAT (SEQ ID NO: 22)) yielded a single NRAMP product. The product was TA cloned and 3 clones subjected to sequence analysis to determine the transcriptional initiation site and sequence of the most proximal exon that failed to hybridise to any mouse cDNA probe. This facilitated further analysis of the 5' flanking region, the sequence for which was obtained from a 1.6 kb PstI fragment that contained sequence homologous to the 5' RACE product.

Analysis of sequence data. Nucleotide and amino acid sequence comparisons were made using the BESTFIT programme on-line to the CRC Resource Centre, UK. Amino acid sequences for murine and human NRAMP were aligned with yeast SMF1 and SMF2 (Ref 35) using the multiple sequence alignment program Clustal V (Ref 36).

Direct cycle sequencing across exons 4–6 of human NRAMP. Primers (GACAGGCAAGGACTTGGGT (SEQ ID NO: 23) and AAGAAGGTGTCCACAATGGTG (SEQ ID NO: 24)) were designed for RT/PCR amplification of a 200 bp product between exons 4 and 6 of human NRAMP, using RNA purified from peripheral blood mononuclear cells. This product spans the region of murine Nramp which carries the susceptibility mutation. PCR products were purified with a Qiagen PCR purification kit (Hybaid Ltd, Teddington, UK), and subjected to direct cycle sequence analysis using the CircumVent Thermal Cycle Dideoxy DNA Sequencing Kit (New England Biolabs, CP Laboratories, Bishop's Stortford, UK) with an internal sequencing primer (CATCTCTACTACCCCAAGGTGC (SEQ ID NO: 25)). Direct cycle sequence analysis was performed on 19 individuals: 8 visceral leishmaniasis patients, 9 unaffected individuals taken from the same families, and 2 nonendemic British controls. Endemic samples were from Brazil (4 affecteds; 5 unaffecteds) and the Sudan (4 affecteds; 4 unaffecteds). Primer design and PCR analysis of a 5' gt repeat using human genomic DNAs. PCR products of 780–794 bp were amplified from genomic DNA using primers located −365 bp 5' of the transcription start site (GAGGGGTCTTGGAACTCCA (SEQ ID NO: 26)) and within intron 1 (CACCTTCTCCGGCAGCCC (SEQ ID NO: 27)). This product was reamplified to generate 108–122 bp products using the 5' primer and an end-labelled ($\gamma^{32}$PdATP; ICN Biomedicals Ltd, Thame, UK) internal reverse primer TACCCCATGACCACACCC (SEQ ID NO: 28). The products were resolved by denaturing polyacrylamide gel electrophoresis and sized using a sequencing ladder. PCR products corresponding to different allelic forms were directly sequenced as described above.

Family linkage studies. A set of 36 multicase families of leprosy, tuberculosis and visceral leishmaniasis from our study site in Brazil (ref 37) were used to determine linkage between a polymorphic gt repeat in the 5' promoter region of human NRAMP and previously mapped 2q34–q35 markers (Refs 32, 37). Two-point linkage analyses were carried out between NRAMP and the markers (TNP1, IL8RB, VIL1, DES) using LINKAGE (Ref 38) on-line to the CRC Resource Centre. Gene frequencies for the NRAMP alleles were calculated from a sample of 72 genetically independent individuals from the Brazilian study site.

Results

Referring to FIG. 9, Clustal V multiple sequence alignment is shown for the deduced amino acid sequence for human NRAMP, murine Nramp clone λ8.1 (Ref 55), and the yeast mitochondrial proteins SMF1 and SMF2 (Ref 35). Residues showing 3/4 or 4/4 identities across the 4 proteins are shown in bold. For the NRAMP sequence: exon boundaries are indicated above the sequence; PKC indicates consensus sites (S/T-X-R/K) for protein kinase C phosphorylation; ===indicates consensus sites for N-linked glycosylation; and putative membrane spanning domains ((Ref 2) are overlined and numbered on the sequence. * indicates cysteine residues conserved across all 4 proteins; . indicates conserved substitutions.

Referring to FIG. 10(A), results of amino acid database searches for exon 2 are shown identifying a number of sequence matches with the Pro/Ser rich putative SH3 binding domain of NRAMP; +represents a conserved amino acid. Residues showing 4 or more identities are in bold.

Multiple sequence alignments allowed for the generation of a consensus motif over this region as shown by double underlining. Also shown is the PKC site on S40, and tyrosine residues (*) on either side of the consensus motif. In FIG. 10(B), Clustal V multiple sequence alignment is shown for human NRAMP, mouse Nramp, SMF1 and SMF2, and the expressed sequence tags (Ref 60) of Oryza sativa (rice; accession number d15268) and Arabidopsis thaliana (accession number z30530) genes, reading frames 1 and 2 respectively. Residues showing >4/6 identities across the 6 proteins are in bold. Membrane spanning domains 6 and 7 for NRAMP are overlined and numbered on the sequence. The 20 amino acid conserved transport motif (Ref 2) is indicated by double overlining. All 6 proteins show identities (similarities) of 7/20 (11/20) across the transport motif. * indicates cysteine residues conserved across all 6 proteins; . indicates conserved substitutions.

Referring to FIG. 11, there is shown 440 bp of putative promoter region human NRAMP sequence 5' of the transcription start site. The transcription start site is located 148 bp 5' of the ATG initiation codon, as indicated. Putative promoter region elements identified by inspection (indicated above the sequence) include: a possible Z-DNA forming dinucleotide repeat $t(gt)_5ac(gt)_5ac(gt)_9g$; 6 interferon-γ response elements; 3 W-elements; 1 AP1 site; 3 NFκB binding sites; and 9 purine-rich GGAA core motifs (2 on the antisense strand) for the myeloid-specific PU.1 transcription factor, two of which combine with imperfect AP1-like sites to create PEA-3 consensus motifs. Strings of heat shock transcription factor (HSTF) motifs (NGAAN or NTTCN) also occur across the 440 bp sequence (not marked).

Figure 12:
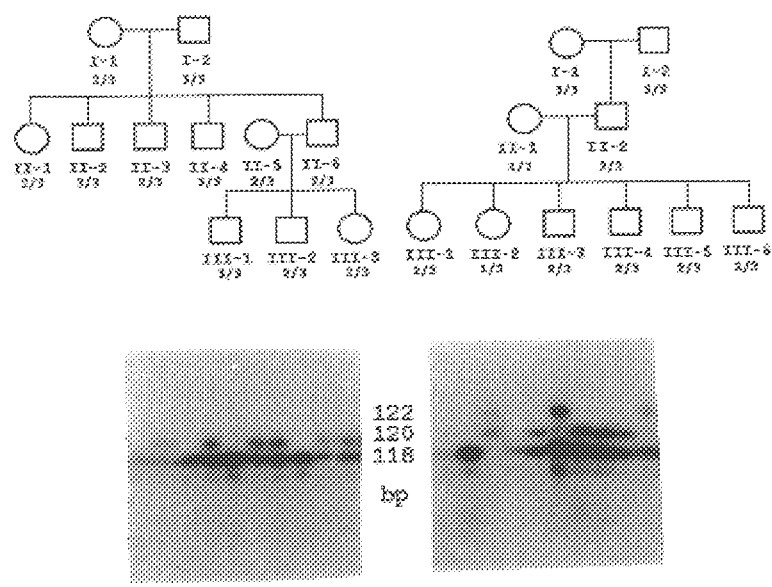
FIG. 12 shows two families segregating for (a) alleles 2 and 3, or (b) alleles 1, 2 and 3 of the 5' dinucleotide repeat polymorphism and autoradiographs of polymorphic PCR products separated by denaturing polyacrylamide gel electrophoresis.

Referring to FIG. 12, two families are shown regregating for (a) alleles 2 and 3, or (b) alleles 1, 2 and 3 of the 5' dinucleotide repeat polymorphism. Photographs below the families show autoradiographs of polymorphic PCR products (122 bp, 120 bp, and 118 bp for alleles 1 to 3, respectively) separated by denaturing polyacrylamide gel electrophoresis. Lanes from left to right on each photograph show individuals (a) I-2, II-1, II-2, II-3, II-4, II-5, II-6, III-1, III-2, III-3; and (b) I-1, I-2, II-1, II-2, III-1, III-2, III-3, III-4, III-5, III-6 as indicated on the pedigrees. Individual I-1 is not shown for family (a)

Sequence and genomic organization of human NRAMP. The sequencing of exon positive clones isolated by hybridization with a full-length cDNA allowed for the identification of the complete sequence (deposited with EMBL under accession numbers X82015 and X82016) of the human 2q homologue (NRAMP) of the murine chromosome 1 derived Nramp gene. Analysis of exon sequence from a region 440 bp 5' of the transcriptional initiation site to the termination codon allowed for the complete exon-intron organization to be elucidated (Tables 5 and 6). Human NRAMP is encoded by 15 exons and, in constrast to the 548 amino acid murine macrophage isoform (Ref 55), contains 550 amino acids (FIG. 9). This 550 amino acid polypeptide is initiated from a translational codon within exon 1 in the context of a weak (1/6) Kozak (Ref 16) consensus. The next, more distal codon found at M68 has a 2/6 Kozak consensus. However, we propose that like the murine macrophage form (Ref 55), the more proximal initiation codon will be utilised. This is reinforced by the striking (100%) sequence conservation for residues 51–67 (FIG. 9), indicating a requirement for the maintenance of sequence for function. The discrepancy in size between murine (548) and human (550) genes results from the inclusion of 3 additional residues within exon 2 causing a PTS duplication, with the non-duplicated form representing a rare variant in Brazilian (Ref 32) and British (unpublished data) pedigrees. In addition, the human gene exhibits a single amino acid deletion relative to the mouse within the poorly conserved last exon. Overall amino acid identity with murine Nramp was 86% (92% with conserved substitutions). Exons exhibiting highest sequence identity (100%) include exons 4, 6 and 7, with exon 11 displaying 98% identity. These exons encode TM1, the first extracellular domain, TM2 and TM3, and the conserved transport motif. It is of interest that TM2, containing the murine susceptibility-associated mutation (Refs 2, 56) is well conserved, suggesting that this domain plays an important functional role which cannot tolerate amino acid substitutions. NRAMP was aligned with murine Nramp and with the two yeast mitochondrial membrane proteins, SMF1 and SMF2, using the multiple sequence alignment program Clustal V (FIG. 9). SMF1 and SMF2, which show 49% identity (70% similarity) with each other, show 30% (57%) and 29% (53%) identities (similarities) with human NRAMP, respectively. This parallels the 30% (58%) and 30% (53%) identities (similarities) we reported (Ref 57) for murine Nramp. Regions of most striking sequence identity between all 4 proteins were found predominantly within the hydrophobic regions, although high identities were also found in exons 3, 4, 5 and 6, and for the conserved transport motif from exon 11. Within exon 6, the YAC-derived amino-acid human sequence exhibited a Gly at residue 172, corresponding to the position of the Gly→Asp susceptibility mutation at codon 169 of the murine sequence. Although the two SMF genes do not encode a similar Gly, they encode residues that do not introduce negatively charged residues found in the susceptible allele of mice. As before (Refs 55, 32), matches with other proteins (FIG. 10) in the sequence databases were observed over exon 2 which contains a putative SH3 binding domain; and over the region of exon 11 containing the conserved binding-protein-dependent transport motif (Ref 2). The latter was highly conserved (7/20 identity; 11/20 similarity) in murine/human NRAMP, the yeast proteins, and in two expressed sequence tags from Oryza sativa (rice) and Arabidopsis thaliana. SMF1 and SMF2 do not demonstrate high identity over the proline/serine rich sequence of exon 2, but do have consensus (S/T-X-R/K) sequences (one in SMF1; two in SMF2) for PKC-dependent phosphorylation. Human NRAMP has two PKC consensus sites (in exons 2 and 3, FIG. 9) in this region, compared to three in the murine gene. The location of the distal site in SMF2 matches precisely with human NRAMP site 2/murine Nramp site 3, whereas the site in SMF1 is located 8 residues upstream. A pair of cysteine residues are conserved in all four genes: (i) in the first extracellular loop domain; and (2) in the third extracellular domain which also contains two sites for N-linked glycosylation in the human and murine genes. Charged residues are conserved across all 4 proteins within the transmembrane spanning domains 1,2,3,4, and 7 (FIG. 9), except for a Lys-Ser substitution in the first transmembrane domain of SMF1.

Analysis of the murine mutation site in visceral leishmaniasis patients and controls. To determine whether a mutation homologous to the murine disease susceptibility Gly→Asp mutation occurs in man, RT/PCR and direct cycle sequencing was performed on RNA from visceral leishmaniasis patients and controls from Brazil and the Sudan. All 19 human samples, whether from affected or unaffected individuals, encoded a Gly at this position.

Analysis of the 5' promoter region of human NRAMP. A 1654 bp PstI fragment subcloned from λB1 contained exons 1 and 2, and also provided 440 bp of sequence 5' of the transcription start site (FIG. 11). The transcription start site is located 148 bp 5' of the ATG initiation codon. A series of predicted promoter region elements also occur 5' of the transcription start site, including a possible Z-DNA forming (Refs 39, 40) dinucleotide repeat t(gt)$_5$ac(gt)$_5$ac(gt)$_9$g (SEQ ID NO: 29), located −317 to −274 bp 5' of the transcription start site. On either side of the Z-DNA forming dinucleotide repeat are a series of matches to inducible promoter element consensus sequences. These include: 6 interferon-γ response elements, 1×3'→5' showing 8/8 matches to the consensus sequence CT$^G/_T^G/_T$ANN$^C/_T$ (Refs 41, 42), 3×5'→3' showing 7/8 matches, 2×3'→5' showing 7/8 matches; 3 W-elements (also known as H-, E-, W-, S-, or Z-boxes), 1×3'→5' showing 8/8 matches to the consensus sequence $^A/_T$GNA$^C/_A$C$^C/_T^G/_T$ (Ref 41), 2×5'→3' with 7/8 matches; an AP1 site showing 6/7 matches to the consensus sequence TGACTCA (Ref 43); and 3 NFκB binding sites, 2×5'→3' and 1×3'→5', each showing 7/10 matches to the consensus sequence GGG$^G/_A^C/A/_T$T$^C/_T^C/_T$CC (SEQ ID NO: 30)(Ref 44). Nine purine-rich GGAA core motifs (2 on the antisense strand) for the myeloid-specific PU.1 transcription factor (Refs 45, 46) also occur across this region, two of which combine with imperfect AP1-like sites to create PEA3 motifs (Ref 47), and another two are juxtaposed. Strings of heat shock transcription factor (HSTF) motifs NGAAN or NTTCN; (Ref 48) were also present, although their order and phase are not consistent with currently functional elements. TATA, GC and CCAAT boxes were not found within the 440 bp 5' flanking sequence.

Mapping of a polymorphic repeat in the 5' promoter region. The presence of a gt repeat in the 5' region of the YAC-derived NRAMP sequence stimulated further analysis of this region to determine whether a polymorphism was present in human population samples. Four alleles were observed in Brazilian families (FIG. 12): allele 1=122 bp; allele 2=120 bp; allele 3=118 bp; and allele 4=108 bp. Direct sequence analysis confirmed that the polymorphism was located in the largest cluster of gt repeats. Hence, allele 1=t(gt)$_5$ac(gt)$_5$ac(gt)$_{11}$g (SEQ ID NO: 31); allele 2=t(gt)$_5$ac (gt)$_5$ac(gt)$_{10}$g (SEQ ID NO: 32), allele 3=t(gt)$_5$ac(gt)$_5$ac(gt)$_9$g (SEQ ID NO: 29); and allele 4=t(gt)$_5$ac(gt)$_5$ac(gt)$_4$g (SEQ ID NO: 33). Gene frequencies determined on 72 genetically independent Brazilians were 0.021 (allele 1), 0.326 (allele 2), 0.646 (allele 3), and 0.007 (allele 4), providing an overall heterozygosity score of 0.476. Linkage analysis generated positive (>3) LOD scores (Table 7) for linkage between NRAMP and the four closest markers TNP1 (proximal) and IL8RB, VIL1, and DES (distal), consistent with physical mapping data (Ref 32) placing NRAMP 130 kb proximal to IL8RB, and confirming that this particular polymorphism occurs in the 2q35 copy of NRAMP rather than in a related sequence (Ref 49) mapping to a region in mice homologous to 6q27 in man.

Discussion

Genomic sequence analysis presented here demonstrates that the human NRAMP gene located on chromosome 2q35 has a genomic size of 12 kb and contains 15 exons. The amino acid sequence deduced from nucleotide sequencing of the 15 exons shows that, like murine Nramp, NRAMP encodes a polytopic integral membrane protein containing both a conserved transport motif (Ref 2) and a putative SH3 binding domain (Ref 55). Over the 20 amino acid transport motif, strong sequence identity (7/20 residues; 11/20 with conserved substitutions) was observed between NRAMP (Nramp), the two yeast proteins SMF1/2, and the expressed sequence tags from rice and Arabidopsis, suggesting that this is a functionally important motif among phylogenetically distinct organisms. Interestingly, these identities are higher than those reported (4/20 identity; 6/20 similarity) between murine Nramp and the nitrate transporter of *Aspergillus nidulans*, which led Vidal and coworkers (Ref 2) to hypothesise that Nramp might function in direct delivery of nitrates into the phagolysosomes of infected macrophages. The stronger identity observed here between the transport motif of NRAMP and the yeast mitochondrial proteins SMF1/2, together with the striking overall similarity between the yeast and human/murine genes, suggests that NRAMP may be a functional homologue to the yeast mitochondrial genes. The yeast genes encode hydrophobic molecules that influence processing enhancing protein-dependent protein import into mitochondria, possibly at the level of translocation (Ref 35). Complementation experiments with yeast mutants might therefore reveal more about the molecular mechanism of Nramp function. Sequence similarity between NRAMP(Nramp) and SMF1/2 was poor over the proline/serine rich putative SH3 binding domain. This is perhaps not unexpected as these are modular structures that occur in a variety of otherwise unrelated proteins involved in signalling and/or cytoskeletal attachment (Ref 55). Hence, this modular motif may be a recent addition to the NRAMP molecule related to its macrophage-restricted function, and we might expect that other more ubiquitously expressed NRAMP-like molecules will occur. A second Nramp-related sequence has already been mapped in the mouse (Ref 49), and others may be found.

Our major interest in analysing the human NRAMP gene was to provide the basis to screening multicase families for mycobacterial (tuberculosis and leprosy) and leishmanial infections. As a first step, we examined a small group of visceral leishmaniasis patients and their unaffected sibs to see whether a mutation similar to the murine susceptibility-associated mutation (Refs 2, 56) could be found. As might have been predicted, exon 6 encoding the second membrane spanning domain is highly conserved between murine and human sequences, as well as with the yeast genes, suggesting that this is a functionally important domain. No mutations were found within this region in the 19 human samples examined by direct cycle sequencing. Similarly, a polymorphic variant identified by us (Ref 32) in the putative SH3 binding domain occurred at very low frequency, suggesting that this too might be a region of the macrophage-expressed NRAMP molecule which, although recently acquired in evolutionary terms, may be critical to its function and intolerant to non-conservative substitutions.

The 440 bp of promoter region sequence identified here is of particular interest with respect to macrophage-restricted expression of the NRAMP gene, and provides a different approach to analysing polymorphisms which might influence expression rather than cause structural changes to the molecule. Identification of PU.1 and PEA3/AP1-like response elements is consistent with haematopoietic-restricted gene expression (Refs 47, 50, 51). Although earlier studies (Refs 2, 55) suggest that murine Nramp is constitutively expressed in macrophages, the inducible promoter region elements identified in the human sequence suggest that expression may be regulated by macrophage priming/activation stimuli. In particular, interferon-γ and W-elements are common to other genes (e.g. MHC class II, (Ref 41); FcγRI (Ref 42); iNOS (Ref 52) inducible in macrophages. AP1 and NFκB sites also occur in the promoter regions of other macrophage-expressed proteins (e.g. tissue factor (Ref 43); iNOS (Ref 52) and are required for LPS and TNF inducibility, AP1 acting to stabilise and maintain NFκB activity (Ref 43). Given the many functional observations (reviewed in Refs 1, 57–59) demonstrating that the Ity/Lsh/Bcg (candidate Nramp) phenotype is so closely allied to the interferon-γ/LPS macrophage activation pathway, it will be important to determine the functional relevance of these elements to tissue-specific expression of NRAMP in different macrophage subpopulations. This may be particularly relevant to previous observations demonstrating that the Lsh gene phenotype is differentially expressed in different macrophage subpopulations (Refs 53, 54), and that interaction with extracellular matrix elicits different levels of TNFα in bone marrow-derived macrophages from congenic resistant and susceptible mice (Ref 9). Although their order and phase were not consistent with currently functional elements, it was of interest that strings of HSTF elements were also found in the promoter region of human NRAMP. These may represent ancestral elements related to the mitochondrial activity/expression of the yeast SMF1 and SMF2 genes.

Another interesting feature of the 5' flanking region of human NRAMP was the presence of a putative Z-DNA forming dinucleotide repeat t(gt)$_5$ac(gt)$_5$ac(gt)$_n$g. A distinct class of binding proteins exists in eukaryotes which interact exclusively with DNA in the Z-conformation, and roles in both positive and negative regulatory signalling have been attributed to this form of DNA (reviewed Ref 39). It was particularly intriguing that a polymorphism in this repeat unit was observed in human genomic DNA samples. The fact that the putative Z-DNA forming repeat is flanked on either side by other promoter region response elements suggests that this polymorphism may be functionally important in determining gene expression, if not on the basis of its own role as a transcriptional regulator, at least because it will influence the juxtaposition of other response elements. The level of heterozygosity (0.476) in the Brazilian population studied here made this a useful marker for genetic linkage analysis between NRAMP and other 2q markers. However, the number of alleles was small compared to other repeat (e.g. microsatellite) polymorphisms, suggesting that the generation of further polymorphic variants across this repeat may not be tolerated in evolutionary terms. This polymorphism may therefore be of functional relevance in further analysis of the association between NRAMP and disease.

TABLES 5 and 6

Intron (4 flanking nucleotides)/exon(amino acids) boundaries and sizes (bp) for the 15 exons of human NRAMP identified by genomic sequence analysis of YAC-derived clones. Amino acid sequence identify with murine Nramp is shown for each exon.

TABLE 5

| Exon Number | Size (bp) | | Intron/exon boundaries | | | | | | % AA Identity (Mouse) |
|---|---|---|---|---|---|---|---|---|---|
| | | | | | Met | Thr | G | | 50 |
| EXON 1 | 155 | | | ATG | ..145bp.. | ATG | ACA | G | gtga | |
| | | | ly Asp | Lys | ..(43aa).. | Lys | Pro | | | 68 |
| EXON 2 | 143 | acag | GT GAC | AAG | .......... | AAA | CCG | | gtgg | |
| | | | Gly | Thr | ..(37aa).. | Phe | Lys | | | 95 |
| EXON 3 | 123 | acag | GGC | ACC | .......... | TTC | AAA | | gtaa | |
| | | | Leu | Leu | ..(36aa).. | Pro | Lys | | | 100 |
| EXON 4 | 120 | acag | CTT | CTC | .......... | CCT | AAG | | gtgg | |
| | | | Val | Pro | ..(31aa).. | Ala | Gly | Ar | | 91 |
| EXON 5 | 107 | tcag | GTG | CCC | .......... | GCT | GGA | CG | gtac | |
| | | | g Ile | Pro | ..(19aa).. | Asn | Tyr | G | | 100 |
| EXON 6 | 71 | tcag | A ATC | CCA | .......... | AAC | TAC | G | gtgg | |
| | | | ly Leu | Arg | ..(18aa).. | Tyr | Gln | | | 100 |
| EXON 7 | 68 | gtag | GG CTG | CGG | .......... | TAT | GAG | | gtag | |
| | | | Tyr | Val | ..(48aa).. | Val | Lys | | | 88 |
| EXON 8 | 156 | gcag | TAT | GTG | .......... | GTC | AAG | | gtag | |
| | | | Ser | Arg | ..(49aa).. | Ala | Ala | | | 87 |
| EXON 9 | 159 | gtag | TCT | CGA | .......... | GCT | GCG | | gtga | |
| | | | Phe | Asn | ..(26aa).. | Gln | Gly | | | 80 |
| EXON 10 | 90 | gcag | TTC | AAC | .......... | CAG | GGG | | gtga | |
| | | | Gly | Val | ..(36aa).. | Met | Glu | | | 98 |
| EXON 11 | 120 | gcag | GGC | GTG | .......... | ATG | GAG | | gtag | |
| | | | Gly | Phe | ..(46aa).. | Leu | Leu | | | 94 |
| EXON 12 | 150 | ccag | GGC | TTC | .......... | CTG | CTG | | gtag | |
| | | | Leu | Pro | ..(20aa).. | Asn | Gly | Le | | 84 |
| EXON 13 | 74 | ccag | CTC | CCG | .......... | AAT | GGC | CT | gtga | |
| | | | u Leu | Asn | ..(47aa).. | Tyr | Leu | | | 73 |
| EXON 14 | 154 | ccag | G CTG | AAC | .......... | TAC | CTG | | gtac | |
| | | | Val | Trp | ..(34aa).. | Ter | | | | 67 |
| EXON 15 | 108 | ccag | GTC | TGG | .......... | TAG | | | | |

TABLE 6

OVERLINED SEQUENCES REPRESENT REGIONS SELECTED FOR PRIMERS TO
AMPLIFY INDIVIDUAL EXONS.

EXON 1 (SEQ ID NO:34)
A T G T A A G A G G C A G G G C A C T C G G C T G C G G A T G G G T A A C A G G G C G T G G G C T G G C A C A C T T A C T T
G C A C C A G T G C C C A G A G A G G G G G T G C A G G C T G A G G A G C T G C C C A G A G C A C C G C T C A C A C T C C C
                                                                      M      T
A G A G T A C C T G A A G T C G G C A T T T C A A T G A C A Gg t g a g t a g t g g c c c c t a g g g a c a g a g c c t g a
t t g g g g g g t g g a g t g g a g g a g a t c a c t a g g c t g g t g g a g a c t t g a g g a a g c a a g a a a g c c c t
t g g t c c c c g t g

EXON 2 AMPLIFIED REGION (SEQ ID NO: 35)
                                                G    D    K    G    P    Q    R    L    S    G    S    S
t c a c c a t g c t t c a t g g g c c c c c a c a g GT G A C A A G G G T C C C C A A A G G C T A A G C G G G T C C A G C T
Y    G    S    I    S    S    P    T    S    P    T    S    P    G    P    Q    A    P    P    R
A T G G T T C C A T C T C C A G C C C G A C C A G C C C G A C C A G C C C A G G G C C A C A G C A A G C A C C T C C C A G A
E    T    Y    L    S    E    K    I    P    I    P    D    T    K    P
G A G A C C T A C C T G A G T G A G A A G A T C C C C A T C C C A G A C A C A A A A C Gg t g g g a c n c t g g a a a c t
t t c t g g g g g c t

EXON 3 AMPLIFIED REGION (SEQ ID NO:36)
a a g g c c a g c t g c c a c c a t c c c t a t a c c c a c a c c c c t c a c t c t a c t c c t c c c a c c c c c a a c a g
    G    T    F    S    L    R    K    L    W    A    F    T    G    P    G    F    L    M    S    I    A
G G C A C C T T C A G C C T G C G G A A G C T A T G G G C C T T C A C G G G G C C T G G C T T C C T C A T G A G C A T T G C
    F    L    D    P    G    N    I    E    S    D    L    Q    L    G    P    V    A    G    F    K
T T T C C T G G A C C C A G G A A A C A T C G A G T C A G A T C T T C A G C T N G G N C C N G T G G C G G G A T T C A A A g
t a a c t a a g t c g g g a c c t g a g t g g g a c a c t t

EXON 4 AMPLIFIED REGION (SEQ ID NO:37)
                                                            L    L    W    V    L    L    W    A
c c t c t c t g g c t g a a g g c c t c t c c c t g c c t c c t c a c a g C T T C T C T G G G T G C T G C T C T G G G C C A
T    V    L    G    L    L    C    Q    R    L    A    A    R    L    G    V    V    T    G    K    D
C C G T G T T G G G C T T G C T C T G C C A G C G A C T G G C T G C A C G T C T G G G C G T G G T G A C A G G C A A G G A C
    L    G    E    V    C    H    L    Y    Y    P    K
T T G G G C G A G G T C T G C C A T C T C T A C T A C C C T A A Gg t g a g c t t g g g g g g c c t g g a c a g g g a g a a
c c a c t g g c c c c a a a c c c c a a a c a g c c a t t t t c a g c t t c c a c g a

EXON 5 AMPLIFIED REGION (SEQ ID NO:38)
                                                                         V    P    R    T
a c a g g c a a a t a a c c g c c c a c c c t t a a t g a a g g a t c a t c t c c t c c c c a t c a g GT G C C C C G C A C
    V    L    W    L    T    I    E    L    A    I    V    G    S    D    M    Q    E    V    I    G
C G T C C T C T G G C T G A C C A T C G A G C T A G C C A T T G T G G G C T C C G A C A T G C A G G A A G T C A T C G G C A
T    A    I    A    F    N    L    L    S    A    G    R
C G G C C A T T G C A T T C A A T C T G C T C T C A G C T G G A C Gg t a c c a c c c c a g t g t c c c c a a c t c t t c a
g g c a g g c a g a g a a c a g c t g c t g c t a c t t c c c c c c c t a a c c a g t c c c t c c c a g a g t c t a t t t t
a t c c t g c t g t c c c c t c t g a a g c a g c t g c t g c c c t g t t t t c c a g a a a t g t a a a g t g a c t t g t c
t a a a g t c a c a c a g a t g t g a g t c a t g c a g g a c c c c g g g a c t g c a g

EXON 6 + 7 AMPLIFIED REGION (SEQ ID NO:S 39 and 40)
                                                                                    I    P    L    W    G
a g a c c c c t g g t c c t g g c t g g g c t g a c c c g g g c c a c t c t g g t t t c a g AA T C C C A C T C T G G G G T
    G    V    L    I    T    I    V    D    T    F    F    L    F    L    D    N    Y
G G C G T C C T C A T C A C C A T C G T G G A C A C C T T C T T C T T C C T C T T C C T C G A T A A C T A C g t g g g t g
c a c a c c c c a c c t c a t a g g g g a g t g g t g g t g g t g a g g g t g c t g t a c t n g g g a g a a g g g c t c t g
a c a t c g a a c a g c c t g g g a g c g c a c c t g a g c t c c c t c a c t c t c c c t g g g t g c c t c t a g c g a g
t t a c t t g g a c g g c t c t c t t c a c c t g t a c a t g g g a a a t a a t a g c a c a g a c t t c a g a g g g t - - -
- - - - - - - - - - - - - - - - - - - - - 3 2    b p - - - - - - - - - - - - - - - - - - - - - - - - - - - - - - - - -
a t a g c c a t a c g a t g t g a t g t c a c a g a t t t t t t c g t g g n t t g g t t t a g g t t t g g t t t g g t t c t
                    G    L    R    K    L    E    A    F    F    G    L    L    I    T    I    M    A    L
g c t a g t a g G G C T G C G G A A G C T G G A A G C T T T T T T T G G A C T C C T T A T A A C C A T T A T G G C C T T G A
T    F    G    Y    E
C C T T T G G C T A T G A Gg t a g g a a g c c a g t g c t g c a a c c EXON 8 (SEQ ID NO:41)
g g a a g c c a g t g c t g c a a c c c c a c t g t g g a c c t c c c a a g a t c a t t c c t c t c c c t t c c c t c c t c
t g g c c g c g g g n n n g g g g g g g g g c t g g g g t g g g a t g g a g g c t g a g a a a t g g t g a c c g c g g c g
                                                                                                               Y    V    V    A    R
t g g t t g c g n g g g g c g g g g c t t g t c c t g a c c a g g c t c c t c c c t g c a g T A T G T G G T C G C C G T T C TABLE 6-continued OVERLINED SEQUENCES REPRESENT REGIONS SELECTED FOR PRIMERS TO
AMPLIFY INDIVIDUAL EXONS.

```
       P   E   Q   G   A   L   L   R   G   L   F   L   P   S   C   P   G   C   H   P
       CTGAGCAGGGAGCGCTTCTTCGGGGCCTGTTCCTGCCCTCGTGCCCGGGCTGCGGCCACCCC
         E   L   L   Q   A   V   G   I   V   G   A   I   I   M   P   H   N   I   Y   L   H
       GAGCTGCTGCAGGCGGTGGGACTTGTTGGCGCCATCATCATGCCCCACAACATCTACCTGCA
           S   A   L   V   K
       CTCGGCCTGGTCAAGgtgagcagaggggaggggaaagagacccctcactcagtcggagcc
       atgctggctccgcctccaannttggagccct
```

EXON 9 (SEQ ID NO:42)
ctgcagtgagccatgcattgcaccacggcactccagtctgggtgacagaacaaaacctgtct ctaaaaataaaataagtaagctggacacgtctgaggatggaacaaggtgagtgaaggagcg tgtcaggacctgaggtagccagggacctcaaaggccagccttgcttcacccacacagtgctt acagtggtaaggcctctgtggcaagaacagagatgtagaaaccatcggctgacctgaacctg cccagactgccacgcagggcacttaagaaggtactgggctttggggagaacatagaagtgtg aagggtggggacactgtggtggctctgagggactttggcacttccctctc S   R   E   I   D   R   A   R   R   V   D   I   R   E   A
ccttttgatcttcgtagTCTCGAGAGATAGACCGGGCCCGCCGAGTCGACATCAGAGAAGCCA
N   M   Y   F   L   I   E   A   T   I   A   L   S   V   S   F   I   N   L   F
ACATGTACTTCCTGATTGAGGCCACCATCGCCCTGTCCGTCTCCTTTATCATCAACCTCTTT
  V   M   A   A   F   G   Q   A   F   Y   Q   K   T   K   Q   A   A
GTCATGGCTGCATTTGGGCAGGCCTTCTACCAGAAAACCAAGCAGGCTGCGgtgagacacac tttcccccgcacctgaggccacacacgtactcatgtcctgtaagccttgccgaggacctag gcaatgcagctgagcccttctgagtctctgccctgatgatcttccctgttggcagatatcat tcattcagcaaataatcattgagcatttgttatataccaagcacatcctagaccctggggat acagcagtcaatgctacaaagacccagctctctgcag EXON 10 (SEQ ID NO:43)
      tttggaaccctggtcagtgctaggcagtccagtttcccaaggctgaggntgctcctcac F   N   I   C   A   N   S   S   L
tcacatcttccttctactgccctggtacccacagTTCAACATCTGTGCCAACAGCAGCCTCC
H   D   Y   A   K   I   F   P   M   N   N   A   T   V   A   V   D   I   Y   Q   G
ACGACTACGCTAAGATCTTCCCCATGAACAACGCCACCGTGGCCGTGGACATTTACCAGGGG
gtgagngngggtgggtggggagggcgtgacccagagaggcgcctcgggcagggccaccggtg gtaccacactcgtccctgcag EXON 11 (SEQ ID NO:44)
ccgtggcactttaccgggggggtgagcgcgggtgggtggggagggcgtgacccagagaggctc G   V   I   L   G
cccgcctcgggcagggccaccggtcctaccacactcgtccctgcagGGCGTGATCCTGGGCT
C   L   F   G   P   A   A   L   Y   I   W   A   I   G   L   L   A   A   G   Q   S
GCCTGTTCGGCCCCGCGGCCCTCTACATCTGGGCCATAGGTCTCCTGGCGGCTGGGCAGAGC
  S   T   M   T   G   T   Y   A   G   Q   F   V   M   E
TCCACCATGACGGGCACCTACGCGGGACAGTTCGTGATGGAGgtagggcaggggcgggcca
ggag EXON 12 (SEQ ID NO:45)
aaatgtttagtcttcagnaaccagctatgggatgggagttccccatttctccccacccatcc cctcttgccacctagggacagagctgtcccagttcaacagtggaaaaacagagcatgccccc agggataaatcggttgagggacatcagaggatctctcctctggaatcccagtcctgtctac G   F   L   R   L   R   W   S   S   F   A
tcctcaccaaggagctcaccccccaccccagGGCTTCCTGAGGCTGCGGTGGTCAAGCTTCGC
    R   V   L   L   T   R   S   C   A   I   L   P   T   V   L   V   A   V   F   R
CCGTGTCCTCCTCACCCGCTCCTGCGCCATCCTGCCCACCGTGCTCGTGGCTGTCTTCCGGG
D   L   R   D   L   S   G   L   N   D   L   L   N   V   L   Q   S   L   L
ACCTGAGGGACTTGTCGGGCCTCAATGATCTGCTCAACGTGCTGCAGAGCCTGCTGgtga EXON 13 (SEQ ID NO:46)
          L   P   V   A   V   L   P   I   L   T   F   T   S   M   P   T   L   M   Q
ccagCTCCCGGTTGCCGTGCTGCCCATCCTCACGTTCACCAGCATGCCCACCCTCATGCAGG
E   F   A   N   G   L
AGTTTGCCAATGGCCTgtgagtaccccctttcccaagtgctggattgcatc

TABLE 6-continued

OVERLINED SEQUENCES REPRESENT REGIONS SELECTED FOR PRIMERS TO
AMPLIFY INDIVIDUAL EXONS.

EXON 14 AMPLIFIED REGION (SEQ ID NO:47)
```
                                                         L   N   K   V   V   T   S
c a g c a a c c a g c c a g t c c t g a g c c t c t c t c g t g t c c c c c a g GCT GAA CAA GGT CGT CAC CTC T
  S   I   M   V   L   V   C   T   I   N   L   Y   F   V   V   S   Y   L   P   S   L
T CCA TCA TGG TGC TAG TCT GCA CCA TCA ACC TCT ACT TCG TGG TCA GCT ATC TGC CCA GCC T
  P   H   P   A   Y   F   G   L   A   A   L   L   A   A   A   Y   L   G   L   S
G CCC CAC CCT GCC TAC TTC GGC CTT GCA GCC TTG CTG GCC GCA GCC TAC CTG GGC CTC AGC A
  T   Y   L
C CTA CCT Ggt a c a g t a g g g c c a g g g g a t g c c t t g g g a a t g g a t g a
```

EXON 15 AMPLIFIED REGION (SEQ ID NO:48)
```
t g c c t t g g g a a t g g a t g a t t c c c c a g a g g t c t t g g c a t c t c c c c a a t t c a t g g t t g c c c t c
                V   W   T   C   C   L   A   H   G   A   T   F   L   A   H   S   S   H   H
c c c c a g GTC TGG ACC TGT TGC CTT GCC CAC GGA GCC ACC TTT CTG GCC CAC AGC TCC CAC CA
  H   F   L   Y   G   L   L   E   E   D   H   K   G   E   T   S   G   *
C CAC TTC CTG TAT GGG CCT CCT TGA AGA GGA CCA CAA AGG GGA GAC CTC TGG CTA GGC CCA C
A CCA GGG CTG GCT GGG GAG TGG CAT GTA TGA CGT
```

TABLE 7

Peak LOD scores for pairwise linkage analysis between NRAMP and previously mapped (Ref 37) 2q34 (TNP1) and 2q35 (IL8RB, VIL1, DES) markers calculated for 36 Brazilian families. RF = recombination fraction (M = F) at which the peak LOD score was obtained. N = number of families contributing to the analysis.

| Marker intervals | N  | Peak LOD Score | RF    |
|------------------|----|----------------|-------|
| TNP1-NRAMP       | 14 | 10.49          | 0.026 |
| TNP1-IL8RB       | 9  | 6.02           | 0.032 |
| TNP1-VIL1        | 15 | 9.84           | 0.001 |
| TNP1-DES         | 19 | 11.45          | 0.046 |
| NRAMP-IL8RB      | 11 | 3.56           | 0.072 |
| NRAMP-VIL1       | 15 | 10.94          | 0.001 |
| NRAMP-DES        | 20 | 8.94           | 0.051 |
| IL8RB-VIL1       | 10 | 5.80           | 0.065 |
| IL8RB-DES        | 12 | 10.03          | 0.035 |
| VIL1-DES         | 14 | 9.47           | 0.059 |

REFERENCES

1. Blackwell, J. M. 1989. The macrophage resistance gene Lsh/Ity/Bcg. Res. Immunol. 140:767.
2. Vidal, S. M., D. Malo, K. Vogan, E. Skamene, and P. Gros. 1993. Natural resistance to infection with intracellular parasites: isolation of a candidate for Bcg. Cell 73:469.
3. Booker, G. W., I. Gout, A. K. Downing, P. C. Driscoll, J. Boyd, M. D. Waterfield, and I. D. Campbell. 1993. Solution structure and ligand-binding site of the SH3 domain of the p85α subunit of phosphatidylinositol 3-kinase. Cell 73:813.
4. Mayer, B. J. and D. Baltimore. 1993. Signalling through SH2 and SH3 domains. Trends Cell Biol. 3:8.
5. Gout, I., R. Dhand, I. D. Hiles, M. J. Fry, G. Panayotou, P. Das, O. Truong, N. F. Totty, J. Hsuan, G. W. Booker, I. D. Campbell and M. D. Waterfield (1993). The GTPase Dynamin Binds to and is Activated by a Subset of SH3 Domains. Cell. 75:25.
6. Morgenstern, J. P. and H. Land (1990) Advanced mammalian gene transfer: high titre retroviral vectors with multiple drug selection markers and a complementary helper-free packaging cell line. Nucleic Acids Res. 18:3587.
7. Markowitz, D., S. Goft and A. Bank (1988) A safe packaging line for gene transfer: separating virol genes on two different plasmids. J. Virol. 62:1120.
8. Smith, D. B. and K. S. Johnson (1988) Single-step purification of polypeptides expressed in Escherichia coli as fusions with glutathione S-transferase. Gene 67:31.
9. Formica, S., T. I. A. Roach and J. M. Blackwell (1994) Interaction with extracellular matrix proteins influences Lsh/Ity/Bcg (candidate Nramp) gene regulation of macrophage priming/activation for TNF-α and nitrite release. Immunology 82:42–50.
10. Otsu, M., I. D. Hiles, I. Goot, M. J. Fry, F. Ruiz-Larrea, G. Panayotou, A. Thompson, R. Dhand, J. Hsuan, N. Totty, A. D. Smith, S. J. Morgan, S. A. Courtneidge, P. J. Parker and M. D. Waterfield (1991). Characterization of two 85 kd proteins that associate with receptor tyrosine kinsases, middle-T/pp60 (c-src) complexes, and PI3-kinase. Cell 65: 91.
11. Roach, T. I., A. F. Kiderlen, and J. M. Blackwell. 1991. Role of inorganic nitrogen oxides and tumor necrosis factor alpha in killing Leishmania donovani amastigotes in gamma interferon-lipopolysaccharide-activated macrophages from $Lsh^s$ and $Lsh^r$ congenic mouse strains. Infect. Immun. 59:3935.
12. Booker, G. W., A. I. Breeze, A. K. Downing, G. Panayotou, I. Gout, M. D. Waterfield and I. D. Campbell (1992) Structure of an SH2 domain of the p85 alpha subunit of phosphatidylinositol-3-OH kinase. Nature 358: 684.
13. Otto, E., M. Kunimoto, T. McLaughlin and V. Bennett. (1991) Isolation and characterization of cDNAs encoding human brain ankyrins reveal a family of alternatively spliced genes. J. Cell Biol. 114: 241.
14. Kyte, J. and R. F. Doolitle. 1982. A simple method for displaying the hydropathic character of a protein. J. Mol. Biol. 157:105.
15. Kozak, M. 1984. Point mutations close to the AUG initiator codon affect the efficiency of translation of rat pre-proinsulin in vivo. Nature 308:241.
16. Kozak, M. 1986. Point mutations define a sequence flanking the AUG initiator codon that modulates translation by eukaryotic ribosomes. Cell 44:283.
17. Chen, M. S., R. A. Obar, C. C. Schroeder, T. W. Austin, C. A. Poodry, S. C. Wadsmworth and R. B. Vallee. 1991. Multiple forms of dynamin are encoded by shibire, a Drosophila gene involved in endocytosis. Nature 351:583.

18. Robinson, P. J., J.-M. Sontag, J.-P. Liu, E. M. Fykse, C. Slaughter, H. McMahon, and T. C. Südhof. 1993. Dynamin GTPase regulated by protein kinase C phosphorylation in nerve terminals. Nature 365:163.
19. Frielle, T., S. Collins, K. W. Daniel, M. G. Caron, R. J. Lefkowitz and B. K. Kobilka. 1987. Cloning of the cDNA for the human beta 1-adrenergic receptor. Proc. Natl. Acad. Sci. U.S.A. 84:7920.
20. Schaller, M. D., C. A. Borgman, B. S. Cobb, R. R. Vines, A. B. Reynolds and J. T. Parsons. 1992. pp125$^{FAK}$, a structurally distinctive protein-tyrosine kinase associated with focal adhesions. Proc. Natl. Acad. Sci. U.S.A. 89:5192.
21. Lipfert, L., B. Haimovich, M. D. Schaller, B. S. Cobb, J. T. Parsons and J. S. Brugge. 1992. Integrin-dependent phosphorylation and activation of the protein tyrosine kinase pp125$^{FAK}$. J. Cell Biol. 119:905.
22. Vallee, R. B. and H. S. Shpetner. 1993. Dynamin in synaptic dynamics. Nature 365:107.
23. Sadler, J., A. W. Crawford, J. W. Michelson and M. C. Beckerle. (1992) Zyxin and cCRP: Two interactive LIM domain proteins associated with the cytoskeleton. J. Cell Biol. 119: 1573–1588.
24. Roach, T. I. A., D. Chatterjee, and J. M. Blackwell. (1994) lipoarabinomannans; regulation of KC expression in murine macrophages by Lsh/Ity/Bcg (candidate Nramp). Infect. Immun. 62: 1176–1184
25. Benit, L., M. Charon, L. Cocault, F. Wending and S. Gisselbrecht. 1993. The 'WS motif' common to v-mpl and members of the cytokine receptor superfamily is dispensable for myeloproliferative leukemia virus pathogenicity. Oncogene 8:787.
26. Kuramochi, S., T. Chiba, H. Amanuma, A. Tojo and K. Todokoro. 1991. Growth signal erythropoietin activates the same tyrosine kinases as interleukin 3, but activates only one tyrosine kinase as differentiation signal. Biochem. Biophysic. Res. Commun. 181:1103.
27. Ziegler, S. F., C. B. Wilson and R. M. Perlmutter. 1988. Augmented expression of a myeloid-specific protein tyrosine kinase gene (hck) after macrophage activation. J. Exp. Med. 168:1801.
28. English, B. K., J. N. Ihle, A. Myracle and T. Yi. 1993. Hck tyrosine kinase activity modulates tumor necrosis factor production by murine macrophages. J. Exp. Med. 178:1017.
29. Devereaux, J., P. Haeberli and O. Smithies. 1984. A comprehensive set of sequence analysis programs for the VAX. Nuc. Acid Res. 12:387.
30. Larin Z., Monaco A. P., Lehrach H. (1991) Yeast artificial chromosome libraries containing large inserts from mouse and human DNA. Proc Natl Acad Sci U.S.A. 88: 4123–4127
31. Pringault E., Arpin M., Garcia A., Finidori J., Louvard D. (1986) A human villin cDNA clone to investigate the differentiation of intestinal and kidney cells in vivo and in culture. EMBO J 5: 3119–3124
32. White J. K., Shaw M.-A., Barton C. H., et al (1994) Genetic and physical mapping of 2q35 in the region of NRAMP and IL8R genes: Identification of a polymorphic repeat in exon 2 of NRAMP. Genomics 24:295–302
33. Tsuchiya S., Yamabe M., Yamaguchi Y., Kobayashi Y., Konno T., Tada K. (1980) Establishment and characterization of a human acute monocyte leukemia cell line (THP-1). Int J Cancer 26: 171–176
34. Edwards J. B. D. M., Delort J., Mallet J. (1991) Oligodeoxyribonucleotide ligation to single-stranded cDNAs: a new tool for cloning 5' ends of mRNAs and for constructing cDNA libraries by in vitro amplification. Nucleic Acids Res 19: 5227–5232
35. West A. H., Clark D. J., Martin J., Neupert W., Hartl F. U., Horwich A. L. (1992) Two related genes encoding extremely hydrophobic proteins suppress a lethal mutation in the yeast mitochondrial processing enhancing protein. J Biol Chem 267: 24625–24633
36. Higgins D. G., Sharpe P. M. (1988) CLUSTAL: a package for performing multiple sequence alignment on a microcomputer. Gene 73: 237–244
37. Shaw M.-A., Atkinson S., Dockrell H., et al (1993) An RFLP map for 2q33–q37 from multicase mycobacterial and leishmanial disease families: No evidence for an Lsh/Ity/Bcg gene homologue influencing susceptibility to leprosy. Ann Hum Genet 57: 251–271
38. Lathrop G. M., Lalouel J. M. (1984) Easy calculations of lod scores and genetic risks on small computers. Am J. Hum Genet 36: 460–465
39. Rich A., Nordheim A., Wang A. H.-J. (1984) The chemistry and biology of left-handed Z-DNA. Ann Rev Biochem 53: 791–846
40. Hamada H., Kakunaga T. (1982) Potential Z-DNA forming sequences are highly dispersed in the human genome. Nature 298: 396–398
41. Yang Z., Sugawara M., Ponath P. D., et al (1990) Interferon gamma response region in the promoter of the human DPA gene. Proc Natl Acad Sci U.S.A. 87: 9226–9230
42. Pearse R. N., Feinman R., Ravetch J. V. (1991) Characterization of the promoter of the human gene encoding the high-affinity IgG receptor: Transcriptional induction by gamma-interferon is mediated through common DNA response elements. Proc Natl Acad Sci U.S.A. 88: 11305–11309
43. Mackman N., Brand K., Edgington T. S. (1991) Lipopolysaccharide-mediated transcriptional activation of the human tissue factor gene in THP-1 monocytic cells requires both activator protein 1 and nuclear factor kB binding sites. J Exp Med 174: 1517–1526
44. Lenardo M. J., Baltimore D. (1989) NF-kB: A pleiotropic mediator of inducible and tissue-specific gene control. Cell 58: 227–229
45. Klemsz M. J., McKercher S. R., Celada A., Van Beveren C., Maki R. A. (1990) The macrophage and B cell-specific transcription factor PU.1 is related to the ets oncogene. Cell 61: 113–124
46. Karim F. D., Urness L. D., Thummel C. S., et al (1990) The ETS-domain: a new DNA-binding motif that recognizes a purine-rich core DNA sequence. Genes and Development 4: 1451–1453
47. Cassady A. I., Stacey K. J., Nimmo K. A., et al (1991) Constitutive expression of the urokinase plasminogen activator gene in murine RAW264 macrophages involves distal and 5' non-coding sequences that are conserved between mouse and pig. Nucleic Acids Res 19: 6839–6847
48. Lis J., Wu C. (1992) Heat shock factor. In: McKnight S. L., Yamamoto K. R. (eds) Transcriptional Regulation. Cold Spring Harbor Laboratory Press, pp 907–930
49. Dosik J. K., Barton C. H., Holiday D. L., Krall M. M., Blackwell J. M., Mock B. A. (1994) An Nramp-related sequence maps to mouse chromosome 17. Mammalian Genome 5: 458–460
50. Feinman R., Qiu W. Q., Pearse R. N., et al (1994) PU.1 and an HLH family member contribute to the myeloid-specific transcription of the Fc-gamma-RIIIA promoter. EMBO J 13: 3852–3860
51. Zhang D.-E., Hetherington C. J., Chen H.-M., Tenen D. G. (1994) The macrophage transcription factor PU.1 directs tissue-specific expression of the macrophage colony-stimulating factor receptor. Mol Cell Biol 14: 373–381

52. Xie Q.-w., Whisnant R., Nathan C. (1993) Promoter of the mouse gene encoding calcium-independent nitric oxide synthase confers inducibility by interferon gamma and bacterial lipopolysaccaride. J Exp Med 177: 1779–1784

53. Crocker P. R., Davies E. V., Blackwell J. M. (1987) Variable expression of the murine natural resistance gene Lsh in different macrophage populations infected in vitro with *Leishmania donovani*. Parasite Immunol 9: 705–719

54. Davies E. V., Singleton A. M., Blackwell J. M. (1988) Differences in Lsh gene control over systemic Leishmania major and Leishmania donovani or Leishmania mexicana mexicana infections are caused by differential targeting to infiltrating and resident liver macrophage populations. Infect Immun 56: 1128–1134

55. Barton C. H., White J. K., Roach T. I. A., Blackwell J. M. (1994) NH$_2$-terminal sequence of macrophage-expressed natural resistance-associated macrophage protein (Nramp) encodes a proline/serine-rich putative Src homology 3-binding domain. J Exp Med 179: 1683–1687

56. Malo D., Vogan K., Vidal S., et al (1994) Haplotype mapping and sequence analysis of the mouse Nramp gene predict susceptibility to infection with intracellular parasites. Genomics 23: 51–61

57. Blackwell J. M., Barton C. H., White J. K., et al (1994) Genetic regulation of leishmanial and mycobacterial infections: The Lsh/Ity/Bcg gene story continues. Immunol Lett 43: 99–107

58. Schurr E., Radzioch D., Malo D., Gros P., Skamene E. (1991) Molecular genetics of inherited susceptibility to intracellular parasites. Behring Inst Mitt 88: 1–12

59. Schurr E., Malo D., Radzioch D., et al (1991) Genetic control of innate resistance to mycobacterial infections. Immunology Today 12: A42–A45

60. Boguski M. S., Lowe T. M. J., Tolstoshev C. M. (1993) dbEST-database for "expressed sequence tags". Nature Genet 4: 332–333

61. Schulze-Osthoff K. Beyaert R., Vandevoorde V., Haegeman G., Fiers W. (1993) Depletion of the mitochondrial electron transport abrogates the cytotoxic and gene-inductive effects of TNF. EMBO J. 12: 3095–3104.

62. Blackwell J. M., Barton C. H., White J. K., Searle S., Baker A.-M., Williams H., Shaw M.-A. (1994) Genomic Organisation and sequence of the human NRAMP gene: identification and mapping of a promoter region polymorphism. Mol. Med. (in press)

SEQUENCE LISTING ( 1 ) GENERAL INFORMATION:

( i i i ) NUMBER OF SEQUENCES: 63

( 2 ) INFORMATION FOR SEQ ID NO: 1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO: 1:

```
Pro Gly Pro Ala Pro Gln Pro Xaa Pro Xaa Arg
1               5                   10
```

( 2 ) INFORMATION FOR SEQ ID NO: 2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO: 2:

```
Pro Gly Pro Ala Pro Gln Pro Ala Pro Cys Arg
1               5                   10
```

( 2 ) INFORMATION FOR SEQ ID NO: 3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO: 3:

```
Pro Xaa Ser Pro Thr Ser Pro Xaa Pro Xaa Xaa Ala Pro Pro Arg Xaa
1               5               10                  15
```

Thr (2) INFORMATION FOR SEQ ID NO: 4:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 4:

```
Pro Thr Ser Pro Thr Ser Pro Gly Pro Gln Gln Ala Pro Pro Arg Glu
1               5                   10                  15
Thr
```

(2) INFORMATION FOR SEQ ID NO: 5:

(i) SEQUENCE CHARACTERISTICS:
        (A) LENGTH: 16 amino acids
        (B) TYPE: amino acid
        (C) STRANDEDNESS: single
        (D) TOPOLOGY: linear (ix) FEATURE:
        (A) NAME/KEY: Region
        (B) LOCATION:1
        (D) OTHER INFORMATION:/note= "XAA REPRESENTS SER OR ALA"

(ix) FEATURE:
        (A) NAME/KEY: Region
        (B) LOCATION:4
        (D) OTHER INFORMATION:/note= "XAA REPRESENTS ARG OR LYS"

(ix) FEATURE:
        (A) NAME/KEY: Region
        (B) LOCATION:13
        (D) OTHER INFORMATION:/note= "XAA REPRESENTS ILE OR VAL"

(xi) SEQUENCE DESCRIPTION: SEQ ID NO: 5:

```
Xaa Pro Pro Xaa Xaa Ser Arg Pro Xaa Xaa Xaa Ser Xaa Xaa Ser Xaa
1               5                   10                  15
```

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO: 6:

```
Ser Pro Pro Arg Leu Ser Arg Pro Ser Tyr Gly Ser Ile Ser Ser Leu
1               5                   10                  15
```

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 7:

```
Gly Pro Gln Arg Leu Ser Gly Ser Ser Tyr Gly Ser Ile Ser Ser
1               5                   10                  15
```

(2) INFORMATION FOR SEQ ID NO: 8:

(i) SEQUENCE CHARACTERISTICS:

( A ) LENGTH: 33 base pairs
( B ) TYPE: nucleic acid
( C ) STRANDEDNESS: double
( D ) TOPOLOGY: linear ( x i ) SEQUENCE DESCRIPTION: SEQ ID NO: 8:

CCTGGCCCAG CACCTCAGCC AGCGCCTTGC CGG  33

( 2 ) INFORMATION FOR SEQ ID NO: 9:

( i ) SEQUENCE CHARACTERISTICS:
( A ) LENGTH: 48 base pairs
( B ) TYPE: nucleic acid
( C ) STRANDEDNESS: double
( D ) TOPOLOGY: linear ( x i ) SEQUENCE DESCRIPTION: SEQ ID NO: 9:

AGCCCCCGA GGCTGAGCAG GCCCAGTTAT GGCTCCATTT CCAGCCTG  48

( 2 ) INFORMATION FOR SEQ ID NO: 10:

( i ) SEQUENCE CHARACTERISTICS:
( A ) LENGTH: 51 base pairs
( B ) TYPE: nucleic acid
( C ) STRANDEDNESS: double
( D ) TOPOLOGY: linear ( x i ) SEQUENCE DESCRIPTION: SEQ ID NO: 10:

CCGACCAGCC CGACCAGCCC AGGGCCACAG CAAGCACCTC CCAGAGAGAC C  51

( 2 ) INFORMATION FOR SEQ ID NO: 11:

( i ) SEQUENCE CHARACTERISTICS:
( A ) LENGTH: 45 base pairs
( B ) TYPE: nucleic acid
( C ) STRANDEDNESS: double
( D ) TOPOLOGY: linear ( x i ) SEQUENCE DESCRIPTION: SEQ ID NO: 11:

GGTCCCCAAA GGCTAAGCGG GTCCAGCTAT GGTTCCATCT CCAGC  45

( 2 ) INFORMATION FOR SEQ ID NO: 12:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( x i ) SEQUENCE DESCRIPTION: SEQ ID NO: 12:

Asp Lys Ser Pro Pro Arg Leu Ser Arg Pro Ser Tyr Gly Ser Ile Ser
1               5                   10                  15

Ser ( 2 ) INFORMATION FOR SEQ ID NO: 13:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( x i ) SEQUENCE DESCRIPTION: SEQ ID NO: 13:

Pro Gln Pro Ala Pro Cys Arg Glu Thr Tyr Leu Ser Glu Lys Ile Pro
1               5                   10                  15

Ile Pro ( 2 ) INFORMATION FOR SEQ ID NO: 14:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( x i ) SEQUENCE DESCRIPTION: SEQ ID NO: 14:

Gly Thr Phe Ser Leu Arg Lys Leu Trp Ala Phe Thr Gly Pro Gly Phe
1               5                   10                  15

Leu Met Ser Ile Ala Phe Leu Asp Pro Gly Asn Ile Glu Ser Asp Leu
            20              25                  30

Gln ( 2 ) INFORMATION FOR SEQ ID NO: 15:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( x i ) SEQUENCE DESCRIPTION: SEQ ID NO: 15:

Trp Thr Cys Cys Ile Ala His Gly Ala Thr Phe Leu Thr His Ser Ser
1               5                   10                  15

His Lys His Phe Leu Tyr Gly Leu
            20

( 2 ) INFORMATION FOR SEQ ID NO: 16:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 16:

TCTGCGCTGG GAATGGGG                                                                18

( 2 ) INFORMATION FOR SEQ ID NO: 17:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 17:

TGCAAGCAGA TCGGGTCA                                                                18

( 2 ) INFORMATION FOR SEQ ID NO: 18:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 18:

GTGCTGCCCA TCCTCACG                                                                18

( 2 ) INFORMATION FOR SEQ ID NO: 19:

( i ) SEQUENCE CHARACTERISTICS:
( A ) LENGTH: 18 base pairs (B) TYPE: nucleic acid
(C) STRANDEDNESS: single
(D) TOPOLOGY: linear (xi) SEQUENCE DESCRIPTION: SEQ ID NO: 19:

GAGTTTGCCA ATGGCCTG                                                                                              18

(2) INFORMATION FOR SEQ ID NO: 20:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 20:

GGACGAGAAG GGAACTAG                                                                                              18

(2) INFORMATION FOR SEQ ID NO: 21:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 21:

AAGAAGGTGT CCACAATGGT G                                                                                          21

(2) INFORMATION FOR SEQ ID NO: 22:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 22:

CGGTTTTGTG TCTGGGAT                                                                                              18

(2) INFORMATION FOR SEQ ID NO: 23:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO: 23:

GACAGGCAAG GACTTGGGT                                                                                             19

(2) INFORMATION FOR SEQ ID NO: 24:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 24:

AAGAAGGTGT CCACAATGGT G                                                                                          21

(2) INFORMATION FOR SEQ ID NO: 25:

(i) SEQUENCE CHARACTERISTICS:
(A) LENGTH: 22 base pairs
(B) TYPE: nucleic acid
(C) STRANDEDNESS: single (D) TOPOLOGY: linear (xi) SEQUENCE DESCRIPTION: SEQ ID NO: 25:

CATCTCTACT ACCCCAAGGT GC                                          22

(2) INFORMATION FOR SEQ ID NO: 26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 26:

GAGGGGTCTT GGAACTCCA                                              19

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 27:

CACCTTCTCC GGCAGCCC                                               18

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 28:

TACCCCATGA CCACACCC                                               18

(2) INFORMATION FOR SEQ ID NO: 29:

(i) SEQUENCE CHARACTERISTICS:
        (A) LENGTH: 44 base pairs
        (B) TYPE: nucleic acid
        (C) STRANDEDNESS: double
        (D) TOPOLOGY: linear (xi) SEQUENCE DESCRIPTION: SEQ ID NO: 29:

TGTGTGTGTG TACGTGTGTG TGTACGTGTG TGTGTGTGTG TGTG                  44

(2) INFORMATION FOR SEQ ID NO: 30:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 30:

GGGRHTYYCC                                                        10

(2) INFORMATION FOR SEQ ID NO: 31:

(i) SEQUENCE CHARACTERISTICS:
        (A) LENGTH: 48 base pairs
        (B) TYPE: nucleic acid
        (C) STRANDEDNESS: double
        (D) TOPOLOGY: linear ( x i ) SEQUENCE DESCRIPTION: SEQ ID NO: 31:

TGTGTGTGTG TACGTGTGTG TGTACGTGTG TGTGTGTGTG TGTGTGTG                        48

( 2 ) INFORMATION FOR SEQ ID NO: 32:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 32:

TGTGTGTGTG TACGTGTGTG TGTACGTGTG TGTGTGTGTG TG                              42

( 2 ) INFORMATION FOR SEQ ID NO: 33:

( i ) SEQUENCE CHARACTERISTICS:
        ( A ) LENGTH: 34 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 33:

TGTGTGTGTG TACGTGTGTG TGTACGTGTG TGTG                                      34

( 2 ) INFORMATION FOR SEQ ID NO: 34:

( i ) SEQUENCE CHARACTERISTICS:
        ( A ) LENGTH: 260 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 34:

ATGTAAGAGG CAGGGCACTC GGCTGCGGAT GGGTAACAGG GCGTGGGCTG GCACACTTAC           60

TTGCACCAGT GCCCAGAGAG GGGGTGCAGG CTGAGGAGCT GCCCAGAGCA CCGCTCACAC           120

TCCCAGAGTA CCTGAAGTCG GCATTTCAAT GACAGGTGAG TAGTGGCCCC TAGGGACAGA           180

GCCTGATTGG GGGGTGGAGT GGAGGAGATC ACTAGGCTGG TGGAGACTTG AGGAAGCAAG           240

AAAGCCCTTG GTCCCCTGTG                                                      260

( 2 ) INFORMATION FOR SEQ ID NO: 35:

( i ) SEQUENCE CHARACTERISTICS:
        ( A ) LENGTH: 196 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 35:

TCACCATGCT TCATGGGCCC CCACAGGTGA CAAGGGTCCC CAAAGGCTAA GCGGGTCCAG           60

CTATGGTTCC ATCTCCAGCC CGACCAGCCC GACCAGCCCA GGGCCACAGC AAGCACCTCC           120

CAGAGAGACC TACCTGAGTG AGAAGATCCC CATCCCAGAC ACAAAACCGG TGGGACCTGG           180

AAACTTTCTG GGGGCT                                                          196

( 2 ) INFORMATION FOR SEQ ID NO: 36:

( i ) SEQUENCE CHARACTERISTICS:
        ( A ) LENGTH: 213 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 36:

```
AAGGCCAGCT  GCCACCATCC  CTATACCCAC  ACCCCTCACT  CTACTCCTCC  CACCCCCAAC       60

AGGGCACCTT  CAGCCTGCGG  AAGCTATGGG  CCTTCACGGG  GCCTGGCTTC  CTCATGAGCA      120

TTGCTTTCCT  GGACCCAGGA  AACATCGAGT  CAGATCTTCA  GCTGGCCGTG  GCGGGATTCA      180

AAGTAACTAA  GTCGGGACCT  GAGTGGGACA  CTT                                    213
```

( 2 ) INFORMATION FOR SEQ ID NO: 37:

( i ) SEQUENCE CHARACTERISTICS:
        ( A ) LENGTH: 229 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 37:

```
CCTCTCTGGC  TGAAGGCCTC  TCCCTGCCTC  CTCACAGCTT  CTCTGGGTGC  TGCTCTGGGC       60

CACCGTGTTG  GGCTTGCTCT  GCCAGCGACT  GGCTGCACGT  CTGGGCGTGG  TGACAGGCAA      120

GGACTTGGGC  GAGGTCTGCC  ATCTCTACTA  CCCTAAGGTG  AGCTTGGGGG  GCCTGGACAG      180

GGAGAACCAC  TGGCCCCAAA  CCCCAAACAG  CCATTTTCAG  CTTCCACGA                   229
```

( 2 ) INFORMATION FOR SEQ ID NO: 38:

( i ) SEQUENCE CHARACTERISTICS:
        ( A ) LENGTH: 354 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 38:

```
ACAGGCAAAT  AACCGCCCAC  CCTTAATGAA  GGATCATCTC  CTCCCCATCA  GGTGCCCCGC       60

ACCGTCCTCT  GGCTGACCAT  CGAGCTAGCC  ATTGTGGGCT  CCGACATGCA  GGAAGTCATC     120

GGCACGGCCA  TTGCATTCAA  TCTGCTCTCA  GCTGGACGGT  ACCACCCAG   TGTCCCCAAC     180

TCTTCAGGCA  GGCAGAGAAC  AGCTGCTGCT  ACTTCCCCCC  CTAACCAGTC  CCTCCCAGAG     240

TCTATTTTAT  CCTGCTGTCC  CCTCTGAAGC  AGCTGCTGCC  CTGTTTTCCA  GAAATGTAAA     300

GTGACTTGTC  TAAAGTCACA  CAGATGTGAG  TCATGCAGGA  CCCCGGGACT  GCAG           354
```

( 2 ) INFORMATION FOR SEQ ID NO: 39:

( i ) SEQUENCE CHARACTERISTICS:
        ( A ) LENGTH: 306 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 39:

```
AGACCCCTGG  TCCTGGCTGG  GCTGACCCGG  GCCACTCTGG  TTTCAGAATC  CCACTCTGGG       60

GTGGCGTCCT  CATCACCATC  GTGGACACCT  TCTTCTTCCT  CTTCCTCGAT  AACTACGGTG     120

GGTGCACACC  CCACCTCATA  GGGGAGTGGT  GGTGGTGAGG  GTGCTGTACT  GGGAGAAGGG     180

CTCTGACATC  GAACAGCCTG  GGAGCGCACC  TGAGCTCCCT  CACTCTCCCC  TGGGTGCCTC     240

TAGCGAGTTA  CTTGGACGGC  TCTCTTCACC  TGTACATGGG  AAATAATAGC  ACAGACTTCA     300

GAGGGT                                                                    306
```

( 2 ) INFORMATION FOR SEQ ID NO: 40:

( i ) SEQUENCE CHARACTERISTICS:
        ( A ) LENGTH: 159 base pairs
        ( B ) TYPE: nucleic acid ( C ) STRANDEDNESS: double
( D ) TOPOLOGY: linear ( x i ) SEQUENCE DESCRIPTION: SEQ ID NO: 40:

| | | | | | | |
|---|---|---|---|---|---|---|
| ATAGCCATAC | GATGTGATGT | CACAGATTTT | TTCGTGGTTG | GTTTAGGTTT | GGTTTGGTTC | 60 |
| TGCTAGTAGG | GCTGCGGAAG | CTGGAAGCTT | TTTTTGGACT | CCTTATAACC | ATTATGGCCT | 120 |
| TGACCTTTGG | CTATGAGGTA | GGAAGCCAGT | GCTGCAACC | | | 159 |

( 2 ) INFORMATION FOR SEQ ID NO: 41:

( i ) SEQUENCE CHARACTERISTICS:
( A ) LENGTH: 394 base pairs
( B ) TYPE: nucleic acid
( C ) STRANDEDNESS: double
( D ) TOPOLOGY: linear ( x i ) SEQUENCE DESCRIPTION: SEQ ID NO: 41:

| | | | | | | |
|---|---|---|---|---|---|---|
| GGAAGCCAGT | GCTGCAACCC | CACTGTGGAC | CTCCCAAGAT | CATTCCTCTC | CCTTCCCTCC | 60 |
| TCTGGCCGCG | GGGGGGGGGC | TGGGGTGGGA | TGGAGGCTGA | GAAATGGTGA | CCGCGGCGTG | 120 |
| GTTGCGGGGG | CGGGGCTTGT | CCTGACCAGG | CTCCTCCCTG | CAGTATGTGG | TCGCCGTTCC | 180 |
| TGAGCAGGGA | GCGCTTCTTC | GGGGCCTGTT | CCTGCCCTCG | TGCCCGGGCT | GCGGCCACCC | 240 |
| CGAGCTGCTG | CAGGCGGTGG | GACTTGTTGG | CGCCATCATC | ATGCCCACA | ACATCTACCT | 300 |
| GCACTCGGCC | CTGGTCAAGG | TGAGCAGAGG | GGAGGGAAA | GAGACCCCT | CACTCAGTCG | 360 |
| GAGCCATGCT | GGCTCCGCCT | CCAATGGAGC | CCCT | | | 394 |

( 2 ) INFORMATION FOR SEQ ID NO: 42:

( i ) SEQUENCE CHARACTERISTICS:
( A ) LENGTH: 769 base pairs
( B ) TYPE: nucleic acid
( C ) STRANDEDNESS: double
( D ) TOPOLOGY: linear ( x i ) SEQUENCE DESCRIPTION: SEQ ID NO: 42:

| | | | | | | |
|---|---|---|---|---|---|---|
| CTGCAGTGAG | CCATGCATTG | CACCACGGCA | CTCCAGTCTG | GGTGACAGAA | CAAAACCTGT | 60 |
| CTCTAAAAAA | TAAATAAGT | AAGCTGGACA | CGTCTGAGGA | TGGAACAAGG | TGAGTGAAGG | 120 |
| AGCGTGTCAG | GACCTGAGGT | AGCCAGGGAC | CTCAAAGGCC | AGCCTTGCTT | CACCCACACA | 180 |
| GTGCTTACAG | TGGTAAGGCC | TCTGTGGCAA | GAACAGAGAT | GTAGAAACCA | TCGGCTGACC | 240 |
| TGAACCTGCC | CAGACTGCCA | CGCAGGGCAC | TTAAGAAGGT | ACTGGGCTTT | GGGGAGAACA | 300 |
| TAGAAGTGTG | AGGGTGGGGG | ACACTGTGGT | GGCTCTGAGG | GACTTTGGCA | CTTCCCTCTC | 360 |
| CCTTTGATCT | TCGTAGTCTC | GAGAGATAGA | CCGGGCCCGC | CGAGTCGACA | TCAGAGAAGC | 420 |
| CAACATGTAC | TTCCTGATTG | AGGCCACCAT | CGCCCTGTCC | GTCTCCTTTA | TCATCAACCT | 480 |
| CTTTGTCATG | GCTGCATTTG | GGCAGGCCTT | CTACCAGAAA | ACCAAGCAGG | CTGCGGTGAG | 540 |
| ACACACTTTC | CCCCGCACCT | GAGGCCACAC | ACGTACTCAT | GTCCTGTAAG | CCTTGCCGAG | 600 |
| GACCCTAGGC | AATGCAGCTG | AGCCCTTCTG | AGTCTCTGCC | CTGATGATCT | TCCCTGTTGG | 660 |
| CAGATATCAT | TCATTCAGCA | AATAATCATT | GAGCATTTGT | TATATACCAA | GCACATCCTA | 720 |
| GACCCTGGGG | ATACAGCAGT | CAATGCTACA | AAGACCCAGC | TCTCTGCAG | | 769 |

( 2 ) INFORMATION FOR SEQ ID NO: 43:

( i ) SEQUENCE CHARACTERISTICS:
( A ) LENGTH: 263 base pairs
( B ) TYPE: nucleic acid
( C ) STRANDEDNESS: double -continued ( D ) TOPOLOGY: linear ( x i ) SEQUENCE DESCRIPTION: SEQ ID NO: 43:

TTTGGAACCC TGGTCAGTGC TAGGCAGTCC AGTTTCCCAA GGCTGAGGTG CTCCTCACTC            60

ACATCTTCCT TCTACTGCCC TGGTACCCAC AGTTCAACAT CTGTGCCAAC AGCAGCCTCC           120

ACGACTACGC TAAGATCTTC CCCATGAACA ACGCCACCGT GGCCGTGGAC ATTTACCAGG           180

GGGTGAGGGG GTGGGTGGGG AGGGCGTGAC CCAGAGAGGC GCCTCGGGCA GGGCCACCGG           240

TGGTACCACA CTCGTCCCTG CAG                                                   263

( 2 ) INFORMATION FOR SEQ ID NO: 44:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 44:

CCGTGGCACT TTACCGGGGG GTGAGCGCGG GTGGGTGGGG AGGGCGTGAC CCAGAGAGGC            60

TCCCCGCCTC GGGCAGGGCC ACCGGTCCTA CCACACTCGT CCCTGCAGGG CGTGATCCTG           120

GGCTGCCTGT TCGGCCCCGC GGCCCTCTAC ATCTGGGCCA TAGGTCTCCT GGCGGCTGGG           180

CAGAGCTCCA CCATGACGGG CACCTACGCG GGACAGTTCG TGATGGAGGT AGGGCAGGGG           240

GCGGGCCAGG AG                                                               252

( 2 ) INFORMATION FOR SEQ ID NO: 45:

( i ) SEQUENCE CHARACTERISTICS:
        ( A ) LENGTH: 369 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 45:

AAATGTTTAG TCTTCAGAAC CAGCTATGGG ATGGGAGTTC CCCATTTCTC CCCACCCATC            60

CCCTCTTGCC ACCTAGGGAC AGAGCTGTCC CAGTTCAACA GTGGAAAAAC AGAGCATGCC           120

CCCAGGGATA AATCGGTTGA GGGACATCAG AGGATCTCTC CTCTGGAATC CCCAGTCCTG           180

TCTACTCCTC ACCAAGGAGC TCACCCCAC CCCAGGGCTT CCTGAGGCTG CGGTGGTCAA            240

GCTTCGCCCG TGTCCTCCTC ACCCGCTCCT GCGCCATCCT GCCCACCGTG CTCGTGGCTG           300

TCTTCCGGGA CCTGAGGGAC TTGTCGGGCC TCAATGATCT GCTCAACGTG CTGCAGAGCC           360

TGCTGGTGA                                                                   369

( 2 ) INFORMATION FOR SEQ ID NO: 46:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 46:

CCAGCTCCCG GTTGCCGTGC TGCCCATCCT CACGTTCACC AGCATGCCCA CCCTCATGCA            60

GGAGTTTGCC AATGGCCTGT GAGTACCCCC TTTCCCAAGT GCTGGATTGC ATC                  113

( 2 ) INFORMATION FOR SEQ ID NO: 47:

( i ) SEQUENCE CHARACTERISTICS:
        ( A ) LENGTH: 231 base pairs (B) TYPE: nucleic acid
(C) STRANDEDNESS: double
(D) TOPOLOGY: linear (xi) SEQUENCE DESCRIPTION: SEQ ID NO: 47:

| | | | | | |
|---|---|---|---|---|---|
| CAGCAACCAG | CCAGTCCTGA | GCCTCTCTCG | TGTCCCCCAG | GCTGAACAAG | GTCGTCACCT | 60 |
| CTTCCATCAT | GGTGCTAGTC | TGCACCATCA | ACCTCTACTT | CGTGGTCAGC | TATCTGCCCA | 120 |
| GCCTGCCCCA | CCCTGCCTAC | TTCGGCCTTG | CAGCCTTGCT | GGCCGCAGCC | TACCTGGGCC | 180 |
| TCAGCACCTA | CCTGGTACAG | TAGGGCCAGG | GGATGCCTTG | GGAATGGATG | A | 231 |

(2) INFORMATION FOR SEQ ID NO: 48:

(i) SEQUENCE CHARACTERISTICS:
(A) LENGTH: 220 base pairs
(B) TYPE: nucleic acid
(C) STRANDEDNESS: double
(D) TOPOLOGY: linear (xi) SEQUENCE DESCRIPTION: SEQ ID NO: 48:

| | | | | | |
|---|---|---|---|---|---|
| TGCCTTGGGA | ATGGATGATT | CCCCAGAGGT | CTTGGCATCT | CCCCAATTCA | TGGTTGCCCC | 60 |
| TCCCCCAGGT | CTGGACCTGT | TGCCTTGCCC | ACGGAGCCAC | CTTTCTGGCC | CACAGCTCCC | 120 |
| ACCACCACTT | CCTGTATGGG | CCTCCTTGAA | GAGGACCACA | AAGGGGAGAC | CTCTGGCTAG | 180 |
| GCCCACACCA | GGGCTGGCTG | GGGAGTGGCA | TGTATGACGT | | | 220 |

(2) INFORMATION FOR SEQ ID NO: 49:

(i) SEQUENCE CHARACTERISTICS:
(A) LENGTH: 2294 base pairs
(B) TYPE: nucleic acid
(C) STRANDEDNESS: double
(D) TOPOLOGY: linear (xi) SEQUENCE DESCRIPTION: SEQ ID NO: 49:

| | | | | | |
|---|---|---|---|---|---|
| GAATTCGGCA | CGAGGGAGCT | AGTTGCCAGG | CCTGGTGACC | ACACACAGAG | TATCCTGCCG | 60 |
| CCTGCGTCCT | CATGATTAGT | GACAAGAGCC | CCCGAGGCT | GAGCAGGCCC | AGTTATGGCT | 120 |
| CCATTTCCAG | CCTGCCTGGC | CCAGCACCTC | AGCCAGCGCC | TTGCCGGGAG | ACCTACCTGA | 180 |
| GTGAGAAGAT | CCCCATTCCC | AGCGCAGACC | AGGGTACATT | CAGCCTGAGG | AAGCTGTGGG | 240 |
| CGTTCACGGG | GCCTGGTTTC | CTCATGAGCA | TCGCTTTCCT | TGACCCGGGA | AACATTGAGT | 300 |
| CCGACCTTCA | AGCTGGCGCT | GTGGCTGGGT | TCAAACTCCT | CTGGGTGCTG | CTCTGGGCCA | 360 |
| CTGTGCTAGG | TTTGCTGTGC | CAGCGGCTGG | CTGCCCGGCT | GGGCGTGGTG | ACAGGCAAGG | 420 |
| ACTTGGGTGA | AGTCTGCCAT | CTCTACTACC | CCAAGGTGCC | CCGCATCCTC | CTCTGGCTGA | 480 |
| CCATTGAGCT | GGCCATTGTG | GGCTCAGATA | TGCAGGAAGT | CATCGGGACG | GCTATCTCCT | 540 |
| TCAATCTGCT | CTCCGCTGGA | CGCATCCCGC | TGTGGGGCGG | TGTACTGATC | ACCATTGTGG | 600 |
| ACACCTTCTT | CTTCCTCTTC | TTGGATAACT | ATGGTTTGCG | CAAGCTGGAA | GCTTTCTTCG | 660 |
| GTCTCCTCAT | TACCATAATG | GCTTTGACCT | TCGGCTATGA | GTATGTGGTA | GCACACCCTT | 720 |
| CCCAGGGAGC | GCTCCTTAAG | GGCCTGGTGC | TGCCCACCTG | TCCGGGCTGT | GGGCAGCCCG | 780 |
| AGCTGCTGCA | GGCAGTGGGC | ATCGTCGGTG | CCATCATCAT | GCCCCATAAC | ATCTACCTGC | 840 |
| ACTCAGCCTT | GGTCAAGTCT | AGAGAAGTAG | ACAGAACCCG | CCGGGTGGAT | GTTCGAGAAG | 900 |
| CCAACATGTA | CTTCCTGATT | GAGGCCACCA | TCGCCCTATC | GGTGTCCTTC | ATCATCAACC | 960 |
| TCTTTGTCAT | GGCTGTTTTT | GGTCAGGCCT | TCTACCAGCA | AACCAATGAG | GAAGCGTTCA | 1020 |
| ACATCTGTGC | CAACAGCAGC | CTCCAGAACT | ATGCTAAGAT | CTTCCCCAGG | GACAATAACA | 1080 |

-continued

| | | | | | |
|---|---|---|---|---|---|
| CTGTGTCAGT | GGATATTTAT | CAAGGAGGTG | TGATCCTAGG | CTGTCTCTTT | GGCCCTGCGG | 1140 |
| CCCTCTACAT | CTGGGCAGTA | GGTCTCCTGG | CAGCGGGGCA | GAGTTCTACT | ATGACCGGCA | 1200 |
| CCTATGCAGG | ACAGTTCGTG | ATGGAGGGTT | TCCTTAAGCT | GCGGTGGTCC | CGCTTCGCTC | 1260 |
| GGGTCCTTCT | CACGCGCTCT | TGCGCCATCC | TGCCCACTGT | GTTGGTGGCT | GTCTTCCGAG | 1320 |
| ACCTGAAGGA | CCTGTCCGGC | CTCAACGATC | TACTCAATGT | TCTGCAGAGT | CTACTGCTGC | 1380 |
| CCTTCGCTGT | ACTGCCCATT | TTGACTTTCA | CCAGCATGCC | AGCTGTCATG | CAGGAGTTTG | 1440 |
| CCAACGGCCG | GATGAGCAAA | GCCATCACTT | CGTGCATCAT | GGCGCTAGTC | TGCGCCATCA | 1500 |
| ACCTGTACTT | TGTGATCAGC | TACCTGCCCA | GCCTCCCGCA | CCCTGCCTAC | TTTGGCCTTG | 1560 |
| TGGCTCTGTT | CGCAATAGGT | TACTTGGGCC | TGACTGCTTA | TCTGGCCTGG | ACCTGTTGCA | 1620 |
| TCGCCCACGG | AGCCACCTTC | CTGACCCACA | GCTCCCACAA | GCACTTCTTA | TATGGGCTCC | 1680 |
| CTAACGAGGA | GCAGGGAGGC | GTGCAGGGTT | CCGGGTGACC | GCGGCATCCA | GCAAGCAAAG | 1740 |
| AGGCAACAGG | GCAGACACAG | CAGAGCAATT | GGAGGTCCCC | TACTGGCTTT | CTGGATTACC | 1800 |
| GGTTTCCAGT | TTGGACAAGT | GCTTTACCTC | GGAATAATGA | CACCATTCTT | ATCACCACAA | 1860 |
| CCTAAGAGAC | TTAAAAAACA | CAGTGCCTGG | GGCGAGAGAT | GGCTCAGGTG | TGAAGAACAC | 1920 |
| TAGCCACCAC | CCTTTCAGAA | GATGGGGATT | CAATTCCCAG | CATCAACGTG | GTGGCTTTCA | 1980 |
| ACTGAAGGTG | ACTCCAGTTC | CCAGAACACC | TCAAACAGAA | CTGCCACAAC | TCCATTGTCT | 2040 |
| CACTCCAGCT | CGTGGAAGAT | GAAGGGAGGA | GTCCTAAAGA | GTTCTAGGTC | GGGTCTCTGG | 2100 |
| AGAGACGGCT | CAGCTGTTAA | GAGCACCCGA | CTGCTCTTCC | AGAGGTCCTG | AGTTCAATTC | 2160 |
| CCAGCAACCA | CATGGTGGCT | CACAACCATC | CATAATGGGA | TCCCTCTTCT | GGTGTGTCTG | 2220 |
| AAGACAACAA | CAGTGTCCTC | ACATATATAA | AATAAATAAA | TCTTAAAAAA | AAAAAAAAA | 2280 |
| AAAAAAACT | CGAG | | | | | 2294 |

( 2 ) INFORMATION FOR SEQ ID NO: 50:

( i ) SEQUENCE CHARACTERISTICS:
( A ) LENGTH: 548 amino acids
( B ) TYPE: amino acid
( C ) STRANDEDNESS: single
( D ) TOPOLOGY: linear ( x i ) SEQUENCE DESCRIPTION: SEQ ID NO: 50:

```
Met Ile Ser Asp Lys Ser Pro Pro Arg Leu Ser Arg Pro Ser Tyr Gly
 1               5                  10                  15

Ser Ile Ser Ser Leu Pro Gly Pro Ala Pro Gln Pro Ala Pro Cys Arg
            20                  25                  30

Glu Thr Tyr Leu Ser Glu Lys Ile Pro Ile Pro Ser Ala Asp Gln Gly
        35                  40                  45

Thr Phe Ser Leu Arg Lys Leu Trp Ala Phe Thr Gly Pro Gly Phe Leu
    50                  55                  60

Met Ser Ile Ala Phe Leu Asp Pro Gly Asn Ile Glu Ser Asp Leu Gln
65                  70                  75                  80

Ala Gly Ala Val Ala Gly Phe Lys Leu Leu Trp Val Leu Leu Trp Ala
                85                  90                  95

Thr Val Leu Gly Leu Leu Cys Gln Arg Leu Ala Ala Arg Leu Gly Val
            100                 105                 110

Val Thr Gly Lys Asp Leu Gly Glu Val Cys His Leu Tyr Tyr Pro Lys
        115                 120                 125

Val Pro Arg Ile Leu Leu Trp Leu Thr Ile Glu Leu Ala Ile Val Gly
    130                 135                 140
```

-continued

| | | | | | | | | | | | | | | |
|---|---|---|---|---|---|---|---|---|---|---|---|---|---|---|
| Ser | Asp | Met | Gln | Glu | Val | Ile | Gly | Thr | Ala | Ile | Ser | Phe | Asn | Leu | Leu |
| 145 | | | | 150 | | | | | 155 | | | | | 160 |
| Ser | Ala | Gly | Arg | Ile | Pro | Leu | Trp | Gly | Val | Leu | Ile | Thr | Ile | Val |
| | | | | 165 | | | | | 170 | | | | 175 | |
| Asp | Thr | Phe | Phe | Phe | Leu | Phe | Leu | Asp | Asn | Tyr | Gly | Leu | Arg | Lys | Leu |
| | | | 180 | | | | | 185 | | | | | 190 | | |
| Glu | Ala | Phe | Phe | Gly | Leu | Leu | Ile | Thr | Ile | Met | Ala | Leu | Thr | Phe | Gly |
| | | | 195 | | | | | 200 | | | | 205 | | | |
| Tyr | Glu | Tyr | Val | Val | Ala | His | Pro | Ser | Gln | Gly | Ala | Leu | Leu | Lys | Gly |
| | 210 | | | | | 215 | | | | | 220 | | | | |
| Leu | Val | Leu | Pro | Thr | Cys | Pro | Gly | Cys | Gly | Gln | Pro | Glu | Leu | Leu | Gln |
| 225 | | | | | 230 | | | | | 235 | | | | | 240 |
| Ala | Val | Gly | Ile | Val | Gly | Ala | Ile | Ile | Met | Pro | His | Asn | Ile | Tyr | Leu |
| | | | | 245 | | | | | 250 | | | | | 255 | |
| His | Ser | Ala | Leu | Val | Lys | Ser | Arg | Glu | Val | Asp | Arg | Thr | Arg | Arg | Val |
| | | | | 260 | | | | | 265 | | | | 270 | | |
| Asp | Val | Arg | Glu | Ala | Asn | Met | Tyr | Phe | Leu | Ile | Glu | Ala | Thr | Ile | Ala |
| | | 275 | | | | | 280 | | | | | 285 | | | |
| Leu | Ser | Val | Ser | Phe | Ile | Ile | Asn | Leu | Phe | Val | Met | Ala | Val | Phe | Gly |
| | 290 | | | | | 295 | | | | | 300 | | | | |
| Gln | Ala | Phe | Tyr | Gln | Gln | Thr | Asn | Glu | Glu | Ala | Phe | Asn | Ile | Cys | Ala |
| 305 | | | | | 310 | | | | | 315 | | | | | 320 |
| Asn | Ser | Ser | Leu | Gln | Asn | Tyr | Ala | Lys | Ile | Phe | Pro | Arg | Asp | Asn | Asn |
| | | | | 325 | | | | | 330 | | | | | 335 | |
| Thr | Val | Ser | Val | Asp | Ile | Tyr | Gln | Gly | Gly | Val | Ile | Leu | Gly | Cys | Leu |
| | | | | 340 | | | | 345 | | | | | 350 | | |
| Phe | Gly | Pro | Ala | Ala | Leu | Tyr | Ile | Trp | Ala | Val | Gly | Leu | Leu | Ala | Ala |
| | | | 355 | | | | | 360 | | | | | 365 | | |
| Gly | Gln | Ser | Ser | Thr | Met | Thr | Gly | Thr | Tyr | Ala | Gly | Gln | Phe | Val | Met |
| | | 370 | | | | | 375 | | | | | 380 | | | |
| Glu | Gly | Phe | Leu | Lys | Leu | Arg | Trp | Ser | Arg | Phe | Ala | Arg | Val | Leu | Leu |
| 385 | | | | | 390 | | | | | 395 | | | | | 400 |
| Thr | Arg | Ser | Cys | Ala | Ile | Leu | Pro | Thr | Val | Leu | Val | Ala | Val | Phe | Arg |
| | | | | 405 | | | | | 410 | | | | | 415 | |
| Asp | Leu | Lys | Asp | Leu | Ser | Gly | Leu | Asn | Asp | Leu | Leu | Asn | Val | Leu | Gln |
| | | | 420 | | | | | 425 | | | | | 430 | | |
| Ser | Leu | Leu | Leu | Pro | Phe | Ala | Val | Leu | Pro | Ile | Leu | Thr | Phe | Thr | Ser |
| | | | 435 | | | | | 440 | | | | | 445 | | |
| Met | Pro | Ala | Val | Met | Gln | Glu | Phe | Ala | Asn | Gly | Arg | Met | Ser | Lys | Ala |
| | 450 | | | | | 455 | | | | | 460 | | | | |
| Ile | Thr | Ser | Cys | Ile | Met | Ala | Leu | Val | Cys | Ala | Ile | Asn | Leu | Tyr | Phe |
| 465 | | | | | 470 | | | | | 475 | | | | | 480 |
| Val | Ile | Ser | Tyr | Leu | Pro | Ser | Leu | Pro | His | Pro | Ala | Tyr | Phe | Gly | Leu |
| | | | | 485 | | | | | 490 | | | | | 495 | |
| Val | Ala | Leu | Phe | Ala | Ile | Gly | Tyr | Leu | Gly | Leu | Thr | Ala | Tyr | Leu | Ala |
| | | | 500 | | | | | 505 | | | | | 510 | | |
| Trp | Thr | Cys | Cys | Ile | Ala | His | Gly | Ala | Thr | Phe | Leu | Thr | His | Ser | Ser |
| | | | 515 | | | | | 520 | | | | | 525 | | |
| His | Lys | His | Phe | Leu | Tyr | Gly | Leu | Pro | Asn | Glu | Glu | Gln | Gly | Gly | Val |
| | | | 530 | | | | | 535 | | | | | 540 | | |
| Gln | Gly | Ser | Gly | | | | | | | | | | | | |
| 545 | | | | | | | | | | | | | | | |

(2) INFORMATION FOR SEQ ID NO: 51:

( i ) SEQUENCE CHARACTERISTICS:
    ( A ) LENGTH: 606 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 51:

| | | | | | | |
|---|---|---|---|---|---|---|
| CCTGCGTCCT | CATGATTAGT | AATAGCCTCC | AGGGACCTAA | TGGGATTCCA | GTGGGGGTGA | 60 |
| CTTGAGGGGG | CAAGGAAGAT | TTAGGGTCTC | TGTGGGGGCT | CAGCTCTGCC | AGAGCGACTT | 120 |
| CAGTCAGGCA | CTTCTGTGGA | TTAAACCTGG | TGGAGGAGAC | AGAGCATGGG | GGTCAAGCAG | 180 |
| CTGAGCGAGG | GGCCTCCTGT | CTCACAAATC | TCCTGACTCA | GGGGATTTGG | ATTGGAGAAG | 240 |
| TTCTGTTCCT | CACTGGGAGG | GAAGTGATTC | TTGGAACCTC | TGCTTGGCAC | ATAGGTGGAC | 300 |
| CTGCCAGTTG | CGGGGAGGGA | GGTCGAGGTC | GTGGGAGGAG | GCAGGTGGCT | TGAATCCCAG | 360 |
| GCTTCTGAAA | GAAGCACACA | CCCACCTAGC | ATCCTGGGGT | CCCTGACAGG | TGACAAGAGC | 420 |
| CCCCCGAGGC | TGAGCAGGCC | CAGTTATGGC | TCCATTTCCA | GCCTGCCTGG | CCCAGCACCT | 480 |
| CAGCCAGCGC | CTTGCCGGGA | GACCTACCTG | AGTGAGAAGA | TCCCCATTCC | CAGCGCAGAC | 540 |
| CAGGTAGGGA | TGGTAGGAAT | GTCCTCAGTG | CTTCCCAGGT | CCTACCGGAT | CCGAGCTCGG | 600 |
| ACCAAG | | | | | | 606 |

( 2 ) INFORMATION FOR SEQ ID NO: 52:

( i ) SEQUENCE CHARACTERISTICS:
    ( A ) LENGTH: 1011 base pairs
    ( B ) TYPE: nucleic acid
    ( C ) STRANDEDNESS: double
    ( D ) TOPOLOGY: linear ( x i ) SEQUENCE DESCRIPTION: SEQ ID NO: 52:

| | | | | | | |
|---|---|---|---|---|---|---|
| TCAAGCTTGA | GTGCATGTGT | AGCTGTGTCC | ATTATAGAGC | ATGCGCGTGG | AGGTCAGAGG | 60 |
| ACAACTTGTG | AGAGTCAGCT | CACTTCTACT | GCGTGGGTTC | CAACTCTGGT | GGCCTTAGCC | 120 |
| TCTGAGCCCC | TTCTCGGTCC | CCATTGCCAC | ACTCTAAGCA | GATTCCTAGG | CTGTCGGGCC | 180 |
| AAACCCTGAA | ATAGAGTTGA | GTGACTGAGA | CCTCAGTGGT | CCCCAGAGAG | AAGAGCCTGA | 240 |
| AGTATGAGAA | GGGTCTGGGG | AGGGAAGAGC | TGTAGCAGGG | AGGTTTAATT | ACAACAACCT | 300 |
| CCCCCTCTTG | GGACTCTGAG | AAGCCTGAAA | GAGGCAGGCA | GGTCATGTGC | TGGCCAGCTG | 360 |
| CAGAGGCTGC | TGCTGAACAG | GACCAACCCA | GAAAGCAGAG | CCATAGTGAC | TCAGCAAATG | 420 |
| GCCCTGGTCC | CTCGGGGGAC | GGGCAGCGGT | GGCATTGGGT | GGGTGATGGA | GGACAGGGCT | 480 |
| GGCCAGCCTG | ACTGAAGAAG | ATACTGGCTG | AGTTTTTAGC | TGAGGGATG | GTCAAGGCCA | 540 |
| GCTGCATCCA | TCCAGGAGCT | AACATGACCC | GATCTGCTTG | CACCCCAGG | GTACATTCAG | 600 |
| CCTGAGGAAG | CTGTGGGCGT | TCACGGGGCC | TGGTTTCCTC | ATGAGCATCG | CTTTCCTTGA | 660 |
| CCCGGGAAAC | ATTGAGTCCG | ACCTTCAAGC | TGGCGCTGTG | GCTGGGTTCA | AAGTACTGAG | 720 |
| TCTGGGCCGC | CATGCTTGCT | TTGTGGGGAG | CACTTTCCTT | AGCTAGGACA | GGGGAGACCC | 780 |
| CAGTTTTCCA | GAGCCGGCTG | CATGGGTGGT | TTTTCTGAGG | ATAAGCTCCT | ATCGGGGAGG | 840 |
| AAAAGGAACC | TTGGAGAAAC | CCCTGGAGAA | AGGATGCTGT | AGGGTGTTAG | TCTTCCCGCC | 900 |
| CAATCCCCAT | CAGACAGGCT | GCTCTGGCTG | AGCATCTCCT | CTGTTTCCTC | ACAGCTCCTC | 960 |
| TGGGTGCTGC | TCTGGGCCAC | TGTGCTAGGT | TTGCTGTGCC | AGCGGCTGGC | T | 1011 |

( 2 ) INFORMATION FOR SEQ ID NO: 53:

( i ) SEQUENCE CHARACTERISTICS:

( A ) LENGTH: 147 base pairs
( B ) TYPE: nucleic acid
( C ) STRANDEDNESS: double
( D ) TOPOLOGY: linear ( x i ) SEQUENCE DESCRIPTION: SEQ ID NO: 53:

AGGTGACAAG GGTCCCCAAA GGCTAAGCGG GTCCAGCTAT GGTTCCATCT CCAGCCCGAC        60

CAGCCCGACC AGCCCAGGGC CACAGCAAGC ACCTCCAGA GAGACCTACC TGAGTGAGAA        120

GATCCCCATC CCAGACACAA AACCGGT        147

( 2 ) INFORMATION FOR SEQ ID NO: 54:

( i ) SEQUENCE CHARACTERISTICS:
( A ) LENGTH: 47 amino acids
( B ) TYPE: amino acid
( C ) STRANDEDNESS: single
( D ) TOPOLOGY: linear ( x i ) SEQUENCE DESCRIPTION: SEQ ID NO: 54:

Asp Lys Gly Pro Gln Arg Leu Ser Gly Ser Ser Tyr Gly Ser Ile Ser
1               5                   10                  15

Ser Pro Thr Ser Pro Thr Ser Pro Gly Pro Gln Gln Ala Pro Pro Arg
            20              25                  30

Glu Thr Tyr Leu Ser Glu Lys Ile Pro Ile Pro Asp Thr Lys Pro
        35                  40                  45

( 2 ) INFORMATION FOR SEQ ID NO: 55:

( i ) SEQUENCE CHARACTERISTICS:
( A ) LENGTH: 138 base pairs
( B ) TYPE: nucleic acid
( C ) STRANDEDNESS: double
( D ) TOPOLOGY: linear ( x i ) SEQUENCE DESCRIPTION: SEQ ID NO: 55:

AGGTGACAAG AGCCCCCCGA GGCTGAGCAG GCCCAGTTAT GGCTCCATTT CCAGCCTGCC        60

TGGCCCAGCA CCTCAGCCAG CGCCTTGCCG GGAGACCTAC CTCAGTGAGA AGATCCCCAT        120

TCCCAGCGCA GACCAGGT        138

( 2 ) INFORMATION FOR SEQ ID NO: 56:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( x i ) SEQUENCE DESCRIPTION: SEQ ID NO: 56:

Ser Asp Lys Ser Pro Pro Arg Leu Ser Arg Pro Ser Tyr Gly Ser Ile
1               5                   10                  15

Ser Ser Leu Pro Gly Pro Ala Pro Gln Pro Ala Pro Cys Arg Glu Thr
            20              25                  30

Tyr Leu Ser Glu Lys Ile Pro Ile Pro Ser Ala Asp Gln
        35                  40                  45

( 2 ) INFORMATION FOR SEQ ID NO: 57:

( i ) SEQUENCE CHARACTERISTICS:
( A ) LENGTH: 549 amino acids
( B ) TYPE: amino acid
( C ) STRANDEDNESS: single
( D ) TOPOLOGY: linear ( x i ) SEQUENCE DESCRIPTION: SEQ ID NO: 57:

-continued

| | | | | | | | | | | | | | | |
|---|---|---|---|---|---|---|---|---|---|---|---|---|---|---|
|Met|Thr|Gly|Asp|Lys|Gly|Pro|Gln|Arg|Leu|Ser|Gly|Ser|Ser|Tyr|Gly|
|1| | | |5| | | |10| | | | |15| | |
|Ser|Ile|Ser|Ser|Pro|Thr|Ser|Pro|Thr|Ser|Pro|Gly|Pro|Gln|Gln|Ala|
| | | |20| | | |25| | | |30| | | | |
|Pro|Pro|Arg|Glu|Thr|Tyr|Leu|Ser|Glu|Lys|Ile|Pro|Ile|Pro|Asp|Thr|
| | |35| | | | |40| | | |45| | | | |
|Lys|Pro|Gly|Thr|Phe|Ser|Leu|Arg|Lys|Leu|Trp|Ala|Phe|Thr|Gly|Pro|
| |50| | | | |55| | | | |60| | | | |
|Gly|Phe|Leu|Met|Ser|Ile|Ala|Phe|Leu|Asp|Pro|Gly|Asn|Ile|Glu|Ser|
|65| | | | |70| | | | |75| | | | |80|
|Asp|Leu|Gln|Leu|Gly|Pro|Val|Ala|Gly|Phe|Lys|Leu|Leu|Val|Leu|Leu|
| | | | |85| | | |90| | | | |95| | |
|Trp|Ala|Thr|Val|Leu|Gly|Leu|Leu|Cys|Gln|Arg|Leu|Ala|Ala|Arg|Leu|
| | | |100| | | |105| | | |110| | | | |
|Gly|Val|Val|Thr|Gly|Lys|Asp|Leu|Gly|Glu|Val|Cys|His|Leu|Tyr|Tyr|
| | |115| | | |120| | | |125| | | | | |
|Pro|Lys|Val|Pro|Arg|Thr|Val|Leu|Trp|Leu|Thr|Ile|Glu|Leu|Ala|Ile|
| |130| | | |135| | | |140| | | | | | |
|Val|Gly|Ser|Asp|Met|Gln|Glu|Val|Ile|Gly|Thr|Ala|Ile|Ala|Phe|Asn|
|145| | | |150| | | |155| | | | | | |160|
|Leu|Leu|Ser|Ala|Gly|Arg|Ile|Pro|Leu|Trp|Gly|Gly|Val|Leu|Ile|Thr|
| | | |165| | | |170| | | | |175| | | |
|Ile|Val|Asp|Thr|Phe|Phe|Phe|Leu|Phe|Leu|Asp|Asn|Tyr|Gly|Leu|Arg|
| | |180| | | |185| | | |190| | | | | |
|Lys|Leu|Glu|Ala|Phe|Phe|Gly|Leu|Leu|Ile|Thr|Ile|Met|Ala|Leu|Thr|
| |195| | | |200| | | |205| | | | | | |
|Phe|Gly|Tyr|Glu|Tyr|Val|Val|Ala|Arg|Pro|Glu|Gln|Gly|Ala|Leu|Leu|
| |210| | | |215| | | |220| | | | | | |
|Arg|Gly|Leu|Phe|Leu|Pro|Ser|Cys|Pro|Gly|Cys|Gly|His|Pro|Glu|Leu|
|225| | | |230| | | |235| | | | |240| | |
|Leu|Gln|Ala|Val|Gly|Ile|Val|Gly|Ala|Ile|Ile|Met|Pro|His|Asn|Ile|
| | | |245| | | |250| | | |255| | | | |
|Tyr|Leu|His|Ser|Ala|Leu|Val|Lys|Ser|Arg|Glu|Ile|Asp|Arg|Ala|Arg|
| | |260| | | |265| | | |270| | | | | |
|Arg|Val|Asp|Ile|Arg|Glu|Ala|Asn|Met|Tyr|Phe|Leu|Ile|Glu|Ala|Thr|
| |275| | | |280| | | |285| | | | | | |
|Ile|Ala|Leu|Ser|Val|Ser|Phe|Ile|Ile|Asn|Leu|Phe|Val|Met|Ala|Ala|
|290| | | |295| | | |300| | | | | | | |
|Phe|Gly|Gln|Ala|Phe|Tyr|Gln|Lys|Thr|Lys|Gln|Ala|Ala|Phe|Asn|Ile|
|305| | | |310| | | |315| | | | |320| | |
|Cys|Ala|Asn|Ser|Ser|Leu|His|Asp|Tyr|Ala|Lys|Ile|Phe|Pro|Met|Asn|
| | |325| | | |330| | | |335| | | | | |
|Asn|Ala|Thr|Val|Ala|Val|Asp|Ile|Tyr|Gln|Gly|Gly|Val|Ile|Leu|Gly|
| | |340| | | |345| | | |350| | | | | |
|Cys|Leu|Phe|Gly|Pro|Ala|Ala|Leu|Tyr|Ile|Trp|Ala|Ile|Gly|Leu|Leu|
| |355| | | |360| | | |365| | | | | | |
|Ala|Ala|Gly|Gln|Ser|Ser|Thr|Met|Thr|Gly|Thr|Tyr|Ala|Gly|Gln|Phe|
|370| | | |375| | | |380| | | | | | | |
|Val|Met|Glu|Gly|Phe|Leu|Arg|Leu|Arg|Trp|Ser|Ser|Phe|Ala|Arg|Val|
|385| | | |390| | | |395| | | | |400| | |
|Leu|Leu|Thr|Arg|Ser|Cys|Ala|Ile|Leu|Pro|Thr|Val|Leu|Val|Ala|Val|
| | |405| | | |410| | | | |415| | | | |
|Phe|Arg|Asp|Leu|Arg|Asp|Leu|Ser|Gly|Leu|Asn|Asp|Leu|Leu|Asn|Val|

|   |     |     |     |     |     |     |     |     |     |     |     |     |     |     |
|---|-----|-----|-----|-----|-----|-----|-----|-----|-----|-----|-----|-----|-----|-----|
|   |     |     |     | 420 |     |     |     | 425 |     |     |     | 430 |     |     |
| Leu | Gln | Ser | Leu | Leu | Leu | Pro | Val | Ala | Val | Pro | Ile | Leu | Thr | Phe |
|     |     | 435 |     |     |     | 440 |     |     |     | 445 |     |     |     |     |
| Thr | Ser | Met | Pro | Thr | Leu | Met | Gln | Glu | Phe | Ala | Asn | Gly | Leu | Leu | Asn |
|     |     | 450 |     |     |     | 455 |     |     |     | 460 |     |     |     |     |
| Lys | Val | Val | Thr | Ser | Ser | Ile | Met | Val | Leu | Val | Cys | Thr | Ile | Asn | Leu |
| 465 |     |     |     | 470 |     |     |     | 475 |     |     |     |     |     | 480 |
| Tyr | Phe | Val | Val | Ser | Tyr | Leu | Pro | Ser | Leu | Pro | His | Pro | Ala | Tyr | Phe |
|     |     |     |     | 485 |     |     |     | 490 |     |     |     | 495 |     |     |
| Gly | Leu | Ala | Ala | Leu | Leu | Ala | Ala | Ala | Tyr | Leu | Gly | Leu | Ser | Thr | Tyr |
|     |     |     | 500 |     |     |     | 505 |     |     |     | 510 |     |     |     |
| Leu | Val | Trp | Thr | Cys | Cys | Leu | Ala | His | Gly | Ala | Thr | Phe | Leu | Ala | His |
|     |     | 515 |     |     |     | 520 |     |     |     | 525 |     |     |     |     |
| Ser | Ser | His | His | His | Phe | Leu | Tyr | Gly | Leu | Leu | Glu | Glu | Asp | His | Lys |
|     | 530 |     |     |     | 535 |     |     |     | 540 |     |     |     |     |     |
| Gly | Glu | Thr | Ser | Gly |
| 545 |

(2) INFORMATION FOR SEQ ID NO: 58:

(i) SEQUENCE CHARACTERISTICS:
        (A) LENGTH: 576 amino acids
        (B) TYPE: amino acid
        (C) STRANDEDNESS: single
        (D) TOPOLOGY: linear (xi) SEQUENCE DESCRIPTION: SEQ ID NO: 58:

| Met | Val | Asn | Val | Gly | Pro | Ser | His | Ala | Ala | Val | Ala | Val | Asp | Ala | Ser |
| 1 |   |   |   | 5 |   |   |   |   | 10 |   |   |   |   | 15 |   |
| Glu | Ala | Arg | Lys | Arg | Asn | Ile | Ser | Glu | Glu | Val | Phe | Glu | Leu | Arg | Asp |
|   |   |   | 20 |   |   |   |   | 25 |   |   |   |   | 30 |   |   |
| Lys | Lys | Asp | Ser | Thr | Val | Val | Ile | Glu | Gly | Glu | Ala | Pro | Val | Arg | Thr |
|   |   | 35 |   |   |   |   | 40 |   |   |   |   | 45 |   |   |   |
| Phe | Thr | Ser | Ser | Ser | Ser | Asn | His | Glu | Arg | Glu | Asp | Thr | Tyr | Val | Ser |
|   | 50 |   |   |   |   | 55 |   |   |   |   | 60 |   |   |   |   |
| Lys | Arg | Gln | Val | Met | Arg | Asp | Ile | Phe | Ala | Lys | Tyr | Leu | Lys | Phe | Ile |
| 65 |   |   |   |   | 70 |   |   |   |   | 75 |   |   |   |   | 80 |
| Gly | Pro | Gly | Leu | Met | Val | Ser | Val | Ala | Tyr | Ile | Asp | Pro | Gly | Asn | Tyr |
|   |   |   |   | 85 |   |   |   |   | 90 |   |   |   |   | 95 |   |
| Ser | Thr | Ala | Val | Asp | Ala | Gly | Ala | Ser | Asn | Gln | Phe | Ser | Leu | Leu | Cys |
|   |   |   | 100 |   |   |   |   | 105 |   |   |   |   | 110 |   |   |
| Ile | Ile | Leu | Leu | Ser | Asn | Phe | Ile | Ala | Ile | Phe | Leu | Gln | Cys | Leu | Cys |
|   |   | 115 |   |   |   |   | 120 |   |   |   |   | 125 |   |   |   |
| Ile | Lys | Leu | Gly | Ser | Val | Thr | Gly | Leu | Asp | Leu | Ser | Arg | Ala | Cys | Arg |
|   | 130 |   |   |   |   | 135 |   |   |   |   | 140 |   |   |   |   |
| Glu | Tyr | Leu | Pro | Arg | Trp | Leu | Asn | Trp | Thr | Leu | Tyr | Phe | Phe | Ala | Glu |
| 145 |   |   |   |   | 150 |   |   |   |   | 155 |   |   |   |   | 160 |
| Cys | Ala | Val | Ile | Ala | Thr | Asp | Ile | Ala | Glu | Val | Ile | Gly | Thr | Ala | Ile |
|   |   |   |   | 165 |   |   |   |   | 170 |   |   |   |   | 175 |   |
| Ala | Leu | Asn | Ile | Leu | Ile | Lys | Val | Pro | Leu | Pro | Ala | Gly | Val | Ala | Ile |
|   |   |   | 180 |   |   |   |   | 185 |   |   |   |   | 190 |   |   |
| Thr | Val | Val | Asp | Val | Phe | Leu | Ile | Met | Phe | Thr | Tyr | Lys | Pro | Gly | Ala |
|   |   | 195 |   |   |   |   | 200 |   |   |   |   | 205 |   |   |   |
| Ser | Ser | Ile | Arg | Phe | Ile | Arg | Ile | Phe | Glu | Cys | Phe | Val | Ala | Val | Leu |
|   | 210 |   |   |   |   | 215 |   |   |   |   | 220 |   |   |   |   |
| Val | Val | Gly | Val | Cys | Ile | Cys | Phe | Ala | Ile | Glu | Leu | Ala | Tyr | Ile | Pro |

|   |   |   |   |   |   |   |   |   |   |   |   |   |   |   |
|---|---|---|---|---|---|---|---|---|---|---|---|---|---|---|
| 225 |   |   |   |   | 230 |   |   |   |   | 235 |   |   |   | 240 |
| Lys | Ser | Thr | Ser | Val<br>245 | Lys | Gln | Val | Phe | Arg<br>250 | Gly | Phe | Val | Pro | Ser<br>255 | Ala |

| Gln | Met | Phe | Asp<br>260 | His | Asn | Gly | Ile | Tyr<br>265 | Thr | Ala | Ile | Ser | Ile<br>270 | Leu | Gly |
|---|---|---|---|---|---|---|---|---|---|---|---|---|---|---|---|
| Ala | Thr | Val<br>275 | Met | Pro | His | Ser | Leu<br>280 | Phe | Leu | Gly | Ser | Ala<br>285 | Leu | Val | Gln |
| Pro | Arg<br>290 | Leu | Leu | Asp | Tyr | Asp<br>295 | Val | Lys | His | Gly | Asn<br>300 | Tyr | Thr | Val | Ser |
| Asp<br>305 | Glu | Gln | Asp | Lys | Val<br>310 | Lys | Ser | Lys | Ser<br>315 | Thr | Glu | Glu | Ile | Met<br>320 |
| Glu | Glu | Lys | Tyr | Phe<br>325 | Asn | Tyr | Arg | Pro | Thr<br>330 | Asn | Ala | Ala | Ile | Lys<br>335 | Tyr |
| Cys | Met | Lys | Tyr<br>340 | Ser | Met | Val | Glu | Leu<br>345 | Ser | Ile | Thr | Leu | Phe<br>350 | Thr | Leu |
| Ala | Leu | Phe<br>355 | Val | Asn | Cys | Ala | Ile<br>360 | Leu | Val | Val | Ala | Gly<br>365 | Ser | Thr | Leu |
| Tyr | Asn<br>370 | Ser | Pro | Glu | Ala | Asp<br>375 | Gly | Ala | Asp | Leu | Phe<br>380 | Thr | Ile | His | Glu |
| Leu<br>385 | Leu | Ser | Arg | Asn | Leu<br>390 | Ala | Pro | Ala | Ala<br>395 | Gly | Thr | Ile | Phe | Met<br>400 | Leu |
| Ala | Leu | Leu | Leu | Ser<br>405 | Gly | Gln | Ser | Ala | Gly<br>410 | Val | Val | Cys | Thr | Met<br>415 | Ala |
| Gly | Gln | Ile | Val<br>420 | Ser | Glu | Gly | His | Ile<br>425 | Asn | Trp | Lys | Leu | Gln<br>430 | Pro | Trp |
| Gln | Arg | Arg<br>435 | Leu | Ala | Thr | Arg | Cys<br>440 | Ile | Ser | Ile | Ile | Pro<br>445 | Cys | Leu | Val |
| Ile | Ser<br>450 | Ile | Cys | Ile | Gly | Arg<br>455 | Glu | Ala | Leu | Ser | Lys<br>460 | Ala | Leu | Asn | Ala |
| Ser<br>465 | Gln | Val | Val | Leu | Ser<br>470 | Ile | Val | Leu | Pro | Phe<br>475 | Leu | Val | Ala | Pro | Leu<br>480 |
| Ile | Phe | Phe | Thr | Cys<br>485 | Lys | Lys | Ser | Ile | Met<br>490 | Lys | Thr | Glu | Ile | Thr<br>495 | Val |
| Asp | His | Thr | Glu<br>500 | Glu | Asp | Ser | His | Asn<br>505 | His | Gln | Asn | Asn | Asn<br>510 | Asp | Arg |
| Ser | Ala | Gly<br>515 | Ser | Val | Ile | Glu | Gln<br>520 | Asp | Gly | Ser | Ser | Gly<br>525 | Ser | Met | Glu |
| Ile | Glu | Asn<br>530 | Gly | Lys | Asp | Val<br>535 | Lys | Ile | Val | Tyr | Met<br>540 | Ala | Asn | Asn | Trp |
| Ile<br>545 | Ile | Thr | Val | Ile | Ala<br>550 | Ile | Ile | Val | Trp | Leu<br>555 | Phe | Leu | Ser | Leu | Leu<br>560 |
| Asn | Val | Tyr | Ala | Ile<br>565 | Val | Gln | Leu | Gly | Met<br>570 | Ser | His | Gly | Asp | Ile<br>575 | Ser |

( 2 ) INFORMATION FOR SEQ ID NO: 59:

( i ) SEQUENCE CHARACTERISTICS:
        ( A ) LENGTH: 549 amino acids
        ( B ) TYPE: amino acid
        ( C ) STRANDEDNESS: single
        ( D ) TOPOLOGY: linear ( x i ) SEQUENCE DESCRIPTION: SEQ ID NO: 59:

| Met<br>1 | Thr | Ser | Gln | Glu<br>5 | Tyr | Glu | Pro | Ile | Gln<br>10 | Trp | Ser | Asp | Glu | Ser<br>15 | Gln |
|---|---|---|---|---|---|---|---|---|---|---|---|---|---|---|---|
| Thr | Asn | Asn | Asp | Ser | Val | Asn | Asp | Ala | Tyr | Ala | Asp | Val | Asn | Thr | Thr |

|   |   |   | 20 |   |   |   | 25 |   |   |   | 30 |   |   |
|---|---|---|---|---|---|---|---|---|---|---|---|---|---|

```
His  Glu  Ser  Arg  Arg  Arg  Thr  Thr  Leu  Gln  Pro  Asn  Ser  Thr  Ser  Gln
               35                  40                  45

Ser  Met  Ile  Gly  Thr  Leu  Arg  Lys  Tyr  Ala  Arg  Phe  Ile  Gly  Pro  Gly
50                       55                  60

Leu  Met  Val  Ser  Val  Ser  Tyr  Met  Asp  Pro  Gly  Asn  Tyr  Ser  Thr  Ala
65                       70                  75                            80

Val  Ala  Ala  Gly  Ser  Ala  His  Arg  Tyr  Lys  Leu  Leu  Phe  Ser  Val  Leu
                    85                  90                       95

Val  Ser  Asn  Phe  Met  Ala  Ala  Phe  Trp  Gln  Tyr  Leu  Cys  Ala  Arg  Leu
               100                 105                 110

Gly  Ala  Val  Thr  Gly  Leu  Asp  Leu  Ala  Gln  Asn  Cys  Lys  Lys  His  Leu
          115                 120                 125

Pro  Phe  Gly  Leu  Asn  Ile  Thr  Leu  Tyr  Ile  Leu  Ala  Glu  Met  Ala  Ile
130                      135                 140

Ile  Ala  Thr  Asp  Leu  Ala  Glu  Val  Val  Gly  Thr  Ala  Ile  Ser  Leu  Asn
145                      150                 155                           160

Ile  Leu  Phe  His  Ile  Pro  Leu  Ala  Leu  Gly  Val  Ile  Leu  Thr  Val  Val
                    165                 170                      175

Asp  Val  Leu  Ile  Val  Leu  Leu  Ala  Tyr  Lys  Pro  Asn  Gly  Ser  Met  Lys
               180                 185                      190

Gly  Ile  Arg  Ile  Phe  Glu  Ala  Phe  Val  Ser  Leu  Leu  Val  Leu  Thr
          195                 200                      205

Val  Val  Cys  Phe  Thr  Val  Glu  Leu  Phe  Tyr  Ala  Lys  Leu  Gly  Pro  Ala
210                      215                 220

Lys  Glu  Ile  Phe  Ser  Gly  Phe  Leu  Pro  Ser  Lys  Ala  Val  Phe  Glu  Gly
225                      230                 235                           240

Asp  Gly  Leu  Tyr  Leu  Ser  Leu  Ala  Ile  Leu  Gly  Ala  Thr  Val  Met  Pro
               245                 250                      255

His  Ser  Leu  Tyr  Leu  Gly  Ser  Gly  Val  Gln  Pro  Arg  Leu  Arg  Glu
               260                 265                      270

Tyr  Asp  Ile  Lys  Asn  Gly  His  Tyr  Leu  Pro  Asp  Ala  Asn  Asp  Met  Asp
               275                 280                 285

Asn  Asn  His  Asp  Asn  Tyr  Arg  Pro  Ser  Tyr  Glu  Ala  Ile  Ser  Glu  Thr
290                      295                      300

Leu  His  Phe  Thr  Ile  Thr  Glu  Leu  Leu  Ile  Ser  Leu  Phe  Thr  Val  Ala
305                      310                 315                           320

Leu  Phe  Val  Asn  Cys  Ala  Ile  Leu  Ile  Val  Ser  Gly  Ala  Thr  Leu  Tyr
                    325                 330                      335

Gly  Ser  Thr  Gln  Asn  Ala  Glu  Glu  Ala  Asp  Leu  Phe  Ser  Ile  Tyr  Asn
               340                 345                      350

Leu  Leu  Cys  Ser  Thr  Leu  Ser  Lys  Gly  Ala  Gly  Thr  Val  Phe  Val  Leu
          355                 360                      365

Ala  Leu  Leu  Phe  Ser  Gly  Gln  Ser  Ala  Gly  Ile  Val  Cys  Thr  Leu  Ser
     370                      375                 380

Gly  Gln  Met  Val  Ser  Glu  Gly  Phe  Leu  Asn  Trp  Thr  Val  Ser  Pro  Ala
385                      390                 395                           400

Leu  Arg  Arg  Ser  Ala  Thr  Arg  Ala  Val  Ala  Ile  Thr  Pro  Cys  Leu  Ile
                    405                 410                      415

Leu  Val  Leu  Val  Ala  Gly  Arg  Ser  Gly  Leu  Ser  Gly  Ala  Leu  Asn  Ala
               420                 425                      430

Ser  Gln  Val  Val  Leu  Ser  Leu  Leu  Leu  Pro  Phe  Val  Ser  Ala  Pro  Leu
          435                 440                      445
```

-continued

```
Leu  Tyr  Phe  Thr  Ser  Ser  Lys  Lys  Ile  Met  Arg  Val  Gln  Leu  Asn  Arg
     450                 455                      460

Thr  Lys  Glu  Leu  Ser  Arg  Thr  Thr  Asp  Lys  Lys  Pro  Val  Ala  Asp  Arg
465                      470                 475                           480

Thr  Glu  Asp  Asp  Glu  Thr  Ile  Glu  Leu  Glu  Met  Gly  Ile  Gly  Ser
               485                      490                      495

Ser  Ser  Gln  Glu  Arg  Ser  Leu  Val  Ser  Pro  Ala  Pro  Glu  Tyr  Lys  Asp
               500                 505                      510

Met  Ser  Asn  Gly  Met  Ile  Val  Thr  Val  Leu  Ala  Ile  Ile  Val  Trp  Leu
          515                 520                      525

Ile  Ile  Ser  Gly  Leu  Asn  Phe  Tyr  Met  Leu  Leu  Gly  Phe  Thr  Thr  Gly
     530                 535                      540

Lys  Glu  Val  His  Leu
545
```

( 2 ) INFORMATION FOR SEQ ID NO: 60:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( x i ) SEQUENCE DESCRIPTION: SEQ ID NO: 60:

```
Xaa  Xaa  Xaa  Pro  Xaa  Xaa  Leu  Ser  Xaa  Ser  Ser  Tyr  Gly  Ser  Xaa  Ser
1                   5                   10                           15

Ser  Pro  Xaa  Ser  Pro  Thr  Ser  Pro  Gly  Pro  Xaa  Xaa  Ala  Pro  Pro  Arg
          20             25                           30

Glu  Thr  Tyr  Leu  Xaa  Glu  Lys  Ile  Pro  Xaa
          35                  40
```

( 2 ) INFORMATION FOR SEQ ID NO: 61:

( i ) SEQUENCE CHARACTERISTICS:
        ( A ) LENGTH: 98 amino acids
        ( B ) TYPE: amino acid
        ( C ) STRANDEDNESS: single
        ( D ) TOPOLOGY: linear ( x i ) SEQUENCE DESCRIPTION: SEQ ID NO: 61:

```
Val  Ser  Gly  Thr  Val  Cys  Asn  Ala  Thr  Asn  Leu  Ser  Pro  Glu  Asp  Ala
1                   5                   10                           15

Val  Lys  Cys  Ser  Asp  Leu  Thr  Leu  Asp  Ser  Ser  Ser  Phe  Leu  Leu  Arg
               20                  25                       30

Asn  Val  Leu  Gly  Lys  Ser  Ser  Ala  Thr  Val  Tyr  Gly  Val  Ala  Leu  Leu
          35                  40                       45

Ala  Ser  Gly  Gln  Ser  Ser  Thr  Ile  Thr  Gly  Thr  Tyr  Ala  Gly  Cys  Gln
     50                       55                       60

Tyr  Val  Met  Gln  Gly  Phe  Leu  Asp  Ile  Lys  Met  Lys  Gln  Trp  Leu  Arg
65                       70                  75                            80

Asn  Leu  Met  Thr  Arg  Ser  Ile  Ala  Ile  Val  Pro  Ser  Leu  Ile  Val  Ser
                    85                  90                            95

Ile  Ile
```

( 2 ) INFORMATION FOR SEQ ID NO: 62:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( x i ) SEQUENCE DESCRIPTION: SEQ ID NO: 62:

| Val | Ser | Gly | Ala | Val | Cys | Asn | Ala | Pro | Asn | Leu | Ser | Pro | Glu | Asp | Arg |
|---|---|---|---|---|---|---|---|---|---|---|---|---|---|---|---|
| 1 | | | | 5 | | | | | 10 | | | | | 15 | |

| Ala | Asn | Cys | Glu | Asp | Leu | Asp | Leu | Asn | Lys | Ala | Ser | Phe | Leu | Leu | Arg |
|---|---|---|---|---|---|---|---|---|---|---|---|---|---|---|---|
| | | | 20 | | | | | 25 | | | | | 30 | | |

| Asn | Val | Val | Gly | Lys | Trp | Ser | Ser | Lys | Leu | Phe | Ala | Ile | Ala | Leu | Leu |
|---|---|---|---|---|---|---|---|---|---|---|---|---|---|---|---|
| | | 35 | | | | | 40 | | | | | 45 | | | |

| Ala | Ser | Gly | Gln | Ser | Ser | Thr | Ile | Thr | Gly | Thr | Tyr | Ala | Gly | Gln | Tyr |
|---|---|---|---|---|---|---|---|---|---|---|---|---|---|---|---|
| | 50 | | | | | 55 | | | | | 60 | | | | |

| Val | Met | Leu | Gly | Phe | Leu | Asp | Leu | Arg | Leu | Glu | Pro | Trp | | | |
|---|---|---|---|---|---|---|---|---|---|---|---|---|---|---|---|
| 65 | | | | | 70 | | | | | 75 | | | | | |

( 2 ) INFORMATION FOR SEQ ID NO: 63:

( i ) SEQUENCE CHARACTERISTICS:
( A ) LENGTH: 596 base pairs
( B ) TYPE: nucleic acid
( C ) STRANDEDNESS: double
( D ) TOPOLOGY: linear ( x i ) SEQUENCE DESCRIPTION: SEQ ID NO: 63:

```
CTGCAGTGCC  TTCCTCTGTG  GCCCTCAAAG  GAAACTGAAG  CCTTTGAGGA  CATGAAGACT      60

CGCATTAGGC  CAACGAGGGG  TCTGGAACTC  CAGATCAAAG  AGAATAAGAA  AGACCTGACT     120

CTGTGTGTGT  GTACGTGTGT  GTGTACGTGT  GTGTGTGTGT  GTGTGGCAGA  GGGGGGTGTG     180

GTCATGGGGT  ATTGACATGA  ATACGCAAGG  GGCAGGAAGC  ATCTGAAATC  AGAGCTAACT     240

TGGGAGGCAC  AGAACACGGG  GTGCCTGGAA  GGGAACAGAT  GTGTTGTGGG  GCACAGGGCA     300

GGCTGGGAGG  GAACAAAGGT  CCACTCCATG  GGTAACCAGA  CCCATTCCGC  CAGGGCTGGC     360

CACTTCTGCC  TTTGGAAAAT  GTTTCACAAC  GCCCCATGTT  GTGTGTGTGT  GTGAATCGGC     420

CGATGTGAAC  CGAATGTTGA  TGTAAGAGGC  AGGGCACTCG  GCTGCGGATG  GGTAACAGGG     480

CGTGGGCTGG  CACACTTACT  TGCACCAGTG  CCCAGAGAGG  GGGTGCAGGC  TGAGGAGCTG     540

CCCAGAGCAC  CGCTCACACT  CCCAGAGTAC  CTGAAGTCGG  CATTTCAATG  ACAGGT        596
```

We claim:

1. An isolated sequence comprising the promoter region of the nucleotide sequence of human NRAMP, which promoter region includes a poly gt site.

2. A nucleotide sequence according to claim 1, wherein the poly gt site is of general formula t(gt)$_5$ac(gt)$_5$ac(gt)$_n$g, in which n=0 or an integer.

3. A nucleotide primer pair which hybridizes to sequences specific to the 5' region of the nucleotide sequence according to claim 1 or claim 2, thereby permits amplification of at least a portion thereof.

4. A nucleotide primer pair according to claim 3, wherein the portion of the nucleotide sequence which is amplified is the poly gt site.

5. A nucleotide probe capable of hybridising to the nucleotide sequence according to claim 1.

6. A nucleotide probe according to claim 5, which comprises an allele-specific probe or an oligonucleotide.

7. A polypeptide fragment of an NRAMP protein, which comprises an amino acid sequence selected from DKSPPRLSRPSYGSISS (SEQ ID NO: 12), PQPAPCRETYLSEKIPIP (SEQ ID NO: 13), GTFSLRKLWAFTGPGFLMSIAFLDPGNIESDLQ (SEQ ID NO: 14) and WTCCIAHGATFLTHSSHKHFLYGL (SEQ ID NO: 15).

8. An antibody to a polypeptide fragment according to claim 7.

9. A method of using a primer pair according to claim 3 to detect a polymorphism in the NRAMP promoter region.

10. A method of using a probe according to claim 5 to detect a polymorphism in the NRAMP promoter region.

* * * * *